United States Patent
Nielsen et al.

(10) Patent No.: US 12,133,543 B2
(45) Date of Patent: Nov. 5, 2024

(54) ACIDIC BETA-LACTOGLOBULIN BEVERAGE PREPARATION

(71) Applicant: ARLA FOODS AMBA, Viby J (DK)

(72) Inventors: Søren Bang Nielsen, Herning (DK); Kasper Bøgelund Lauridsen, Silkeborg (DK); Tanja Christine Jæger, Kibæk (DK); Kåre Søndergaard, Holstebro (DK); Guilherme De Moura Maciel, Herning (DK); Hans Bertelsen, Videbæk (DK); Behnaz Razi Parjikolaei, Herning (DK)

(73) Assignee: ARLA FOODS AMBA, Viby J (DK)

( * ) Notice: Subject to any disclaimer, the term of this patent is extended or adjusted under 35 U.S.C. 154(b) by 652 days.

(21) Appl. No.: 17/254,738

(22) PCT Filed: Jun. 26, 2019

(86) PCT No.: PCT/EP2019/067015
§ 371 (c)(1),
(2) Date: Dec. 21, 2020

(87) PCT Pub. No.: WO2020/002435
PCT Pub. Date: Jan. 2, 2020

(65) Prior Publication Data
US 2022/0192214 A1    Jun. 23, 2022

(30) Foreign Application Priority Data

Jun. 27, 2018 (EP) .................................. 18180212
Jun. 27, 2018 (EP) .................................. 18180224
(Continued)

(51) Int. Cl.
*A23L 2/39* (2006.01)
*A23C 9/142* (2006.01)
(Continued)

(52) U.S. Cl.
CPC .............. *A23L 2/39* (2013.01); *A23C 9/1427* (2013.01); *A23J 1/205* (2013.01); *A23J 3/08* (2013.01);
(Continued)

(58) Field of Classification Search
CPC .......... A23L 2/39; A23L 33/19; A23L 33/135; A23L 2/102; A23L 2/46; A23L 2/60;
(Continued)

(56) References Cited

U.S. PATENT DOCUMENTS 2,790,790 A    4/1957   Kostergaard
4,351,710 A    9/1982   Jain
(Continued)

FOREIGN PATENT DOCUMENTS

AU    2006328958 A1   6/2007
CA       1243887 A   11/1988
(Continued)

OTHER PUBLICATIONS

Tai et al.; "β-Lactoglobulin Influences Human Immunity and Promotes Cell Proliferation"; Nov. 13, 2016; National Library of Medicine; https://www.ncbi.nlm.nih.gov/pmc/articles/PMC5124466/ (Year: 2016).*
(Continued)

*Primary Examiner* — Drew E Becker
*Assistant Examiner* — Austin Parker Taylor
(74) *Attorney, Agent, or Firm* — Casimir Jones SC; Lisa Mueller

(57) ABSTRACT

The present invention pertains to a new packaged, heat-treated beverage preparation having a pH in the range of 2.0-4.7. The invention furthermore relates to a method of producing a packaged, heat-treated beverage preparation and to different uses of the packaged, heat-treated beverage preparation.

24 Claims, 13 Drawing Sheets

120 °C/20s    120 °C/20s    75 °C/15s    75 °C/15s
BLG pH 3.7    WPI-B pH 3.7  WPI-B pH 3.7  BLG pH 3.7

(30) Foreign Application Priority Data

Jun. 27, 2018 (WO) .............. PCT/EP2018/067280
Jun. 27, 2018 (WO) .............. PCT/EP2018/067299
Jun. 27, 2018 (WO) .............. PCT/EP2018/067316

(51) Int. Cl.

| | |
|---|---|
| A23J 1/20 | (2006.01) |
| A23J 3/08 | (2006.01) |
| A23L 2/10 | (2006.01) |
| A23L 2/46 | (2006.01) |
| A23L 2/60 | (2006.01) |
| A23L 2/66 | (2006.01) |
| A23L 2/68 | (2006.01) |
| A23L 33/135 | (2016.01) |
| A23L 33/19 | (2016.01) |
| A23P 10/40 | (2016.01) |
| A61K 9/00 | (2006.01) |
| A61K 38/01 | (2006.01) |
| C07K 14/47 | (2006.01) |

(52) U.S. Cl.
CPC .............. *A23L 2/102* (2013.01); *A23L 2/46* (2013.01); *A23L 2/60* (2013.01); *A23L 2/66* (2013.01); *A23L 2/68* (2013.01); *A23L 33/135* (2016.08); *A23L 33/19* (2016.08); *A23P 10/40* (2016.08); *A61K 9/0095* (2013.01); *A61K 38/018* (2013.01); *C07K 14/4717* (2013.01); *A23V 2002/00* (2013.01)

(58) Field of Classification Search
CPC ... A23L 2/66; A23L 2/68; A23L 2/385; A23L 2/48; A23L 2/58; A23L 2/62; A23L 2/70; A23P 10/40; A23C 9/1427; A23J 1/205; A23J 3/08; A23J 1/20; A61K 9/0095; A61K 38/018; C07K 14/4717; A23V 2002/00
USPC .............................. 426/588, 580, 590, 583
See application file for complete search history.

(56) References Cited

U.S. PATENT DOCUMENTS

| | | | |
|---|---|---|---|
| 4,485,040 A | 11/1984 | Roger et al. | |
| 4,659,667 A | 4/1987 | Brewer et al. | |
| 5,008,376 A | 4/1991 | Bottomely | |
| 5,077,067 A | 12/1991 | Thibault | |
| 5,093,143 A | 3/1992 | Behr et al. | |
| 5,278,288 A | 1/1994 | Kawasaki et al. | |
| 5,420,249 A | 5/1995 | de Wit et al. | |
| 5,436,020 A | 7/1995 | Kuwata et al. | |
| 5,455,331 A | 10/1995 | Pearce | |
| 5,503,864 A | 4/1996 | Uchida et al. | |
| 5,641,531 A * | 6/1997 | Liebrecht .............. | A23L 2/66 426/583 |
| 5,719,048 A | 2/1998 | Nilsson et al. | |
| 5,744,179 A | 4/1998 | Shimamura et al. | |
| 5,747,647 A * | 5/1998 | Stack .............. | A23J 1/205 530/418 |
| 5,756,681 A | 5/1998 | Neurath et al. | |
| 5,898,067 A | 4/1999 | Balschmidt et al. | |
| 5,961,934 A | 10/1999 | Arnowitz et al. | |
| 5,986,063 A | 11/1999 | Etzel | |
| 6,312,755 B1 | 11/2001 | Wu | |
| 6,372,276 B1 | 4/2002 | Lindquist | |
| 6,528,622 B1 | 3/2003 | Ayers et al. | |
| 6,613,377 B2 | 9/2003 | Wu | |
| 6,998,259 B1 | 2/2006 | Davis et al. | |
| 8,791,064 B2 * | 7/2014 | Livney .............. | A23L 33/15 977/773 |
| 10,834,934 B2 | 11/2020 | Mikkelsen et al. | |
| 2001/0050150 A1 | 12/2001 | Gu | |
| 2002/0061359 A1 | 5/2002 | Baker et al. | |
| 2003/0078392 A1 | 4/2003 | Leaver et al. | |
| 2006/0003073 A1 * | 1/2006 | Etzel .............. | C07K 14/47 426/583 |
| 2006/0040033 A1 | 2/2006 | Zeller | |
| 2007/0148307 A1 * | 6/2007 | Sherwood .............. | A23L 2/68 426/590 |
| 2007/0172474 A1 | 7/2007 | Zemel | |
| 2008/0193601 A1 | 8/2008 | Nasser | |
| 2009/0074918 A1 | 3/2009 | Foegeding et al. | |
| 2011/0038942 A1 | 2/2011 | Livney | |
| 2011/0046048 A1 * | 2/2011 | Minor .............. | A23L 33/17 514/5.5 |
| 2011/0150824 A1 | 6/2011 | Faber et al. | |
| 2011/0218327 A1 | 9/2011 | Hansen et al. | |
| 2012/0029165 A1 | 2/2012 | Etzel et al. | |
| 2012/0064058 A1 * | 3/2012 | Cavallo .............. | A61P 3/04 424/94.1 |
| 2012/0211392 A1 | 8/2012 | Jung et al. | |
| 2013/0065822 A1 | 3/2013 | Miller et al. | |
| 2013/0129899 A1 | 5/2013 | Ummadi et al. | |
| 2013/0171318 A1 | 7/2013 | Bovetto et al. | |
| 2014/0170266 A1 * | 6/2014 | Siemensma .............. | A23C 3/08 426/384 |
| 2014/0255583 A1 * | 9/2014 | Sarama .............. | A23L 2/00 426/580 |
| 2014/0287095 A1 | 9/2014 | Li et al. | |
| 2015/0250221 A1 * | 9/2015 | Patel .............. | A23L 2/52 426/590 |
| 2016/0227828 A1 | 8/2016 | Chapman et al. | |
| 2016/0262424 A1 | 9/2016 | Mikkelsen et al. | |
| 2017/0142993 A1 | 5/2017 | Neiss | |
| 2017/0318835 A1 | 11/2017 | Lihme et al. | |
| 2018/0125926 A1 | 5/2018 | Williams et al. | |
| 2019/0364917 A1 | 12/2019 | Sher et al. | |

FOREIGN PATENT DOCUMENTS

| | | | |
|---|---|---|---|
| CN | 1817149 A | 8/2006 | |
| CN | 101031208 A | 9/2007 | |
| CN | 102711528 A | 10/2012 | |
| CN | 102746395 A | 10/2012 | |
| CN | 105792659 A | 7/2016 | |
| CN | 105792663 A | 7/2016 | |
| CN | 106581587 A | 4/2017 | |
| CN | 106798345 A | 6/2017 | |
| CN | 107048137 A * | 8/2017 | .............. A23L 2/39 |
| CN | 107105691 A | 8/2017 | |
| CN | 109843072 A | 6/2019 | |
| CN | 110381745 A | 10/2019 | |
| CN | 110621164 A | 12/2019 | |
| EP | 0126290 A1 | 11/1984 | |
| EP | 0311283 | 4/1989 | |
| EP | 0412590 | 2/1991 | |
| EP | 0604684 | 7/1994 | |
| EP | 1839492 A1 | 10/2007 | |
| EP | 2225951 A1 | 9/2010 | |
| EP | 2316283 | 5/2011 | |
| EP | 3097790 B1 * | 5/2018 | |
| FR | 2296428 A1 | 7/1976 | |
| FR | 2687901 | 9/1993 | |
| IE | 62295 | 1/1995 | |
| IE | 62295 B1 | 1/1995 | |
| JP | S61268138 A | 11/1986 | |
| JP | H05236883 A | 9/1993 | |
| JP | H06292514 A | 10/1994 | |
| JP | H07123927 A | 5/1995 | |
| JP | H09238614 A * | 9/1997 | |
| JP | H10 218755 | 8/1998 | |
| JP | 2006508160 A | 3/2006 | |
| JP | 2008525019 A | 7/2008 | |
| JP | 2009531044 A | 9/2009 | |
| JP | 2013053053 | 3/2013 | |
| JP | 2013509335 A | 3/2013 | |
| JP | 2013521779 A | 6/2013 | |
| JP | 2013532486 A | 8/2013 | |
| JP | 2015530123 A | 10/2015 | |
| WO | 1992011770 A1 | 7/1992 | |

(56) References Cited

FOREIGN PATENT DOCUMENTS

| WO | WO 1994022903 | | 10/1994 | | |
|---|---|---|---|---|---|
| WO | WO 95/34216 | | 12/1995 | | |
| WO | 1996036728 | A1 | 11/1996 | | |
| WO | WO 99/29183 | | 6/1999 | | |
| WO | WO 01/05243 | | 1/2001 | | |
| WO | WO 01/52665 | | 7/2001 | | |
| WO | WO 2002/056707 | | 7/2002 | | |
| WO | 2004049819 | A2 | 6/2004 | | |
| WO | WO 2004/049819 | | 6/2004 | | |
| WO | WO 2005/004616 | | 1/2005 | | |
| WO | WO 2007/110421 | | 10/2007 | | |
| WO | WO-2008136671 | A1 | * | 11/2008 | ........... A23C 9/1307 |
| WO | 2009038746 | A1 | 3/2009 | | |
| WO | WO 2009/038746 | | 3/2009 | | |
| WO | 2009082229 | A2 | 7/2009 | | |
| WO | WO 2009/112036 | | 9/2009 | | |
| WO | WO 2009/113845 | | 9/2009 | | |
| WO | WO 2009/113858 | | 9/2009 | | |
| WO | WO 2010/037736 | | 4/2010 | | |
| WO | WO 2010/085957 | | 8/2010 | | |
| WO | WO 2011/051436 | | 5/2011 | | |
| WO | WO 2011/112695 | | 9/2011 | | |
| WO | WO 2011119004 | A2 | 9/2011 | | |
| WO | WO 2013167720 | A1 | 11/2013 | | |
| WO | WO 2014/055830 | | 4/2014 | | |
| WO | WO 2014/076252 | | 5/2014 | | |
| WO | WO 2015/095542 | | 6/2015 | | |
| WO | WO 2016/041988 | | 3/2016 | | |
| WO | WO 2016/041995 | | 3/2016 | | |
| WO | WO 2016/055064 | | 4/2016 | | |
| WO | WO 2018/115520 | | 6/2018 | | |
| WO | 2019234957 | A1 | 12/2019 | | |
| WO | 2021126057 | A1 | 6/2021 | | |

OTHER PUBLICATIONS

Amundson et al., "Production of enriched protein fractions of beta-lactoglobulin and alpha-lactalbunin from cheese whey" Journal of Food Processing and Preservation 1982, 6: 55-71.
Anonymous: "Whey protein" Wikipedia, Dec. 20, 2016, pp. 1-5, retrieved on Feb. 15, 2018.
Aschaffenburg et al. "Improved Method for the Preparation of Crystalline beta-Lactoglobulin and alpha-Lactalbumin from Cow's Milk" Bioch. 1957, vol. 65, pp. 273-277.
Boland, Handbook of food proteins: Whey Proteins, Chapter 3, 1st ed.; Woodhead Publishing Limited, 2011; pp. 30-55.
Coquerel, "Crystallization of molecular systems from solution: phase diagrams, supersaturation and other basic concepts" Chem Soc Rev Jan. 2014, 43:2286-2300.
Czerwenka et al., "Investigation of the Lactosylation of Whey Proteins by Liquid Chromatography-Mass Spectrometry" J. Agric. Food Chem. 2006, 54: 8874-8882.
De Jongh et al., "Mild Isolation Procedure Discloses New Protein Structural Properties of β-Lactoglobulin" J. Dairy Sci. 2001, 84:562-571.
Doultani et al "Whey Protein Isolate and Glyco-macropeptide Recovery from Whey Using Ion Exchange Chromatography" Journal of Food Science May 1, 2003, 68(4): 1389-1395.
Etzel, "The emerging role of dairy proteins and bioactive peptides in nutrition and health" The Journal of Nutrition, American Society for Nutritional Sciences 2004, 996S-1002S.
Fox et al., "Fundamentals of Cheese Science" An Aspen Publication 2000, 1260-9. pp. 403-405, and pp. 517-519.
Fox et al., "Separation of beta-lactoglobulin from other milk serum proteins by trichloroacetic Acid" J. Dairy Science 1967, 50(9): 1364-1367.
Guerra-Hernandez et al., "Maillard Reaction Evaluation by Furosine Determination During Infant Cereal Processing" Journal of Cereal Science 1999, 29: 171-176.
Halford et al., "Satiety-enhancing products for appetite control: science and regulation of functional foods for weight management" Proceedings of the Nutrition Society 2012, 71: 350-362.

Hannigan "Super protein from acid whey" Food Engineering Mar. 1982, 54(3): 96-97.
Harrison et al., "Crystallization" in: "Bioseparations Science and Engineering", Jan. 27, 2015, Oxford University Press, pp. 362-383.
Jung et al., "Liquid Crystalline Phase Behavior of Protein Fibers in Water: Experiments versus Theory" Langmuir 2009, 26(1): 504-514.
Kim et al, "High-level expression of bovine b-lactoglobulin in Pichia pastoris and characterization of its physical properties" Protein Engineering 1997, 10(11): 1339-1345.
Kramer et al., "Effect of Oxidation and Protein Unfolding on Cross-Linking of beta-Lactoglobulin and alpha-Lactalbumin" J. Agric. Food Chem. 2017, 65:10258-10269.
Larson, B.L., et al. "Origin of the major specific proteins in milk"—From the Laboratory of Biochemistry, Department of Dairy Science, University of Illinois, Urbana, Illinois, Jan. 31, 1957, pp. 565-573.
Lien, "Infant formulas with increased concentrations of alpha-lactalbumin" Am J Clin Nutr 2003;77(suppl):1555S-8S.
Lovett et al. "Calcium Chloride and Vitamin D Bioavailability from Fortified Sports Drink in Wistar Rats" Int J Food Nutr 2014, Sci 1(1): 6-12.
Lozano et al., "An improved method for isolation of beta-lactoglobulin" International dairy journal 2008, 18:55-63.
Miranda, E.A., et al: "Crystallization of Lactose and Whey Protein"; "Chapter 6" in: Jane Selia dos Reis Coimbra and Jose A. Teixeira: "Engineering Aspects of Milk and Dairy Products" Nov. 24, 2009, Taylor & Francis, pp. 121-153.
Mulet-Cabero et al., "Structural mechanism and kinetics of in vitro gastric digestion are affected by process-induced changes in bovine milk" Food Hydrocolloids 2019, 86:172-183.
Muller et al., "Purification of α-lactalbumin from a prepurified acid whey: Ultrafiltration or precipitation" Lait 2003, 83:439-451.
Nicorescu et al., "Effect of dynamic heat treatment on the physical properties of whey protein foams" Food Hydrocolloids 2009, 23(4):1209-1219.
Oliveira et al., "Crystal structures of bovine β-Lactoglobulin in the orthorhombic space group C222-1. Structural differences between genetic variants A and B and features of the Tanford transition" Eur J. Biochem 2001, 268: 477-483.
Palmer "The preparation of a crystalline globulin from the albumin fraction of cow's milk" J. Biol. Chem., vol. 104, No. 2. Feb. 1, 1934, pp. 359-372.
Qin et al., "Functional implications for structural differences between variants A and B of bovine β-Lactoglobulin," Protein Science 1999, 8:75-83.
Sharma et al., "Functionality of milk powders and milk-based powders for end use applications—a review" Comprehensive Reviews in food science and food safety, Institute of Food Technologists, Chicago, IL, USA. vol. 11, No. 5, Sep. 1, 2012, pp. 518-528.
Siddique et al., "Influence of pulsed light treatment on the aggregation of whey protein isolate" Food Research International 2017, 99: 419-425.
Slack et al. "Production of Enriched Beta-Lactoglobulin and Alpha-Lactalbumin Whey Protein Fractions" Journal of Food Processing and Preservation 1986, vol. 10, pp. 19-30.
Slack et al., "Foaming and emulsifying characteristics of fractioned whey protein" Journal of Food Processing and Preservation 1986, vol. 10, pp. 81-88.
Soyeurt et al. "Mid-infrared prediction of lactoferrin content in bovine milk: potential indicator of mastitis" Animal 2012, 6:11, pp. 1830-1838.
Steinrauf "Preliminary X-ray data for some new crystalline forms of Beta-lactoglobulin and hen egg-white lysozyme" Acta Cryst. 1959, 12, 77, pp. 77-79.
Thermal technologies in food processing: Continuous heat processing, Chapter 3, Edited by Philip Richardson, Woodhead Publishing Limited, Cambridge, England, 2001, pp. 29-48.
Turhan et al., "Whey Protein Isolate and alpha-Lactalbumin Recovery from Lactic Acid Whey Using Cation-Exchange Chromatography" Journal of Food Science 2004, 69(2): 66-70.
Vyas et al "Scale-Up of Native beta-lactoglobulin Affinity separation process" J. Dairy Sci. 2002, 85:1639-1645.

(56) References Cited

OTHER PUBLICATIONS

C. Bramaud, et al., "Whey Protein Fractionation: Isoelectric Precipitation of a-Lactalbumin under Gentle Heat Treatment," Biotechnol Bioeng. Nov. 20, 1997;56(4):391-7.
Genevieve Gesan-Guiziou, et al. "Process steps for the preparation of purified fractions of a-lactalbumin and b-lactoglobulin from whey protein concentrates," Journal of Dairy Research (1999) 66 225-236, Jan. 1, 1999.
Larson & Jennes, "Beta-Lactoglobulin", Biochemical Preparations 1995, pp. 23-28.
Jongh et al., Mild isolation procedure discloses new protein structural properties of beta-lactoglobulin. J Dairy Sci. Mar. 2001;84(3):562-71.
De Wit, J.N., van Kessel, Th., "Effects of ionic strength on the solubility of whey protein products. A colloid chemical approach", 1996, Food Hydrocolloids, vol. 10, No. 2, pp. 143-149 (Year: 1996).
Polis et al., "Isolation of an Electrophoretically Homogenous Crystalline Component of β-Lactoglobulin", 1950, Journal of the American Chemical Society, vol. 72, pp. 4965-4968 (Year: 1950).
Faraji Dizaji, N., "Minor Whey Protein Purification Using ion-Exchange Column Chromatography", Apr. 2016, Electronic Thesis and Dissertation Repository, West University, 3685 (Year: 2016).
"Rotary evaporators", 2015, https://scientificservices.eu/item/rotary-evaporators/1068 (Year: 2015).
Kirkwood, J., et al. "Using isoelectric point to determine the pH for initial protein crystallization trials," Bioinformatics, 31(9), 2015, 1444-1451, Jan. 7, 2015; doi: 10.1093/bioinformatics/btv011.
Majhi, P.R., et al. "Electrostatically Driven Protein Aggregation: B-Lactoglobulin at Low Ionic Strength," Langmuir. Jul. 28, 2006; 22(22):9150-9. doi: 10.1021/la053528w.
Maria Dolores Pérez, et al., "Interaction of β-Lactoglobulin with Retinol and Fatty Acids and Its Role as a Possible Biological Function for This Protein: A Review," Journal of Dairy Science, vol. 78, Issue 5, May 1995, pp. 978-988.
Mayyada M H El-Sayed, et al., "Trends in whey protein fractionation," Biotechnol Lett. Aug. 2011;33(8):1501-11. doi: 10.1007/s10529-011-0594-8. Epub Mar. 19, 2011.
Mark R Etzel, "Manufacture and use of dairy protein fractions," J Nutr. Apr. 2004;134(4):996S-1002S. doi: 10.1093/in/134.4.996S. PMID: 15051860.
McSweeney, P., et al., editors, "Advanced Dairy Chemistry, vol. 1A, Proteins: Basic Aspects, 4th edition," Spinger, 2013, pp. 57-60, 216.217.
Armstrong, J., et al., "On the fractionation of beta-lactoglobulin and alpha-lactalbumin," Biochim Biophys Acta. Sep. 19, 1967;147(1):60-72. doi: 10.1016/0005-2795(67)90090-6.
New Jersey Department of Health, "Right to Know Hazardous substance Fact Sheet Common Name: Toluene," Apr. 2016.
Ke Chen, et al., "Prediction of protein crystallization using collocation of amino acid pairs," May 2007, Biochemical and Biophysical Research Communications 355(3):764-9, DOI:10.1016/j.bbrc.2007.02.040.
Mcmeekin Thomas L., et al: "The Hydration of β-Lactoglobulin Crystals", Journal of the American Chemical Society, vol. 64, No. 10, Oct. 1, 1942, pp. 2393-2398, XP093014909, Retrieved from the Internet: URL: https://pubs.acs.org/doi/pdf/10.1021/ja01262a049.
Briggs D R, et al: "Electrokinetics. XXVI. The Electroviscous Effect. III. In β-Lactoglobulin Systems. An Interpretation of the Meaning of Ko Values Obtained from Electroviscosity Data", The Journal of Physical Chemistry, vol. 48, No. 1, Jan. 1944, pp. 1-12, XP093014927, Retrieved from the Internet: URL: https://pubs.acs.org/doi/pdf/10.1021/150433a001.
World Health Organization, "Toluene," https://web.archive.org/web/20221007010454/https://inchem.org/documents/jecfa/jecmono/v16je24.htm (IPCS, INCHEM, Year: 2022).
Mate, J.I., Krochta, J.M., "β-Lactoglobulin Separation from Whey Protein Isolate on a Large Scale", 1994, Journal of Food Science, vol. 59, No. 5, pp. 1111-1114 (Year: 1994).
Kalamazoo Valley Community College, Chemistry 130, "Recrystallization Introduction", Sep. 2016, CHM 220, < https://web.archive.org/web/20160912162724/http://classes.kvcc.edu /chm220/Recrystallization/prelab/introduction.htm.> (Year: 2016).
Upadhyay, A.K., "How Whey Protein is Made", Nov. 2016, https://web.archive.org/web/20161026150835/http:IIus.myprotein.com/thezone/supplements/how-is-whey protein-made/ (Year: 2016).
Naofumi Kitabatake et al., Characteristics and Utilizaton of Process Whey Protein, Milk Science, 2001, vol. 50, No. 3, pp. 107-112. Translation of Introduction.
Tai et al.; "p-Lactoglobulin Influences Human Immunity and Promotes Cell Proliferation"; Nov. 13, 2016; National Library of Medicine; https://www.ncbi.nlm.nih.gov/pmc/articles/PMC5124466/ (Year: 2016).
Chatterton et al.; "Bioactivity of p-lactoglobulin and a-lactalbumin—Technological implications for processing"; Nov. 2006; International Dairy Journal; https://www.sciencedirect.com/science/article/pii/50958694606001439 (Year: 2006).
Agarwal, "Sodium content in retail Cheddar, Mozzarella, and process cheeses varies considerably in the United States", J. Dairy Sci . 2011, 94. pp. 1605-1615 (Year: 2011).
Eat This Much "100% Micellar Casein Protein", and "Micellar Casein Powder", https://www.eatthismuch.com/food/nutrition/100-micellar-casein-protein,1856289/, and https://www.eatthismuch.com/food/nutrition/micellar-casein-powder,2269279/ (Year: 2023).
Gorska et al., "The influence of trehalose-maltodextrin and lactose-maltodextrin matrices on thermal and sorption properties of spray-dried β-lactoglobulin-vitamin D3 complexes", 2013, J Therm Anal Calorim, vol. 112, pp. 429-436 (Year: 2013).
Tanford, C., et al., "Physico-Chemical Comparison of β-Lactoglobulins A and B", 1959, The Journal of Biological Chemistry, vol. 234, pp. 2874-2877 (Year: 1959).
Mankun Pang, Natural Pharmaceutical Chemistry Foundation, China Press of Traditional Chinese Medicine, Aug. 2013, pp. 43-45, Chapter 1.
Huffman LM, et al. Maximizing the value of milk through separation technologies. J Dairy Sci. Oct. 1999;82(10):2238-44. doi: 10.3168/jds.s0022-0302(99)75471-8.
Li Tiehong, et al., Dairy Industry, Functional Whey Protein Research and Application of Thermal Modification Technology—China Academic Journal Electronic Publishing House, 2009; DOI:10.16172/j.cnki.114768.2009.01.002.
Phan-Xuan, Tuan, et al. "Heat induced formation of beta-lactoglobulin microgels driven by addition of calcium ions" Food Hydrocolloids (2012), Sep. 19, 2012.
Phan-Xuan, Tuan, et al. "Tuning the Structure of Protein Particles and Gels with Calcium or Sodium Ions" ACS Publications, 2013 American Chemical Society, Apr. 25, 2013.
Saglam, Dilek, et al. "Relation between Gelation Conditions and the Physical Properties of Whey Protein Particles" Langmuir—ACS Pblications, 2012 American Chemical Society; published Apr. 3, 2012.
Taheri, Afsaneh, et al. "Rheological Characteristics of Soluble Cress Seed Mucilage and beta-Lactoglobulin Complexes with Salts Addition: Rheological Evidence of Structural Rearrangement" Gels 2023, 9, 485; published Jun. 13, 2023.
Xiu, Xiuling, et al. Aggregation Characteristics of beta-Lactoglubulin: a Review. China Academic Journal Electronic Publishing House, Jul. 28, 2014—translated Abstract.
H.F. Alomirah, et al., "Separation and characterization of beta-lactoglobulin and alpha-lactalbumin from whey and whey protein preparations," May 2004International Dairy Journal 14(5):411-419, DOI:10.1016/j.idairyj.2003.09.006.
Hans Bertelsen, Expert Declaration for European Patent Application No. EP3858145A1, Aug. 2, 2023.
J.N. de Wit, "Effects of ionic strength on the solubility of whey protein products. A colloid chemical approach," Food Hydrocolloids, vol. 10, Issue 2, Apr. 1996, pp. 143-149.
Robertson, D. L., "Supersaturated Solution", 2010, https://home.miracosta.edu/dlr/info/super_saturation.htm (Year: 2010).
Bateman L, et al., "In vitro digestion of beta-lactoglobulin fibrils formed by heat treatment at low pH." J Agric Food Chem. Sep. 8, 2010; 58(17):9800-8. doi: 10.1021/jf101722t. PMID: 20684554.

\* cited by examiner

120 °C/20s  120 °C/20s  75 °C/15s  75 °C/15s
BLG pH 3.7  WPI-B pH 3.7  WPI-B pH 3.7  BLG pH 3.7

WPI-B  WPI-B  WPI-B  WPI-B  WPI-B  WPI-B  BLG
pH 3.0  pH 3.3  pH 3.4  pH 3.5  pH 3.6  pH 3.7  pH3.7

WPI-B pH 3.0    WPI-B pH 3.3    WPI-B pH 3.4    WPI-B pH 3.5    WPI-B pH 3.6    WPI-B pH 3.7    BLG pH3.7

WPI-B pH 3.7    BLG pH3.9

15% BLG    6% WPI-A
pH 3.7     pH 3.7 pH 4.2   pH 4.5

BLG (6%)    SPI (6%)
pH 3.7      pH 3.7
75 °C/5 min  75 °C/5 min

BLG (6%)    SPI (6%)
pH 3.7      pH 3.7
120 °C/20s  120 °C/20s

ACIDIC BETA-LACTOGLOBULIN BEVERAGE PREPARATION

FIELD OF THE INVENTION

The present invention pertains to a new packaged, heat-treated beverage preparation having a pH in the range of 2.0-4.7. The invention furthermore relates to a method of producing a packaged, heat-treated beverage preparation and to different uses of the packaged, heat-treated beverage preparation.

BACKGROUND

Nutritional supplements comprising whey proteins are commonly used for muscle synthesis, for weight control and for maintaining muscle and bodyweight. Nutritional supplements are targeted towards different kinds of consumers, e.g. sportsmen/women, athletes, children, elderly people and patients with or at risk of malnutrition, and/or with increased protein needs. Whey proteins can be isolated from milk serum or whey. Whey typically comprises a mixture of beta-lactoglobulin (BLG), alpha-lactalbumin (ALA), serum albumin and immunoglobulins, of which BLG is the most dominant. Whey protein concentrates (WPC) thus comprise a mixture of these proteins. Whey protein isolates (WPI) contain less fat and lactose than WPC. Beverages comprising whey proteins are well known, such as acidic heat-treated beverages comprising whey proteins.

Etzel 2004 (Etzel, M. R., 2004, Manufacture and use of dairy protein fraction. American Society for Nutritional Science, pp. 996-1002) describes a beverage containing 2.5 wt % WPI at pH 2-7. They found that beverages that had been subjected to a thermal processing could only be obtained if an antiaggregant was added.

WO 2018/115,520 A1 discloses a method of producing edible isolated beta-lactoglobulin compositions and/or compositions containing crystallised beta-lactoglobulin based on crystallisation of BLG in salting-in mode. The crystallised BLG may subsequently be separated from the remaining mother liquour.

WO 2004/049,819 A2 discloses a method for improving the functional properties of globular proteins, comprising the steps of providing a solution of one or more globular proteins, in which solution the protein(s) is/are at least partially aggregated in fibrils; and performing one or more of the following steps in random order: increasing the pH; increasing the salt concentration; concentrating the solution; and changing the solvent quality of the solution. Preferably, the solution of the one or more globular protein is provided by heating at a low pH or the addition of a denaturing agent. Disclosed is also the protein additive thus obtained, the use thereof for food and non-food applications and to the food and non-food products containing the protein additive.

WO 2014/055,830 A1 discloses shelf-stable, clear liquid nutritional compositions having a pH ranging from 2.5 to 4.6 and comprising water; at least one source of EGCg in an amount sufficient to provide 200-1700 mg/L of EGCg; and at least one source of protein in an amount sufficient to provide 25-45 g/L of total protein. The shelf-stable, clear liquid nutritional compositions lose no more than 20% by weight solids of the EGCg content present in the initial formulation of the compositions to epimerization, degradation, or both epimerization and degradation during heat sterilization. In certain embodiments, the loss of EGCg is exhibited by the amount of epimerization product GCg present in the shelf-stable, clear liquid nutritional composition following heat sterilization. Methods for preparing the shelf-stable, clear liquid nutritional compositions are also disclosed.

WO 2011/112,695 A1 discloses nutritional compositions and methods of making and using the nutritional compositions. The nutritional compositions comprise whey protein micelles and leucine and provide a sufficient amount of leucine to improve protein synthesis in humans, while also maintaining a low-viscosity fluid matrix and acceptable organoleptic properties.

WO 2011/051,436 A1 discloses at least partially transparent compositions intended for human or animal consumption and to the packaging of such compositions. One embodiment of the present invention relates to an at least partially transparent container containing an at least partially transparent aqueous non-alcoholic composition. The container comprises at least one polarizer that makes liquid crystals present in the composition visible.

WO 2010/037,736 A1 discloses isolation of whey proteins and the preparation of a whey product and a whey isolate. In particular the present invention relates to the isolation of a β-lactoglobulin product and the isolation of an α-enriched whey protein isolate from whey obtained from an animal. The α-enriched whey protein isolate provided by the present invention is besides from being low in β-lactoglobulin also high in α-lactalbumin and immunoglobulin G.

FR 2 296 428 discloses protein compositions for dietetic and therapeutic use based on lactoserum proteins obtained by any known separation process. The compositions can be used for the treatment or prophylaxis of digestive disorders in infants and adults (e.g. diarrhoea), to increase resistance to intestinal infections, and to treat certain metabolic disorders (e.g. hyperphylalaninaemia). They can also be used dermatologically or cosmetically, and can form part of a low-protein diet.

SUMMARY OF THE INVENTION

The present inventors have observed that organoleptic characteristics such as astringency and mouthfeel play a significant role in the selection of liquid nutritional beverages by consumers. Some of the challenges in incorporating whey proteins in acidic heat-treated beverages are formation of unstable precipitate that sediment in the beverage, high viscosity or even gel-formation, and unpleasant taste due to high degree of astringency and/or a drying mouthfeeling.

An object of the present invention is to provide an acidic, packaged, heat-treated beverage preparation comprising whey protein and having improved organoleptic and/or visual properties.

Another object of the invention is to provide a high protein beverage with a low viscosity, a pleasant taste, optionally with low astringency, and which may either be transparent or opaque.

The present inventors have now discovered that such packaged, heat-treated beverages can be provided within a broad acidic pH range up to and including pH 4.7, while still having a low viscosity and optionally also a low level of astringency and drying mouthfeel. The invention provides both beverages that are transparent and beverages that are opaque but stable.

Thus, an aspect of the invention pertains to a packaged, heat-treated beverage preparation having a pH in the range of 2.0-4.7, the beverage comprising a total amount of protein of 2 to 45% w/w relative to the weight of the beverage, wherein at least 85% w/w of the protein is BLG, and optionally, sweetener, sugar polymers and/or flavour.

Another aspect of the invention pertains to a method of producing a packaged, heat-treated beverage preparation having a pH in the range of 2.0-4.7, comprising the following steps:

a) Providing a liquid solution comprising:
   a total amount of protein of 2 to 45% by weight, wherein at least 85% of the protein is BLG
   optionally, sweetener, sugar polymers and/or flavour
b) packaging the liquid solution,
   wherein the liquid solution of step a) and/or the packaged liquid solution of step b) is subjected to a heat-treatment comprising at least pasteurisation.

Yet an aspect of the invention pertains to use of a protein solution comprising a total amount of protein of 2 to 45% w/w relative to the weight of the solution, wherein at least 85 w/w % of the protein is BLG for controlling the turbidity of a heat-treated acidic beverage preparation having a pH in the range of 2.0-4.7.

Still another aspect of the invention pertains to use of a protein solution comprising a total amount of protein of 2 to 45% w/w relative to the weight of the solution, wherein at least 85 w/w % of the protein is BLG for controlling the astringency of a heat-treated acidic beverage preparation having a pH in the range of 2.0-4.7.

A further aspect of the invention pertains to a packaged, heat-treated beverage preparation according to the invention for use in a method for the treatment of diseases associated with protein malabsorption.

A further aspect of the invention pertains to use of a packaged, heat-treated beverage preparation according to the invention as a dietary supplement.

DETAILED DESCRIPTION

Definitions

Figure 1:
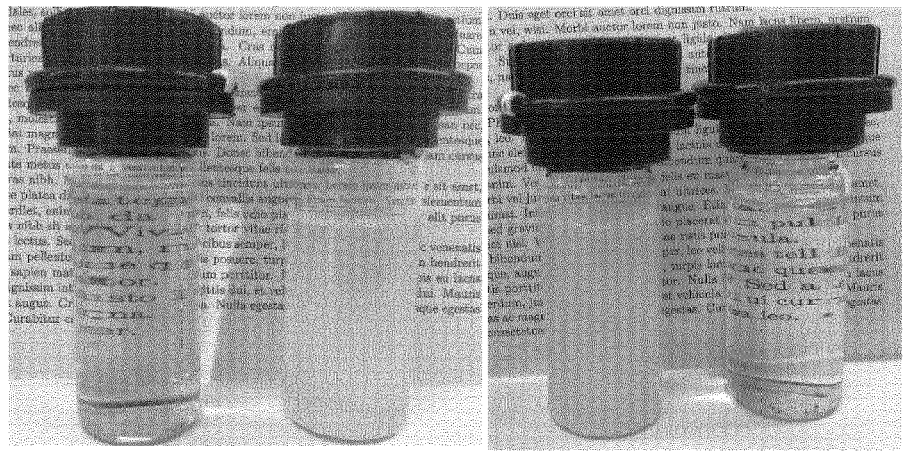
FIG. 1 shows images of BLG and WPI beverages having a pH of 3.7 and a protein content of 6% w/w, heat-treated at 120° C. for 20 seconds or 75° C. for 15 seconds.

In the context of the present invention, the term "beta-lactoglobulin" or "BLG" pertains to beta-lactoglobulin from mammal species, e.g. in native, unfolded and/or glycosylated forms and includes the naturally occurring genetic variants. The term furthermore includes aggregated BLG, precipitated BLG and crystalline BLG. When referring to the amount of BLG reference is made to the total amount of BLG including aggregated BLG. The total amount of BLG is determined according to Example 1.31. The term "aggregated BLG" pertains to BLG which is at least partially unfolded and which furthermore has aggregated with other denatured BLG molecules and/or other denatured whey proteins, typically by means of hydrophobic interactions and/or covalent bonds.

BLG is the most predominant protein in bovine whey and milk serum and exists in several genetic variants, the main ones in cow milk being labelled A and B. BLG is a lipocalin protein, and can bind many hydrophobic molecules, suggesting a role in their transport. BLG has also been shown to be able to bind iron via siderophores and might have a role in combating pathogens. A homologue of BLG is lacking in human breast milk.

Bovine BLG is a relatively small protein of approx. 162 amino acid residues with a molecular weight of approx. 18.3-18.4 kDa. Under physiological conditions, it is predominantly dimeric, but dissociates to a monomer below about pH 3, preserving its native state as determined using Nuclear Magnetic Resonance spectroscopy. Conversely, BLG also occurs in tetrameric, octameric and other multimeric aggregation forms under a variety of natural conditions.

In the context of the present invention, the term "non-aggregated beta-lactoglobulin" or "non-aggregated BLG" also pertains to beta-lactoglobulin from mammal species, e.g. in native, unfolded and/or glycosylated forms and includes the naturally occurring genetic variants. However, the term does not include aggregated BLG, precipitated BLG or crystallised BLG. The amount or concentration of non-aggretated BLG is determined according to Example 1.6.

The percentage of non-aggregated BLG relative to total BLG is determined by calculate $(m_{total\ BLG} - m_{non-aggregate\ BLG})/m_{total\ BLG} * 100\%$. $m_{total\ BLG}$ is the concentration or amount of BLG determined according to Example 1.31 and $m_{non-aggregated\ BLG}$ is the concentration or amount of non-aggregated BLG determined according to Example 1.6.

In the context of the present invention, the term "crystal" pertains to a solid material whose constituents (such as atoms, molecules or ions) are arranged in a highly ordered microscopic structure, forming a crystal lattice that extends in all directions.

In the context of the present invention, the term "BLG crystal" pertains to protein crystals that primarily contain non-aggregated and preferably native BLG arranged in a highly ordered microscopic structure, forming a crystal lattice that extends in all directions. The BLG crystals may e.g. be monolithic or polycrystalline and may e.g. be intact crystals, fragments of crystals, or a combination thereof. Fragments of crystal are e.g. formed when intact crystals are subjected to mechanical shear during processing. Fragments of crystals also have the highly ordered microscopic structure of crystal but may lack the even surface and/or even edges or corners of an intact crystal. See e.g. FIG. 18 of PCT application no. PCT/EP2017/084553 for an example of many intact BLG crystals and FIG. 13 PCT application no. PCT/EP2017/084553 for an example of fragments of BLG crystals. In both cases, the BLG crystal or crystal fragments can be identified visually as well-defined, compact and coherent structures using light microscopy. BLG crystal or crystal fragments are often at least partially transparent. Protein crystals are furthermore known to be birefringent and this optical property can be used to identify unknown particles having a crystal structure. Non-crystalline BLG aggregates, on the other hand, often appear as poorly defined, non-transparent, and as open or porous lumps of irregular size.

In the context of the present invention, the term "crystallise" pertains to the formation of protein crystals. Crystallisation may e.g. happen spontaneously or be initiated by the addition of crystallisation seeds.

In the context of the present invention, the term "edible composition" pertains to a composition that is safe for human consumption and use as a food ingredient and that does not contain problematic amounts of toxic components, such as toluene or other unwanted organic solvents.

In the context of the present invention, the term "ALA" or "alpha-lactalbumin" pertains to alpha-lactalbumin from mammal species, e.g. in native and/or glycosylated forms and includes the naturally occurring genetic variants. The term furthermore includes aggregated ALA and precipitated BLG. When referring to the amount of ALA reference is made to the total amount of ALA including e.g. aggregated ALA. The total amount of ALA is determined according to Example 1.31. The term "aggregated ALA" pertains to ALA which typically is at least partially unfolded and which furthermore has aggregated with other denatured ALA molecules and/or other denatured whey proteins, typically by means of hydrophobic interactions and/or covalent bonds.

Alpha-lactalbumin (ALA) is a protein present in the milk of almost all mammalian species. ALA forms the regulatory subunit of the lactose synthase (LS) heterodimer and β-1, 4-galactosyltransferase (beta4Gal-T1) forms the catalytic component. Together, these proteins enable LS to produce lactose by transferring galactose moieties to glucose. One of the main structural differences with beta-lactoglobulin is that ALA does not have any free thiol group that can serve as the starting-point for a covalent aggregation reaction.

In the context of the present invention, the term "non-aggregated ALA" also pertains to ALA from mammal species, e.g. in native, unfolded and/or glycosylated forms and includes the naturally occurring genetic variants. However, the term does not include aggregated ALA or precipitated ALA. The amount or concentration of non-aggretated BLG is determined according to Example 1.6.

The percentage of non-aggregated ALA relative to total ALA is determined by calculate $(m_{total\ ALA} - m_{non-aggregate\ ALA})/m_{total\ ALA} * 100\%$. $m_{total\ ALA}$ is the concentration or amount of ALA determined according to Example 1.31 and $m_{non-aggregated\ ALA}$ is the concentration or amount of non-aggregated ALA determined according to Example 1.6.

In the context of the present invention, the term "caseinomacropeptide" or "CMP" pertains to the hydrophilic peptide, residue 106-169, originated from the hydrolysis of "κ-CN" or "kappa-casein" from mammal species, e.g. in native and/or glycosylated forms and includes the naturally occurring genetic variants, by an aspartic proteinase, e.g. chymosin.

In the context of the present invention, the term "BLG isolate" means a composition that contains BLG in an amount of at least 85% w/w relative to total protein. A BLG isolate preferably has a total protein content of a least 30% w/w, and preferably at least 80% w/w relative to total solids.

In the context of the present invention, the term "BLG isolate powder" pertains to a BLG isolate in powder form and preferably a free-flowing powder.

In the context of the present invention, the term "BLG isolate liquid" pertains to a BLG isolate in liquid form and preferably an aqueous liquid.

The term "whey" pertains to the liquid phase that is left after the casein of milk has been precipitated and removed. Casein precipitation may e.g. be accomplished by acidification of milk and/or by use of rennet enzyme. Several types of whey exist, such as "sweet whey", which is the whey product produced by rennet-based precipitation of casein, and "acid whey" or "sour whey", which is the whey product produced by acid-based precipitation of casein. Acid-based precipitation of casein may e.g. be accomplished by addition of food acids or by means of bacterial cultures.

The term "milk serum" pertains to the liquid which remains when casein and milk fat globules have been removed from milk, e.g. by microfiltration or large pore ultrafiltration. Milk serum may also be referred to as "ideal whey".

The term "milk serum protein" or "serum protein" pertains to the protein which is present in the milk serum.

In the context of the present invention, the term "whey protein" pertains to protein that is found in whey or in milk serum. Whey protein may be a subset of the protein species found in whey or milk serum, and even a single whey protein species or it may be the complete set of protein species found in whey or/and in milk serum.

In the context of the present invention, the main non-BLG proteins of a standard whey protein concentrate from sweet whey are ALA, CMP, bovine serum albumin, immunoglobulin, osteopontin, lactoferrin, and lactoperoxidase. In the context of the present invention, the weight percentages of the main non-BLG whey proteins of a standard whey protein concentrate from sweet whey are:

ALA in an amount of 18% w/w relative to total protein,
CMP in an amount of 18% w/w relative to total protein,
BSA in an amount of 4% w/w relative to total protein,
Casein species in an amount of 5% w/w relative to total protein,
Immunoglobulin in an amount of 6% w/w relative to total protein,
Osteopontin in an amount of 0.5% w/w relative to total protein,
Lactoferrin in an amount of 0.1% w/w relative to total protein, and
Lactoperoxidase in an amount of 0.1% w/w relative to total protein.

In the context of the present invention the term "mother liquor" pertains to the whey protein solution that remains after BLG has been crystallised and the BLG crystals have be at least partially removed. The mother liquor may still contain some BLG crystals but normally only small BLG crystals that have escaped the separation.

In the context of the present invention, the term casein pertains to casein protein found in milk and encompasses both native micellar casein as found in raw milk, the individual casein species, and caseinates.

In the context of the present invention, a liquid which is "supersaturated" or "supersaturated with respect to BLG" contains a concentration of dissolved, non-aggregated BLG which is above the saturation point of non-aggregated BLG in that liquid at the given physical and chemical conditions. The term "supersaturated" is well-known in the field of crystallisation (see e.g. Gerard Coquerela, "Crystallization of molecular systems from solution: phase diagrams, supersaturation and other basic concepts", Chemical Society Reviews, p. 2286-2300, Issue 7, 2014) and supersaturation can be determined by a number of different measurement techniques (e.g. by spectroscopy or particle size analysis). In the context of the present invention, supersaturation with respect to BLG is determined by the following procedure.

Procedure for Testing Whether a Liquid at a Specific Set of Conditions is Supersaturated with Respect to BLG:

a) Transfer a 50 ml sample of the liquid to be tested to a centrifuge tube (VWR Catalogue no. 525-0402) having a height of 115 mm, an inside diameter of 25 mm and a capacity of 50 mL. Care should be taken to keep the sample and subsequent fractions thereof at the original physical and chemical conditions of the liquid during steps a)-h).

b) The sample is immediately centrifuged at 3000 g for 3.0 minutes with max. 30 seconds acceleration and max 30 seconds deceleration.

c) Immediately after the centrifugation, transfer as much as possible of the supernatant (without disturbing the pellet if a pellet has formed) to a second centrifuge tube (same type as in step a)

d) Take a 0.05 mL subsample of the supernatant (subsample A)

e) Add 10 mg of BLG crystals (at least 98% pure, non-aggregated BLG relative to total solids) having a particle size of at most 200 micron to a second centrifuge tube and agitate the mixture.

f) Allow the second centrifuge tube to stand for 60 minutes at the original temperature.

g) Immediately after step f), centrifuge the second centrifuge tube at 500 g for 10 minutes and then take another 0.05 mL subsample of the supernatant (subsample B).

h) Recover the centrifugation pellet of step g) if there is one, resuspend it in milliQ water and immediately inspect the suspension for presence of crystals that are visible by microscopy.

i) Determine the concentration of non-aggregated BLG in subsamples A and B using the method outlined in Example 1.6—the results are expressed as % BLG w/w relative to the total weight of the subsamples. The concentration of non-aggregated BLG of subsample A is referred to as $c_{BLG, A}$, and the concentration of non-aggregated BLG of subsample B is referred to as $c_{BLG, B}$.

j) The liquid from which the sample of step a) was taken was supersaturated (at the specific conditions) if $c_{BLG, B}$ is lower than $c_{BLG, A}$ and if crystals are observed in step i).

In the context of the present invention, the terms "liquid" and "solution" encompass both compositions that are free of particulate matter and compositions that contain a combination of liquid and solid and/or semi-solid particles, such as e.g. protein crystals or other protein particles. A "liquid" or a "solution" may therefore be a suspension or even a slurry. However, a "liquid" and "solution" are preferably pumpable.

In the context of the present invention, the terms "whey protein concentrate" (WPC) and "serum protein concentrate" (SPC) pertain to dry or aqueous compositions which contain a total amount of protein of 20-89% w/w relative to total solids.

A WPC or an SPC preferably contains:
20-89% w/w protein relative to total solids,
15-70% w/w BLG relative to total protein,
8-50% w/w ALA relative to total protein, and
0-40% w/w CMP relative to protein.

Alternatively, but also preferred, a WPC or an SPC may contain:
20-89% w/w protein relative to total solids,
15-90% w/w BLG relative to total protein,
4-50% w/w ALA relative to total protein, and
0-40% w/w CMP relative to protein.

Preferably, a WPC or an SPC contains:
20-89% w/w protein relative to total solids,
15-80% w/w BLG relative to total protein,
4-50% w/w ALA relative to total protein, and
0-40% w/w CMP relative to protein.

More preferably a WPC or an SPC contains:
70-89% w/w protein relative to total solids,
30-90% w/w BLG relative to total protein,
4-35% w/w ALA relative to total protein, and
0-25% w/w CMP relative to protein.

SPC typically contain no CMP or only traces of CMP.

The terms "whey protein isolate" (WPI) and "serum protein isolate" (SPI) pertain to dry or aqueous compositions which contain a total amount of protein of 90-100% w/w relative to total solids.

A WPI or an SPI preferably contains:
90-100% w/w protein relative to total solids,
15-70% w/w BLG relative to total protein, 8-50% w/w ALA relative to total protein, and
0-40% w/w CMP relative to total protein.

Alternatively, but also preferred, a WPI or an SPI may contain:
90-100% w/w protein relative to total solids,
30-95% w/w BLG relative to total protein,
4-35% w/w ALA relative to total protein, and
0-25% w/w CMP relative to total protein.

More preferably a WPI or an SPI may contain:
90-100% w/w protein relative to total solids,
30-90% w/w BLG relative to total protein,
4-35% w/w ALA relative to total protein, and
0-25% w/w CMP relative to total protein.

SPI typically contain no CMP or only traces of CMP.

In the context of the present invention, the term "additional protein" means a protein that is not BLG. The additional protein that is present in the whey protein solution typically comprises one or more of the non-BLG proteins that are found in milk serum or whey. Non-limiting examples of such proteins are alpha-lactalbumin, bovine serum albumin, immunoglobulines, caseinomacropeptide (CMP), osteopontin, lactoferrin, and milk fat globule membrane proteins.

The terms "consists essentially of" and "consisting essentially of" mean that the claim or feature in question encompasses the specified materials or steps and those that do not materially affect the basic and novel characteristic(s) of the claimed invention.

In the context of the present invention, the phrase "Y and/or X" means "Y" or "X" or "Y and X". Along the same line of logic, the phrase "$n_1$, $n_2$, . . . , $n_{i-1}$, and/or $n_i$" means "$n_1$" or "$n_2$" or . . . or "$n_{i-1}$" or "$n_i$" or any combination of the components: $n_1$, $n_2$, . . . $n_{i-1}$, and $n_i$.

In the context of the present invention, the term "dry" or "dried" means that the composition or product in question comprises at most 10% w/w water, preferably at most 6% w/w and more preferably even less.

In the context of the present invention, the term "physical microbial reduction" pertains to physical interaction with a composition which results in reduction of the total amount of viable microorganisms of the composition. The term does not encompass addition of chemicals that result in killing of microorganisms. The term furthermore does not encompass the heat exposure to which the atomized droplets of liquid are exposed to during spray-drying but include possible pre-heating prior to spray-drying.

In the context of the present invention, the pH of a powder refers to the pH of 10 g of the powder mixed into 90 g demineralised water and is measured according to Example 1.16.

In the context of the present invention, the weight percentage (% w/w) of a component of a certain composition, product, or material means the weight percentage of that component relative to the weight of the specific composition, product, or material unless another reference (e.g total solids or total protein) is specifically mentioned.

In the context of the present invention, the process step "concentration" and the verb "concentrate" pertain to concentration of protein and encompass both concentration of protein on total solids basis and concentration of protein on a total weight basis. This means e.g. that concentration does not necessarily require that the absolute concentration w/w of protein of a composition increases as long at the content of protein increases relative to total solids.

In the context of the present invention, the term "weight ratio" between component X and component Y means the value obtained by the calculation mx/my wherein mx is the amount (weight) of components X and my is the amount (weight) of components Y.

In the context of the present invention, the terms "at least pasteurisation" and "at least pasteurised" pertain to a heat-treatment which has microbial killing effect equal to or higher than a heat-treatment of 70 degrees C. for 10 seconds. The reference for determining the bacteria killing effect is *E. coli* O157:H7.

In the context of the present invention, the term "whey protein feed" pertains to whey protein source from which the liquid BLG isolate is derived. The whey protein feed has a lower content of BLG relative to total protein than the liquid BLG isolate and is typically a WPC, a WPI, an SPC or an SPI.

In the context of the present invention, the term "BLG-enriched composition" pertains to the BLG-enriched composition resulting from isolating BLG from the whey protein feed. The BLG-enriched composition typically comprises the same whey proteins as the whey protein feed but BLG is present in significantly higher concentration relative to total protein than in whey protein feed. The BLG-enriched composition may e.g. be prepared from the whey protein feed by chromatography, protein crystallisation and/or membrane-based protein fractionation. The BLG-enriched composition comprises BLG in an amount of at least 85% w/w relative to total protein, and preferably at least 90% w/w. In some cases the BLG-enriched composition can be used directly as the liquid BLG isolate. However, often additional processing is required to convert the BLG-enriched composition to the liquid BLG isolate.

In the context of the present invention, the term "whey protein solution" is used to describe the special aqueous whey protein composition that is supersaturated with respect to BLG in salting-in mode and useful for preparing BLG crystals.

In the context of the present invention, the term "sterile" means that the sterile composition or product in question does not contain any viable microorganisms and therefore is devoid of microbial growth during storage at room temperature. A composition that has been sterilised is sterile.

When a liquid, such as a beverage preparation, is sterilized and packaged aseptically in a sterile container it typically has a shelf life of at least six months at room temperature. The sterilization treatment kills spores and microorganisms that could cause spoilage of the liquid.

In the context of the present invention the term "energy content" means the total content of energy contained in a food product. The energy content can be measured in kilojoule (kJ) or kilo calories (kcal) and are referred to as calories per amount of food product, e.g. kcal per 100 gram of the food product. One example is a beverage having an energy content of 350 kcal/100 gram of the beverage.

The total energy content of a food product includes the energy contribution from all the macronutrients present in the food product, e.g. energy from protein, lipid and carbohydrate. The distribution of energy from the macronutrients in the food product can be calculated based on the amount of the macronutrients in the food product and the contribution of the macronutrient to the total energy content of the food product. The energy distribution can be stated as energy percent (E %) of the total energy content of the food product. For example for a beverage comprising 20 E % protein, 50 E % carbohydrate and 30 E % lipid, this means that 20% of the total energy comes from protein, 50% of the total energy comes from carbohydrate and 30% of the total energy comes from fat (lipid).

In the context of the present invention the term "nutritionally complete nutritional supplement" is understood as a food product comprising protein, lipid and carbohydrate and further comprising vitamins, minerals and trace elements, where the beverage has a nutrient profile matching a complete and healthy diet.

In the context of the present invention the term "nutritionally incomplete supplement" means food products comprising one or more macro nutrients and optionally further comprising vitamins, minerals and trace elements. A nutritionally incomplete beverage may comprise protein as the only nutrient or may for example comprise protein and a carbohydrate.

The term "food for special medical purposes (FSMP)" or "medical food" are food products for oral ingestion or tube feeding, which are used for specific medical disorders, diseases or conditions for which there are distinctive nutritional requirements and which are used under medical supervision. A medical food can be a nutritionally complete supplement/beverage or an nutritionally incomplete supplement/beverage.

The term "nutrient" means a substance used by an organism to survive, grow and reproduce. Nutrients can be either macronutrients or micronutrients. Macronutrients are nutrients that provide energy when consumed e.g. protein, lipid and carbohydrate. Micronutrients are nutrients like vitamins, minerals and trace elements.

The term "nutrient" means a substance used by an organism to survive, grow and reproduce. Nutrients can be either macronutrients or micronutrients. Macronutrients are nutrient that provide energy when consumed e.g. protein, lipid and carbohydrate. Micronutrients are nutrients are vitamins, minerals and trace elements.

By the term "instant beverage powder" or "instant beverage powder product" is meant a powder which can be converted to a liquid beverage by addition of a liquid, such as water.

In the context of the present invention the term "beverage" and the terms "beverage preparation" and "preparation" used as a substantive relate to any water-based liquid which can be ingested as a drink, e.g. by pouring, sipping or tube-feeding.

In the context of the present invention the term "protein fraction" relates to proteins of the composition in question e.g. the proteins of a powder or a beverage preparation.

In the context of the present invention the term "astringency" relates to a mouthfeeling. Astringency feels like a contraction of cheek muscles and results in increased saliva production. Thus, astringency is not a taste as such, but a physical mouth feeling and time-dependent feeling in the mouth.

In the context of the present invention the term "drying mouthfeeling" relates to a feeling in the mouth, it feels like a drying of the mouth and teeth and results in minimization of the saliva production.

Thus drying mouthfeeling is not a taste as such, but a physical mouth feeling and time-dependent feeling in the mouth.

In the context of the present invention the term "minerals" as used herein, unless otherwise specified, refers to any one of major minerals, trace or minor minerals, other minerals, and combinations thereof. Major minerals include calcium, phosphorus, potassium, sulfur, sodium, chlorine, magnesium. Trace or minor minerals include iron, cobalt, copper, zinc, molybdenum, iodine, selenium, manganese and other minerals include chromium, fluorine, boron, lithium, and strontium.

In the context of the present invention the terms "lipid", "fat", and "oil" as used herein unless otherwise specified, are used interchangeably to refer to lipid materials derived or processed from plants or animals. These terms also include synthetic lipid materials so long as such synthetic materials are suitable for human consumption.

In the context of the present invention the term "transparent" encompasses a beverage preparation having a visibly clear appearance and which allows light to pass and through which distinct images appear. A transparent beverage has a turbidity of at most 200 NTU.

In the context of the present invention the terms "opaque" encompasses a beverage preparation having a visibly unclear appearance and it has a turbidity of more than 200 NTU.

An aspect of the invention pertains to a packaged, heat-treated beverage preparation having a pH in the range of 2.0-4.7, the beverage comprising
  a total amount of protein of 2 to 45% w/w relative to the weight of the beverage, wherein at least 85% w/w of the protein is BLG, and
  optionally, sweetener, sugar polymers and/or flavour.

Packaged, heat-treated beverage preparations comprising at least 85% w/w of the protein are very beneficial for a number of reasons. The high BLG content in acidic beverages also allow for increasing the pH range and decreasing the heating temperature while still maintaining clarity and lack of colour, this is possible even when a high protein concentration is applied. This means that transparent, colourless high protein beverages can be produced at a less acidic pH level than can be done with a traditional WPI.

It was surprisingly found that the BLG beverages have a lower astringency, drying mouthfeeling, sourness, whey aroma and citric acid flavour compared to traditional acidic WPI beverages.

Another advantage of the present invention and the expanded pH range is that milky beverages can be produced having a high turbidity, low viscosity, while still being white and not becoming yellowish and still being stable.

In some preferred embodiments of the packaged, heat-treated beverage preparation of the invention at least 85% w/w of the protein is BLG. Preferably, at least 88% w/w of the protein is BLG, more preferably at least 90% w/w, even more preferably at least 91% w/w, and most preferably at least 92% w/w of the protein is BLG.

Even higher relative amounts of BLG are both feasible and desirable thus in some preferred embodiments of the invention, at least 94% w/w of the protein of the packaged, heat-treated beverage preparation is BLG, more preferably at least 96% w/w of the protein is BLG, even more preferably at least 98% w/w of the protein is BLG, and most preferably approx. 100% w/w.

For example, the packaged, heat-treated beverage preparation preferably comprises BLG in an amount of at least 97.5% w/w relative to total protein, preferably at least 98.0% w/w, more preferably at least 98.5% w/w, even more preferably at least 99.0%, and most preferably BLG in an amount of at least 99.5% w/w relative to total protein, such as approx. 100.0% w/w relative to total protein.

In some preferred embodiments of the invention, the packaged, heat-treated beverage preparation is at least pasteurised.

In some preferred embodiments of the invention, the packaged, heat-treated beverage preparation is sterilised, and hence sterile.

In some preferred embodiments of the invention, the native conformation of the proteins is maintained. The native conformation of the proteins is preferably maintained by using a heat-treatment that does not result in irreversible changes in protein conformation of at least BLG, and preferably of all the proteins.

The degree of protein nativeness depends on a number of factors including protein concentration, pH, temperature and time of heat-treatment.

The intrinsic tryptophan fluorescence emission ratio R=I330/I350 is a measure of protein nativity. When R is at least 1.11 the native conformation is predominant, while when R is less than 1.11 an at least partial unfolding and aggregration is predominant. A method for analyzing the intrinsic tryptophan fluorescence is described in example 1.1.

The inventors have found that an intrinsic tryptophan fluorescence emission ratio R=I330/I350 of at least 1.11 can be obtained for heat-treated, high protein beverages, while still having a low viscosity, and being transparent. This is possible even when the protein fraction and/or beverage preparation is subjected to a heat-treatment corresponding to pasteurization (e.g. to a temperature below 90° C.).

Therefore, in some preferred embodiments of the invention, the protein fraction of the beverage preparation has an intrinsic tryptophan fluorescence emission ratio (I330 nm/I350 nm) of at least 1.11, thus indicating that the proteins are in a native state.

In some preferred embodiments of the invention, the protein fraction of the beverage preparation has an intrinsic tryptophan fluorescence emission ratio (I330 nm/I350 nm) of at least 1.12, preferably at least 1.13, more preferably at least 1.15, even more preferably at least 1.17, and most preferably at least 1.19.

It may be particularly preferred that the protein fraction of the beverage preparation or the beverage preparation as such has an intrinsic tryptophan fluorescence emission ratio (I330 nm/I350 nm) of at least 1.15, more preferably at least 1.16, and even more preferably at least 1.17.

In some preferred embodiments of the invention, the packaged, heat-treated beverage preparation comprising the protein fraction and optionally other ingredients, such as lipids, carbohydrates, vitamins, minerals, food acids or emulsifiers, have a tryptophan fluorescence emission ratio of at least 1.11.

Therefore, in some preferred embodiments of the invention, the beverage preparation has an intrinsic tryptophan fluorescence emission ratio (I330 nm/I350 nm) of at least 1.11.

In some preferred embodiments of the invention, the heat-treated beverage preparation has an intrinsic tryptophan fluorescence emission ratio (I330 nm/I350 nm) of at least 1.12, preferably at least 1.13, more preferably at least 1.15, even more preferably at least 1.17, and most preferably at least 1.19.

In some preferred embodiments of the invention, the proteins are denatured or at least partly denatured.

Therefore, in some preferred embodiments of the invention, the protein fraction of the beverage preparation has an intrinsic tryptophan fluorescence emission ratio (I330 nm/I350 nm) of less than 1.11, thus indicating that the proteins are at least partially unfolded and that aggregation is predominant.

In some embodiments of the invention, the heat-treated beverage preparation has an intrinsic tryptophan fluorescence emission ratio (I330 nm/I350 nm) of less than 1.10, more preferably less than 1.08, even more preferably less than 1.05 and most preferably less than 1.00.

However, in other preferred embodiments of the invention, the protein fraction of the heat-treated beverage preparation has an intrinsic tryptophan fluorescence emission ratio (I330 nm/I350 nm) of less than 1.15, more preferably less than 1.14, even more preferably less than 1.13 and most preferably less than 1.12.

In some preferred embodiments of the invention, the heat-treated beverage preparation has an intrinsic tryptophan fluorescence emission ratio (I330 nm/I350 nm) of less than 1.15, more preferably less than 1.14, even more preferably less than 1.13 and most preferably less than 1.12.

The beverage preparation may in addition to the protein fraction optionally also comprise other food additives, such as lipids, carbohydrates, vitamins, minerals, food acids or emulsifiers etc. In some preferred embodiments of the invention, the beverage preparation has an intrinsic tryptophan fluorescence emission ratio (I330 nm/I350 nm) of less than 1.11, thus indicating that the proteins are at least partially unfolded and that aggregation is predominant.

In some preferred embodiments of the invention, the heat-treated beverage preparation has an intrinsic tryptophan fluorescence emission ratio (I330 nm/I350 nm) of less than 1.10, more preferably less than 1.08, even more preferably less than 1.05 and most preferably less than 1.00.

Protein denaturation may also be described by another analysis method than by Tryptophan fluorescence. This method is described in example 1.3.

In some preferred embodiments of the invention, the protein fraction of the packaged, heat-treated beverage preparation has a degree of protein denaturation of at most 10%. Preferably at most 8%, more preferably at most 5%, even more preferably at most 3%, even more preferably at most 1%, and most preferably at most 0.5%.

In some preferred embodiments of the invention, the packaged, heat-treated beverage preparation has a degree of protein denaturation of at most 10%. Preferably at most 8%, more preferably at most 5%, even more preferably at most 3%, even more preferably at most 1%, and most preferably at most 0.5%.

In some embodiments of the invention, when the protein fraction and or the beverage preparation have been subjected for example to a high temperature heat-treatment, then the degree of protein denaturation is more than 10%, preferably more than 20%, preferably more than 30%, preferably more than 40%, or preferably more than 50%, or preferably more than 70%, or preferably more than 80%, or preferably more than 90%, or preferably more than 95%, or preferably more than 99%.

For example, the protein fraction of the beverage preparation may have a degree of protein denaturation of more than 10%, preferably more than 20%, more preferably more than 30%, even more preferably more than 40%, and most preferably more than 50%. Even higher degrees of denaturation may be preferred, thus the protein fraction of the beverage preparation may have a degree of protein denaturation of more than 70%, preferably more than 80%, more preferably more than 90%, even more preferably more than 95%, and most preferably more than 99%.

In some preferred embodiments of the invention, the packaged, heat-treated beverage preparation has a pH in the range of 3.0-4.3. These pH-ranges are particularly preferred for production of transparent beverages having low viscosity and improved taste.

Regarding the appearance it was surprisingly found that use of whey protein beverages wherein at least 85% w/w of the protein is BLG enables the possibility to increase the pH during thermal treatment, which provides improvements in visual perception (colour and turbidity) and in viscosity when compared to heat-treated WPI beverages. Thus, the present invention increases the pH range and particularly the upper pH limit at which it is possible to heat-treat an acidic whey protein beverage and produce a heat-treated low viscous and preferably also transparent acidic beverage.

It has surprisingly been found that there is a significant difference in the sensory parameters between beverages produced with WPI compared to the BLG beverages of the present invention. It was found that, surprisingly and advantageously, the BLG beverage had a lower level of astringency, drying mouth-feeling, sourness, whey aroma and citric acid flavour compared to a WPI beverage. It was furthermore found that by increasing the pH of an acidic beverage less sweetener was required to balance out the acidity of the beverage and a lower concentration of sweetener is therefore required in such beverages.

In some preferred embodiments of the invention, the packaged, heat-treated beverage preparation has a pH in the range of 3.0-4.1, or preferably 3.1-4.0 or preferably 3.2-3.9, or preferably 3.7-3.9, more preferably 3.4-3.9, and even more preferably 3.5-3.9.

The pH of the packaged, heat-treated beverage preparation may preferably be in the range of 3.7-4.3, more preferably in the range of 3.9-4.3, even more preferred in the range of 4.1-4.3.

Alternatively, but also preferred, the pH of the packaged, heat-treated beverage preparation may be in the range of 3.7-4.1, and more preferably in the range of 3.9-4.1.

These pH ranges are particularly relevant when the beverage preparation is pasteurised.

In some preferred embodiments of the invention, the packaged, heat-treated beverage preparation preferably has a pH in the range of 3.0-3.9, or preferably 3.2-3.7, or preferably 3.4-3.6. or preferably 3.5-3.7, or preferably 3.4-3.6.

These pH-ranges combined with high temperature treatment, such as sterilisation, are particularly relevant for production of transparent beverages having low viscosity and improved taste.

In some preferred embodiments of the invention, the packaged, heat-treated beverage preparation has a pH in the range of 4.1-4.7, this pH range is particularly relevant for the production of stable beverages having a milky appearance and a high turbidity while still having a low viscosity. In some embodiments of the invention, the pH range is of 4.2-4.6. In some other embodiments of the invention, the pH range is of 4.2-4.5.

In some preferred embodiments of the invention, the packaged, heat-treated beverage preparation has a pH in the range of 3.0-3.9 and a total amount of protein of 10-34% w/w relative to the weight of the beverage preparation, more preferably 12-30% w/w, and even more preferably 15-25% w/w.

In other preferred embodiments of the invention, the packaged, heat-treated beverage preparation has a pH in the range of 3.7-3.9 and a total amount of protein of 10-34% w/w relative to the weight of the beverage preparation, more preferably 12-30% w/w, and even more preferably 15-25% w/w.

In further preferred embodiments of the invention, the packaged, heat-treated beverage preparation has:
a pH in the range of 3.0-3.9, preferably 3.7-3.9,
a total amount of protein of 10-34% w/w relative to the weight of the beverage preparation, more preferably 12-30% w/w, and even more preferably 15-25% w/w, and
an intrinsic tryptophan fluorescence emission ratio (I330 nm/I350 nm) of at least 1.13, more preferably at least 1.15, even more preferably at least 1.17, and most preferably at least 1.19.

In even further preferred embodiments of the invention, the packaged, heat-treated beverage preparation has:
a pH in the range of 3.0-3.9, preferably 3.7-3.9,
a total amount of protein of 10-34% w/w relative to the weight of the beverage preparation, more preferably 12-30% w/w, and even more preferably 15-25% w/w, and
a degree of protein denaturation of at most 10%, preferably at most 5% and even more preferably at most 1%.

The visual appearance of the beverage preparation is of importance to the consumer both with respect to transparent and opaque beverages. Particularly for clear, water-like beverages, or white, milky beverages the inventors have found it advantageous to be able to control the colour of the beverage—or rather to control the lack of colour of the beverage.

However, even if dedicated colouring agents are added during the production of the beverage the inventors have found it advantageous to be able to avoid additional sources of colour to avoid unwanted variation or changes in the visual appearance of the beverage. The present inventors have found that the high BLG protein profile described herein is more colour neutral/colourless than conventional WPI and contributes with less colour variation that conventional WPI. Conventional WPI has a yellowish appearance which may be diminished to some extent by addition of an oxidizing agent such as bleach. However, addition of oxidizing agents is often not desirable and with the present invention it is not even necessary anymore.

The CIELAB colour scale as described in example 1.9 is used to determine the colour of a beverage. As an example a positive delta b*value indicates a colour that is more yellow than demineralized water whereas a negative delta b*value indicates a beverage that is more blue than demineralised water. It is therefore often preferred by the costumer that the colour delta b*value should be close to 0, in order to have a beverage that is neither yellow nor blue.

In some preferred embodiments of the present invention the packaged, heat-treated beverage preparation has a colour value delta b* in the range of −0.10 to +0.51 at the CIELAB colour scale, particularly if the preparation has a turbidity of at most 200 NTU, and more preferably at most 40 NTU.

In other preferred embodiments of the invention, the packaged, heat-treated beverage preparation has a colour value delta b* in the range of 0.0 to 0.40 at the CIELAB colour scale, preferably in the range of 0.10 to 0.25.

For opaque beverage preparations, e.g. having a turbidity above 200 NTU and preferably above 1000 NTU, the packaged, heat-treated beverage preparation preferably has a colour value delta b* at the CIELAB colour scale, in the range of −6 to −1.7; preferably in the range of −5.0 to −2.0. In other preferred embodiments of the invention, a beverage preparation having a turbidity above 200 NTU, and preferably above 1000 NTU, has a colour value delta b* at the CIELAB colour scale in the range of −10 to −0.5, and more preferably in the range of −9 to −1.0.

In some preferred embodiments of the invention, the protein fraction of the packaged, heat-treated beverage preparation has a colour value delta b* in the range of −0.10 to +0.51, particularly if the preparation has a turbidity of at most 200 NTU, and more preferably at most 40 NTU.

These beverages have a less yellow colour compared to a beverage comprising WPI which had a higher delta b* value and a more yellow colour.

In other preferred embodiments of the invention, the protein fraction of the packaged, heat-treated beverage preparation has a colour value delta b* in the range of 0.0 to 0.40 at the CIELAB colour scale, preferably in the range of 0.10 to 0.25.

The a*-value represents the green-red component, with green in the negative direction and red in the positive direction. It is often preferred that the colour delta a*value should be around zero, in order to have a beverage that is neither red nor green.

It is typically preferred that the protein fraction of the packaged, heat-treated beverage preparation has a delta a* is in the range of –0.2 to 0.2 at the CIELAB colour scale, particularly if the preparation has a turbidity of at most 200 NTU, and more preferably at most 40 NTU. Preferably, the packaged, heat-treated beverage preparation has a colour value delta a* in the range of –0.15 to 0.15 at the CIELAB colour scale, preferably in the range of –0.10 to 0.10.

The present inventors have found that it can be advantageous to control the mineral content to reach some of the desired properties of the packaged, heat-treated beverage preparation.

In some embodiments of the invention, the packaged, heat-treated beverage preparation comprises a plurality of minerals. In one exemplary embodiment, the packaged, heat-treated beverage preparation comprises at least four minerals. In one embodiment the four minerals are sodium, potassium, magnesium and calcium.

The present inventors have surprisingly found that when a BLG isolate is used as defined herein and in example 2, heat-treated beverage preparations having a high mineral concentration can be produced, without compromising the viscosity. This provides the possibility that packaged, heat-treated beverage preparations can be produced having a high mineral content and that beverages that are nutritionally complete nutritional supplements or nutritionally incomplete supplements can be produced.

In some preferred embodiments of the invention, the sum of the amounts of Na, K, Mg and Ca is within the range of 0 to 750 mM in the packaged, heat-treated beverage preparation, preferably within the range of 100-600 mM or preferably within the range of 200-500 mM.

In some preferred embodiments of the invention, the sum of the amounts of Na, K, Mg and Ca is at most 750 mM in the packaged, heat-treated beverage preparation.

In other preferred embodiments of the invention, the sum of the amounts of Na, K, Mg and Ca is at most 600 mM in the packaged, heat-treated beverage preparation, preferably at most 500 mM, or preferably at most 400 mM, or preferably at most 300 mM, or preferably at most 200 mM, preferably at most 170 mM, most preferably at most 150 mM, or preferably at most 130 mM, or preferably at most 100 mM or preferably at most 80 mM or preferably at most 60 mM or preferably at most 40 mM or preferably at most 30 mM or preferably at most 20 mM or preferably at most 10 mM or preferably at most 5 mM or preferably at most 1 mM.

In another exemplary embodiment, the packaged, heat-treated beverage preparation comprises a plurality of minerals selected from the group consisting of: Calcium, Iodine, Zinc, Copper, Chromium, Iron, Phosphorus, Magnesium, Selenium, Manganese, Molybdenum, Sodium, Potassium, and combinations thereof.

In some preferred embodiments of the present invention the packaged, heat-treated beverage preparation comprises at most 150 mM KCl and at most 150 mM CaCl2, or the packaged, heat-treated beverage preparation comprises at most 130 mM KCl and at most 130 mM CaCl2 or the packaged, heat-treated beverage preparation comprises at most 110 mM KCl and at most 110 mM CaCl2 or the packaged, heat-treated beverage preparation comprises at most 100 mM KCl and at most 100 mM CaCl2 or preferably the packaged, heat-treated beverage preparation comprises at most 80 mM KCl and at most 80 mM CaCl2 or preferably the packaged, heat-treated beverage preparation comprises at most 50 mM KCl and at most 50 mM CaCl2 or preferably the packaged, heat-treated beverage preparation comprises at most 40 mM KCl and at most 40 mM CaCl2.

In other preferred embodiments of the invention, the heat-treated beverage preparation is a low mineral beverage.

In the context of the present invention the term "low mineral" pertains to a composition, e.g. a liquid, beverage, a powder or another food product, that has at least one, preferably two, and even more preferably all, of the following:

an ash content of at most 1.2% w/w relative to total solids,
a total content of calcium and magnesium of at most 0.3% w/w relative to total solids,
a total content of sodium and potassium of at most 0.10% w/w relative to total solids,
a total content of phosphorus of at most 100 mg phosphorus per 100 g protein.

Preferably, a low mineral composition has at least one, preferably two or more, and even more preferably all, of the following:

an ash content of at most 0.7% w/w relative to total solids,
a total content of calcium and magnesium of at most 0.2% w/w relative to total solids,
a total content of sodium and potassium of at most 0.08% w/w relative to total solids,
a total content of phosphorus of at most 80 mg phosphorus per 100 g protein.

Even more preferably, a low mineral composition has at least one, preferably two or more, and even more preferably all, of the following:

an ash content of at most 0.5% w/w relative to total solids,
a total content of calcium and magnesium of at most 0.15% w/w relative to total solids,
a total content of sodium and potassium of at most 0.06% w/w relative to total solids,
a total content of phosphorus of at most 50 mg phosphorus per 100 g protein.

It is particularly preferred that a low mineral composition has the following:

an ash content of at most 0.5% w/w relative to total solids,
a total content of calcium and magnesium of at most 0.15% w/w relative to total solids,
a total content of sodium and potassium of at most 0.06% w/w relative to total solids,
a total content of phosphorus of at most 50 mg phosphorus per 100 g protein.

The present inventors have found that the present invention makes it possible to prepare a packaged, heat-treated beverage preparation having a very low content of phosphorus and other minerals such as Potassium, which is advantageous for patients suffering from kidney diseases or otherwise having a reduced kidney function.

The packaged, heat-treated beverage preparation is preferably a low phosphorus beverage preparation.

The packaged, heat-treated beverage preparation is preferably a low Potassium beverage preparation.

The packaged, heat-treated beverage preparation is preferably low phosphorus and a low Potassium beverage preparation In the context of the present invention the term "low phosphorus" pertains to a composition, e.g. a liquid, a powder or another food product, that has a total content of phosphorus of at most 100 mg phosphorus per 100 g protein. Preferably, a low phosphorus composition has a total content of at most 80 mg phosphorus per 100 g protein. More preferably, a low phosphorus composition may have a total content of at most 50 mg phosphorus per 100 g protein. Even more preferably, a low phosphorus composition may have a total content of phosphorus of at most 20 mg phosphorus per 100 g protein. Even more preferably, a low phosphorus composition may have a total content of phosphorus of at most 5 mg phosphorus per 100 g protein. Low phosphorus compositions according to the present invention may be used as a food ingredient for the production of a food product for patient groups that have a reduced kidney function.

Thus, in some particularly preferred embodiments of the invention, the packaged, heat-treated beverage preparation comprises at most 80 mg phosphorus per 100 g protein. Preferably, the packaged, heat-treated beverage preparation comprises at most 30 mg phosphorus per 100 g protein. More preferably, the packaged, heat-treated beverage preparation comprises at most 20 mg phosphorus per 100 g protein. Even more preferably, the packaged, heat-treated beverage preparation comprises at most 10 mg phosphorus per 100 g protein. Most preferably, the packaged, heat-treated beverage preparation comprises at most 5 mg phosphorus per 100 g protein.

The content of phosphorus relates to the total amount of elemental phosphorus of the composition in question and is determined according to Example 1.19.

In the context of the present invention the term "low potassium" pertains to a composition, e.g. a liquid, a powder or another food product, that has a total content of potassium of at most 700 mg potassium per 100 g protein. Preferably, a low phosphorus composition has a total content of at most 600 mg potassium per 100 g protein. More preferably, a low potassium composition may have a total content of at most 500 mg potassium per 100 g protein. More preferably, a low potassium composition may have a total content of potassium of at most 400 mg potassium per 100 g protein. More preferably, a low potassium composition may have a total content of potassium of at most 300 mg potassium per 100 g protein. Even more preferably, a low potassium composition may have a total content of potassium of at most 200 mg potassium per 100 g protein. Even more preferably, a low potassium composition may have a total content of potassium of at most 100 mg potassium per 100 g protein. Even more preferably, a low potassium composition may have a total content of potassium of at most 50 mg potassium per 100 g protein and even more preferably, a low potassium composition may have a total content of potassium of at most 10 mg potassium per 100 g protein.

Low potassium compositions according to the present invention may be used as a food ingredient for the production of a food product for patient groups that have a reduced kidney function.

Thus, in some particularly preferred embodiments of the invention, the packaged, heat-treated beverage preparation comprises at most 600 mg potassium per 100 g protein. More preferably, the packaged, heat-treated beverage preparation comprises at most 500 mg potassium per 100 g protein. More preferably, the packaged, heat-treated beverage preparation comprises at most 400 mg potassium per 100 g protein. More preferably, the packaged, heat-treated beverage preparation comprises at most 300 mg potassium per 100 g protein. Even more preferably, the packaged, heat-treated beverage preparation comprises at most 200 mg potassium per 100 g protein. Even more preferably, the packaged, heat-treated beverage preparation comprises at most 100 mg potassium per 100 g protein. Even more preferably, the packaged, heat-treated beverage preparation comprises at most 50 mg potassium per 100 g protein and even more preferably, the packaged, heat-treated beverage preparation comprises at most 10 mg potassium per 100 g protein The content of potassium relates to the total amount of elemental potassium of the composition in question and is determined according to Example 1.19.

In some preferred embodiments of the invention, the packaged, heat-treated beverage preparation comprises at most 100 mg phosphorus/100 g protein and at most 700 mg potassium/100 g protein, preferably at most 80 mg phosphorus/100 g protein and at most 600 mg potassium/100 g protein, more preferably at most 60 mg phosphorus/100 g protein and at most 500 mg potassium/100 g protein, more preferably at most 50 mg phosphorus/100 g protein and at most 400 mg potassium/100 g protein, or more preferably at most 20 mg phosphorus/100 g protein and at most 200 mg potassium/100 g protein, or even more preferably at most 10 mg phosphorus/100 g protein and at most 50 mg potassium/100 g protein. In some preferred embodiments of the invention, the packaged, heat-treated beverage preparation comprises at most 100 mg phosphor/100 g protein and at most 340 mg potassium/100 g protein.

The heat-treated beverage preparation comprising low amounts of phosphorus and Potassium may advantageously be supplemented with carbohydrates and lipids, the heat-treated beverage preparation preferably furthermore comprises a total amount of carbohydrates in a range between 30-60% of the total energy content of the beverage, preferably in a range between 35-50 E % and a total amount of lipid in the range of 20-60% of the total energy content, preferably in a range between 30-50 E %.

In one embodiment of the invention, the packaged, heat-treated beverage preparation comprises a plurality of vitamins. In one exemplary embodiment, the packaged, heat-treated beverage preparation comprises at least ten vitamins. In one exemplary embodiment, the packaged, heat-treated beverage preparation comprises a plurality of vitamins selected from the group consisting of: Vitamin A, vitamin B1, vitamin B2, vitamin B3, vitamin B5, vitamin B6, vitamin B7, vitamin B9, vitamin B12, vitamin C, vitamin D, vitamin K, Riboflavin, pantothenic Acid, vitamin E, thiamin, niacin, folic acid, biotin, and combinations thereof.

In one embodiment of the invention, the packaged, heat-treated beverage comprises a plurality of vitamins and a plurality of minerals.

In some preferred embodiments of the present invention the packaged, heat-treated beverage preparation contains one or more food acids selected from the group consisting of citric acid, malic acid, tartaric acid, acetic acid, benzoic acid, butyric acid, lactic acid, fumaric acid, succinic acid, ascorbic acid, adipic acid, phosphoric acid, and mixtures thereof.

In an embodiment of the present invention, the packaged, heat-treated beverage preparation furthermore comprises a flavor selected from the group consisting of salt, flavorings, flavor enhancers and/or spices. In a preferred embodiment of the invention, the flavor comprises chocolate, cocoa, lemon, orange, lime, strawberry, banana, forest fruit flavor or combinations thereof. The choice of flavor may depend on the beverage to be produced.

Transparency is a parameter that the consumer uses to evaluate the product. One way of determining the transparency of the liquid food product is by measuring the turbidity of the product as described in example 1.7.

In some embodiments of the packaged, heat-treated beverage preparation it is beneficial that the beverage preparation is transparent. This may for example be advantageous when the beverage is used a sport beverage or in "protein water", in which case it is beneficial that the beverage resembles water in appearance.

In a preferred embodiment of the present invention the packaged, heat-treated beverage preparation has a turbidity of at most 200 NTU, such a beverage is transparent.

It has surprisingly been found by the inventors that transparent heat-treated beverage preparations having a turbidity of at most 200 NTU could be obtained by the heat-treated beverage preparation according to the invention.

This was found both when the heat-treatment applied was sterilization and pasteurisation.

In some preferred embodiments of the present invention the packaged, heat-treated beverage preparation has a turbidity of at most 150 NTU, or preferably a turbidity of at most 100 NTU, or preferably a turbidity of at most 80 NTU, or preferably a turbidity of at most 60 NTU or more preferably a turbidity of at most 40 NTU, or preferably a turbidity of at most 30 NTU, preferably a turbidity of at most 20 NTU, more preferably a turbidity of at most 10 NTU, and more preferably a turbidity of at most 5 NTU, even more preferably it has a turbidity of at most 2 NTU.

In a preferred embodiment of the present invention the packaged, heat-treated beverage preparation has a turbidity of more than 200 NTU, such a beverage is opaque.

In some embodiments of the packaged, heat-treated beverage preparation it is beneficial that the beverage preparation is opaque. This is for example advantageous when the beverage should resemble milk and have a milky appearance. The appearance of nutritionally complete nutritional supplements is typically opaque.

In some preferred embodiments of the invention, the packaged, heat-treated beverage preparation has a turbidity of more than 250 NTU. Preferably the packaged, heat-treated beverage preparation has a turbidity of more than 300 NTU, more preferably it has a turbidity of more than 500 NTU, more preferably it has a turbidity of more than 1000, preferably a turbidity of more than 1500 NTU, even more preferably it has a turbidity of more than 2000 NTU.

The amount of insoluble matter in the heat-treated beverage preparation is a measure of the instability of the beverage and to which extent sedimentation of precipitated matter takes place over time. Beverages having a high amount of insoluble matter are typically considered unstable.

In the context of the present invention whey protein beverage preparations are considered "stable" if at most 15% of total protein in heated samples precipitated upon centrifugation at 3000×g for 5 minutes. See analysis method in example 1.10.

It has surprisingly been found that when BLG is used as the protein source in an amount of at least 85 w/w %, compared to when WPI having a lower BLG content is used as the protein source, then the protein fraction contains at most 15% insoluble matter after centrifugation at 3000 g for 5 minutes demonstrating that the beverage preparation is stable.

Therefore, in some preferred embodiments of the present invention, the protein fraction of the heat-treated beverage preparation contains at most 15% insoluble matter.

In some preferred embodiments of the present invention, the packaged, heat-treated beverage preparation contains at most 15% insoluble matter.

In some preferred embodiments of the present invention the packaged, heat-treated beverage preparation contains preferably at most 12% insoluble matter, more preferably at most 10% insoluble matter, even more preferably at most 8% insoluble matter, and most preferably at most 6% insoluble matter.

Even lower levels of insoluble matter are often preferred and in some preferred embodiments the packaged, heat-treated beverage preparation contains at most 4% insoluble matter, preferably at most 2% insoluble matter, more preferably at most 1% insoluble matter, and most preferably no detectable insoluble matter at all.

The consumer prefer that the heat-treated beverage is liquid, easy to drink and does not gel.

One way of determining the viscosity of the beverage preparation is by measuring the viscosity of the beverage as described in example 1.8.

In some embodiments of the packaged, heat-treated beverage preparation it is beneficial that the beverage preparation has a very low viscosity. This is advantageous when the beverage is used as a sport beverage or in some embodiments of a nutritionally complete nutritional supplement or a nutritionally incomplete supplement.

It has surprisingly been found by the inventors that beverage preparations having an acidic pH and that have been subjected to a heat-treatment such as pasteurisation and even to sterilisation had a viscosity of at most 200 centipoise (cP), measured at 22 degrees Celsius at a shear rate of 100/s.

Therefore, in some preferred embodiments of the present invention the packaged, heat-treated beverage preparation has a viscosity of at most 200 cP.

Preferably, the viscosity of the packaged, heat-treated beverage preparation is at most 150 cP, preferably at most 100 cP, more preferably at most 80 cP, even more preferably at most 50 cP, and most preferably at most 40 cP.

Even lower viscosity is often preferred, thus in some preferred embodiments of the invention, the viscosity of the packaged, heat-treated beverage preparation is at most 20 cP, preferably at most 10 cP, more preferably at most 5 cP, even more preferably at most 3 cP, even more preferably at most 2 cP, and most preferably at most 1 cP.

It has previously been found that in order to produce acidic transparent heat-treated beverages comprising WPI, wherein the beverage has a pH above pH 3.0, it was essential to add an antiaggregant to the beverage, see for example Etzel 2004 (Etzel, M. R., 2004, Manufacture and use of dairy protein fraction. American Society for Nutritional Science, pp. 996-1002).

It was surprisingly found by the inventors that transparent heat-treated beverages comprising at least 85% w/w BLG can be produced even at a pH higher than pH 3.0 without the addition of an antiaggregant.

Therefore, in some preferred embodiments of the present invention the packaged, heat-treated beverage preparation does not comprise any antiaggregant or alternatively only traces of antiaggregant.

In the context of the present invention the term "antiaggregant" pertains to food grade, non-protein surfactants such as e.g. lauryl sulfate, polysorbate, and mono- and/or diglycerides.

In some embodiments of the invention, the packaged, heat-treated beverage preparation comprises at most 0.1% w/w antiaggregant, preferably at most 0.03% w/w antiaggregant, and most preferably no antiaggregant. The embodiments are particularly preferred in relation to transparent, low fat beverages.

In some preferred embodiments of the invention, the packaged, heat-treated beverage preparation does not comprise polyphenol.

However, in other preferred embodiments of the invention, the packaged, heat-treated beverage preparation comprises polyphenols. Polyphenols, such as e.g. epigallocatechin-3-gallate (EGCG), have been shown to limit the aggregation of whey proteins upon heat-treatment. While they are not necessary to make high protein beverage preparations according to the present invention, they may be used as ingredients.

Thus, it may be preferred that the packaged, heat-treated beverage preparation comprises a total amount of polyphenol in the range of 0.01-1% w/w, more preferably 0.02-0.6% w/w, even more preferred 0.03-0.4% w/w, and more preferred in the range of 0.04-0.2% w/w.

In some preferred embodiments of the invention, the polyphenol at least comprises, and may even essentially consist of, EGCG.

In some preferred embodiments of the present invention the packaged, heat-treated beverage preparation comprises a total amount of protein of 4.0 to 35% w/w relative to the weight of the beverage, and preferably 4.0 to 30% w/w.

In other preferred embodiments of the present invention, the packaged, heat-treated beverage preparation comprises a total amount of protein of 5.0 to 45% w/w relative to the weight of the beverage, more preferably 5.0 to 35% w/w, even more preferably 5.0 to 34% w/w, and most preferred 5.0 to 32% w/w.

In some preferred embodiments of the invention, the packaged, heat-treated beverage preparation contains a protein content in an amount of at least 3-45% w/w, more preferably 11-40% w/w, even more preferably 15-38% w/w and most preferably 20-36% w/w.

In some embodiments of the invention, it is advantageous that the packaged, heat-treated beverage preparation has a protein content of 2.0 to 10.0% w/w relative to the weight of the beverage.

Therefore, in some embodiments of the invention, the packaged, heat-treated beverage preparation preferably comprises a total amount of protein of 2.0 to 10% w/w relative to the weight of the beverage, preferably a total amount of protein of 3.0 to 10% w/w relative to the weight of the beverage, preferably a total amount of protein of 5.0 to 9.0% w/w relative to the weight of the beverage, preferably a total amount of protein of 6.0 to 8.0% w/w relative to the weight of the beverage.

In some embodiments of the invention, it is advantageous that the protein content of the beverage is high such as 10.0 to 45.0% w/w relative to the weight of the beverage.

Therefore in some embodiments of the present invention the packaged, heat-treated beverage preparation preferably comprises a total amount of protein of 10.0 to 45.0% w/w relative to the weight of the beverage, preferably a total amount of protein of 10.0 to 20% w/w relative to the weight of the beverage, preferably a total amount of protein of 12 to 30% w/w relative to the weight of the beverage, preferably a total amount of protein of 15 to 25% w/w relative to the weight of the beverage, preferably a total amount of protein of 18 to 20% w/w relative to the weight of the beverage.

In other preferred embodiments of the invention, it is advantageous that the protein content of the packaged, heat-treated beverage preparation is 5.0 to 45.0% w/w relative to the weight of the packaged, heat-treated beverage preparation, preferably 6.0 to 35% w/w, more preferably 7.0 to 34% w/w, even more preferred 8.0-32% w/w, and most preferred 10-30% w/w.

The present invention surprisingly makes it possible to provide packaged, heat-treated beverage preparations having a protein content of and exceeding 15% w/w and even exceeding 20% w/w. Thus in some preferred embodiments of the invention, the packaged, heat-treated beverage preparation preferably comprises a total amount of protein of 15 to 45.0% w/w relative to the weight of the beverage preparation, preferably a total amount of protein of 20 to 35% w/w relative to the weight of the beverage preparation, more preferably a total amount of protein of 21 to 34% w/w relative to the weight of the beverage preparation, and even more preferably a total amount of protein of 25 to 32% w/w relative to the weight of the beverage preparation.

In other preferred embodiments of the invention, the packaged, heat-treated beverage preparation preferably comprises a total amount of protein of 21 to 35% w/w relative to the weight of the beverage preparation, preferably a total amount of protein of 25 to 35% w/w relative to the weight of the beverage preparation, more preferably a total amount of protein of 28 to 35% w/w relative to the weight of the beverage preparation, and even more preferably a total amount of protein of 30 to 35% w/w relative to the weight of the beverage preparation.

In further preferred embodiments of the invention, the packaged, heat-treated beverage preparation preferably comprises a total amount of protein of 21 to 33% w/w relative to the weight of the beverage preparation, preferably a total amount of protein of 25 to 33% w/w relative to the weight of the beverage preparation, and more preferably a total amount of protein of 28 to 33% w/w relative to the weight of the beverage preparation.

The protein of the liquid solution is preferably prepared from mammal milk, and preferably from ruminant milk such as e.g. milk from cow, sheep, goat, buffalo, camel, llama, mare and/or deer. Protein derived from bovine milk is particularly preferred. The protein of the liquid solution is therefore preferably bovine milk protein.

The protein of the liquid solution is preferably whey protein and/or milk serum protein and even more preferably bovine whey protein and/or milk serum protein.

The packaged, heat-treated beverage preparation of the invention is particularly useful as a sport beverage in which case it preferably contains optionally only a limited amount of lipid and/or optionally also a limited amount of carbohydrates.

In some preferred embodiments of the present invention the preparation is particularly useful as a sport beverage and comprises e.g. a total amount of protein in the range of 2-45% w/w relative to the weight of the beverage, preferably 2-20% w/w relative to the weight of the beverage, or preferably 2-10% w/w relative to the weight of the beverage, most preferably 2-6% w/w relative to the weight of the beverage.

In some preferred embodiments of the present invention the packaged, heat-treated beverage preparation is particularly useful as a nutritionally incomplete nutritional supplement and comprises e.g. a total amount of protein in the range of 2-45% w/w relative to the weight of the beverage, preferably 2-20% w/w relative to the weight of the beverage, or preferably 3-10% w/w relative to the weight of the beverage.

In some preferred embodiments of the present invention the packaged, heat-treated beverage preparation is particularly useful as a nutritionally complete nutritional supplement and comprises e.g. a total amount of protein in the range of 4-45% w/w relative to the weight of the beverage or preferably 5-20% w/w relative to the weight of the beverage.

In some preferred embodiments of the present invention the packaged, heat-treated beverage preparation is particularly advantageous for patients suffering from kidney diseases or otherwise having a reduced kidney function.

In some preferred embodiments of the present invention the packaged, heat-treated beverage preparation comprises e.g. a total amount of protein in the range of 2-45% w/w relative to the weight of the beverage, preferably 2-20% w/w relative to the weight of the beverage, or preferably 3-12% w/w relative to the weight of the beverage, or preferably 3-10% w/w relative to the weight of the beverage.

It is particularly preferred that the packaged, heat-treated beverage preparation comprises a BLG isolate, e.g. in combination with other protein sources, preferably as the main protein source and possibly even as the only protein source.

The packaged, heat-treated beverage preparation of the present invention may comprise other macronutrients than proteins. In some embodiments of the invention, the packaged, heat-treated beverage preparation furthermore comprises carbohydrates. The total carbohydrate content in the heat-treated beverage preparation of the invention depends on the intended use of the heat-treated beverage preparation.

In some preferred embodiments of the invention, the packaged, heat-treated beverage preparation furthermore comprises at least one source of carbohydrate. In one exemplary embodiment, the at least one source of carbohydrate is selected from the group consisting of: sucrose, maltodextrin, corn syrup solids, saccharose, maltose, sucromalt, maltitol powder, glycerine, glucose polymers, corn syrup, modified starches, resistant starches, rice-derived carbohydrates, isomaltulose, white sugar, glucose, fructose, lactose, high fructose corn syrup, honey, sugar alcohols, fructooligosaccharides, soy fiber, corn fiber, guar gum, konjac flour, polydextrose, Fibersol, and combinations thereof.

In some preferred embodiments of the invention, the packaged heat-treated beverage preparation comprises sugar polymers, i.e. oligosaccharides and/or polysaccharides.

In some preferred embodiments the packaged, heat-treated beverage preparation furthermore comprises carbohydrates in a range between 0 to 95% of the total energy content of the preparation, preferably in a range between 10 to 85% of the total energy content of the preparation, preferably in a range between 20 to 75% of the total energy content of the preparation or preferably in a range between 30 to 60% of the total energy content of the preparation.

Even lower carbohydrate content is often preferred, thus in some preferred embodiments of the invention, the carbohydrate content of the packaged, heat-treated beverage preparation is preferably in a range between 0 to 30% of the total energy content of the preparation more preferably in a range between 0 to 20% of the total energy content of the preparation even more preferably in a range between 0 to 10% of the total energy content of the preparation.

In some preferred embodiments of the invention, the carbohydrate content of the packaged, heat-treated beverage preparation is at most 5% of the total energy content of the preparation, more preferably at most 1% of the total energy content of the preparation, and even more preferably at most 0.1% of the total energy content of the preparation.

In some preferred embodiments of the present invention the preparation is particularly useful as a sport beverage and comprises a total amount of carbohydrate of at most 75% of the total energy content of the beverage (E), preferably at most 40 E %, preferably at most 10 E % or preferably at most 5 E %.

In some preferred embodiments of the present invention the packaged, heat-treated beverage preparation is particularly useful as a nutritionally incomplete nutritional supplement and comprises a total amount of carbohydrate in a range between 70-95% of the total energy content of the beverage (E), preferably 80-90 E %.

In some preferred embodiments of the present invention the packaged, heat-treated beverage preparation is particularly useful as a nutritionally complete nutritional supplement and comprises a total amount of carbohydrate in a range between 30-60% of the total energy content of the beverage, preferably in a range between 35-50 E %.

In some preferred embodiments of the present invention the packaged, heat-treated beverage preparation is particularly advantageous for patients suffering from kidney diseases or otherwise having a reduced kidney function.

In some preferred embodiments of the present invention the packaged, heat-treated beverage preparation comprises a total amount of carbohydrate in a range between 30-60% of the total energy content of the beverage, preferably in a range between 35-50 E %.

In one embodiment of the invention, the packaged, heat-treated beverage preparation furthermore comprises at least one additional ingredient selected from the group consisting of vitamins, flavouring agent, minerals, sweeteners, antioxidants, food acid, lipids, carbohydrate, prebiotics, probiotics and non-whey protein.

In one embodiment of the invention, the beverage preparation furthermore comprises at least one high intensity sweetener. In one embodiment, the at least one high intensity sweetener is selected from the group consisting of aspartame, cyclamate, sucralose, acesulfame salt, neotame, saccharin, stevia extract, a steviol glycoside such as e.g. rebaudioside A, or a combination thereof. In some embodiments of the invention, it is particularly preferred that the sweetener comprises or even consists of one or more high intensity sweeteners (HIS).

HIS are both found among both natural and artificial sweeteners and typically have a sweetening intensity of at least 10 times that of sucrose.

If used, the total amount of HIS is typically in the range of 0.01-2% w/w. For example, the total amount of HIS may be in the range of 0.05-1.5% w/w. Alternatively, the total amount of HIS may be in the range of 0.1-1.0% w/w.

The choice of the sweetener may depend on the beverage to be produced, e.g. high-intensity sugar sweeteners (e.g. aspartame, acetsulfam-K or sucralose) may be used in beverage where no energy contribution from the sweetener is desired, whereas for beverages having a natural profile natural sweeteners (e.g. steviol glycosides, sorbitol or sucrose) may be used.

It may furthermore be preferred that the sweetener comprises or even consists of one or more polyol sweetener(s). Non-limiting examples of useful polyol sweetener are maltitol, mannitol, lactitol, sorbitol, inositol, xylitol, threitol, galactitol or combinations thereof. If used, the total amount of polyol sweetener is typically in the range of 1-20% w/w.

For example, the total amount of polyol sweetener may be in the range of 2-15% w/w. Alternatively, the total amount of polyol sweetener may be in the range of 4-10% w/w.

The packaged, heat-treated beverage preparation of the present invention may comprise other macronutrients than proteins. In some embodiments of the invention, the packaged, heat-treated beverage preparation furthermore comprises lipids. The total lipid content in the heat-treated beverage preparation of the invention depends on the intended use of the heat-treated beverage preparation.

In some preferred embodiments of the invention, the packaged, heat-treated beverage preparation has a lipid content between 0 to 60% of the total energy content of the preparation, or preferably in a range between 0 to 50% of the total energy content of the preparation or preferably in a range between 0 to 45% of the total energy content of the preparation, or preferably in a range between 0 to 30% of the total energy content of the preparation or preferably in a range between 0 to 20% of the total energy content of the preparation or preferably in a range between 0 to 10% of the total energy content of the preparation or preferably in a range between 0 to 5% of the total energy content of the preparation.

The amount of lipid is determined according to ISO 1211:2010 (Determination of Fat Content—Röse-Gottlieb Gravimetric Method).

In some preferred embodiments of the invention, the lipid content of the packaged, heat-treated beverage preparation is at most 3% of the total energy content of the preparation, more preferably at most 1% of the total energy content of the preparation, and even more preferably at most 0.1% of the total energy content of the preparation.

In some preferred embodiments of the present invention the preparation is particularly useful as a sport beverage and comprises e.g. a total amount of lipid of at most 10 E %, preferably at most at most 1 E %.

In some preferred embodiments of the present invention the packaged, heat-treated beverage preparation is particularly useful as a nutritionally incomplete nutritional supplement and comprises e.g. a total amount of lipid of at most 10% of the total energy content of the beverage, preferably at most 1 E %.

In some preferred embodiments of the present invention the packaged, heat-treated beverage preparation is particularly useful as a nutritionally complete nutritional supplement and comprises e.g. a total amount of lipid in the range of 20-50% of the total energy content, preferably in a range between 30-40 E %.

In some preferred embodiments of the present invention the packaged, heat-treated beverage preparation is particularly advantageous for patients suffering from kidney diseases or otherwise having a reduced kidney function.

In some preferred embodiments of the present invention the packaged, heat-treated beverage preparation comprises e.g. a total amount of lipid in the range of 20-60% of the total energy content, preferably in a range between 30-50 E %.

The beverage preparation typically contains a total amount of water in the range of 50-98% w/w, preferably in the range of 45-97% w/w, more preferably in the range of 40-95% w/w, even more preferably in the range of 35-90% w/w, and most preferably in the range of 30-85% w/w.

In some preferred embodiments of the invention, the beverage preparation contains a total amount of water in the range of 55-90% w/w, preferably in the range of 57-85% w/w, more preferably in the range of 60-80% w/w, even more preferably in the range of 62-75% w/w, and most preferably in the range of 65-70% w/w.

In some preferred embodiments of the invention, the beverage preparation contains a total amount of water in the range of 90-98% w/w, preferably in the range of 92-97.5% w/w, more preferably in the range of 94-97% w/w, even more preferably in the range of 95-97% w/w, and most preferably in the range of 96-97% w/w. These embodiments are e.g. useful for transparent, water-like beverages.

In some preferred embodiments of the invention, the beverage preparation is non-alcoholic meaning that it contains at most 1.0% w/w ethanol, more preferably at most 0.5% w/w, even more preferably at most 0.1% w/w, and most preferably no detectable ethanol.

The beverage preparation typically contains an amount of total solids in the range of 1-45% w/w, preferably in the range of 5-40% w/w, more preferably in the range of 10-35% w/w, even more preferably in the range of 12-30% w/w, and most preferably in the range of 16-25% w/w.

In some preferred embodiments of the invention, the beverage preparation contains an amount of total solids in the range of 10-45% w/w, preferably in the range of 15-43% w/w, more preferably in the range of 20-40% w/w, even more preferably in the range of 25-38% w/w, and most preferably in the range of 30-35% w/w.

In some preferred embodiments of the invention the liquid solution contains an amount of total solids in the range of 1-10% w/w, preferably in the range of 1.5-8% w/w, more preferably in the range of 2-6% w/w, even more preferably in the range of 2-5% w/w, and most preferably in the range of 2-4% w/w. These embodiments are e.g. useful for transparent, water-like beverages.

The part of the beverage preparation that is not solids is preferably water.

In some preferred embodiments of the invention, the sum of alpha-lactalbumin (ALA) and caseinomacropeptide (CMP) comprises at least 40% w/w of the non-BLG protein of the beverage preparation, preferably at least 60% w/w, even more preferably at least 70% w/w, and most preferably at least 90% w/w of the non-BLG protein of the beverage preparation.

In other preferred embodiments of the invention, each main non-BLG whey protein is present in a weight percentage relative to total protein which is at most 25% of its weight percentage relative to total protein in a standard whey protein concentrate from sweet whey, preferably at most 20%, more preferably at most 15%, even more preferably at most 10%, most preferably at most 6%.

Even lower concentrations of the main non-BLG whey proteins may be desirable. Thus, in additional preferred embodiments of the invention, each main non-BLG whey protein is present in a weight percentage relative to total protein which is at most 4% of its weight percentage relative to total protein in a standard whey protein concentrate from sweet whey, preferably at most 3%, more preferably at most 2%, even more preferably at most 1%.

In some preferred embodiments of the invention, ALA comprises at most 80% w/w of the non-BLG protein of the beverage preparation, preferably at most 60% w/w, even more preferably at most 40% w/w, and most preferably at most 30% w/w of the non-BLG protein of the beverage preparation.

Even lower contents of ALA may be preferred, thus in some preferred embodiments of the invention, ALA comprises at most 20% w/w of the non-BLG protein of the beverage preparation, preferably at most 15% w/w, even more preferably at most 10% w/w, and most preferably at most 5% w/w of the non-BLG protein of the beverage preparation.

The inventors have seen indications that reduction of lactoferrin and/or lactoperoxidase is particularly advantageous for obtaining a colour-neutral whey protein product.

Thus in some preferred embodiments of the invention, lactoferrin is present in a weight percentage relative to total protein which is at most 25% of its weight percentage relative to total protein in a standard whey protein concentrate from sweet whey, preferably at most 20%, more preferably at most 15%, even more preferably at most 10%, most preferably at most 6%. Even lower concentrations of lactoferrin may be desirable. Thus, in additional preferred embodiments of the invention, lactoferrin is present in a weight percentage relative to total protein which is at most 4% of its weight percentage relative to total protein in a standard whey protein concentrate from sweet whey, preferably at most 3%, more preferably at most 2%, even more preferably at most 1%.

Similarly, in some preferred embodiments of the invention, lactoperoxidase is present in a weight percentage relative to total protein which is at most 25% of its weight percentage relative to total protein in a standard whey protein concentrate from sweet whey, preferably at most 20%, more preferably at most 15%, even more preferably at most 10%, most preferably at most 6%. Even lower concentrations of lactoperoxidase may be desirable. Thus, in additional preferred embodiments of the invention, lactoperoxidase is present in a weight percentage relative to total protein which is at most 4% of its weight percentage relative to total protein in a standard whey protein concentrate from sweet whey, preferably at most 3%, more preferably at most 2%, even more preferably at most 1%.

Lactoferrin and lactoperoxidase are quantified according to Example 1.29

In an embodiment of the invention, the packaged, heat-treated beverage preparation is a sports beverage.

In an embodiment of the invention, the packaged, heat-treated beverage preparation is a nutritionally complete nutritional supplement.

In an embodiment of the invention, the packaged, heat-treated beverage preparation is a nutritionally incomplete nutritional supplement.

In an embodiment of the invention, the packaged, heat-treated beverage preparation is a low phosphorus and low potassium beverage suitable for patients suffering from kidney diseases or otherwise having a reduced kidney function.

The packaged, heat-treated beverage preparation of the invention is particularly useful as a sport beverage in which case it preferably contains optionally only a limited amount of lipid and/or optionally also a limited amount of carbohydrates.

In some preferred embodiments of the present invention the preparation is particularly useful as a sport beverage and comprises e.g.:
- a total amount of protein in the range of 2-45% w/w relative to the weight of the beverage, preferably 2-20% w/w relative to the weight of the beverage, or preferably 2-10% w/w relative to the weight of the beverage, most preferably 2-6% w/w relative to the weight of the beverage
- a total amount of carbohydrate of at most 75% of the total energy content of the beverage (E), preferably at most 40 E %, preferably at most 10 E % or preferably at most 5 E % and
- a total amount of lipid of at most 10 E %, preferably at most at most 1 E %.

In some preferred embodiments of the present invention the packaged, heat-treated beverage preparation is particularly useful as a nutritionally incomplete nutritional supplement and comprises e.g.:
- a total amount of protein in the range of 2-45% w/w relative to the weight of the beverage, preferably 2-20% w/w or preferably 3-10% w/w relative to the weight of the beverage
- a total amount of carbohydrate in a range between 70-95% of the total energy content of the beverage (E), preferably 80-90 E %, and
- a total amount of lipid of at most 10% of the total energy content of the beverage, preferably at most 1 E %.

In some preferred embodiments of the present invention the packaged, heat-treated beverage preparation is particularly useful as a nutritionally complete nutritional supplement and comprises e.g.:
- a total amount of protein in the range of 4-45% w/w relative to the weight of the beverage, preferably 5-20% w/w relative to the weight of the beverage
- a total amount of carbohydrate in a range between 30-60% of the total energy content of the beverage, preferably in a range between 35-50 E % and
- a total amount of lipid in the range of 20-50% of the total energy content, preferably in a range between 30-40 E %.

In some preferred embodiments of the present invention the packaged, heat-treated beverage preparation is particularly advantageous for patients suffering from kidney diseases or otherwise having a reduced kidney function. The beverage preparation is having a very low content of phosphorus and other minerals such as Potassium.

In some preferred embodiments of the present invention the packaged, heat-treated beverage preparation comprises e.g.:
- a total amount of protein in the range of 2-45% w/w relative to the weight of the beverage, preferably 2-20% w/w relative to the weight of the beverage or preferably 3-12% w/w, preferably 3-10% w/w relative to the weight of the beverage,
- a total amount of carbohydrate in a range between 30-60% of the total energy content of the beverage, preferably in a range between 35-50 E % and
- a total amount of lipid in the range of 20-60% of the total energy content, preferably in a range between 30-50 E %.

The heat-treat beverage preparation is preferably present in suitable containers as described herein, e.g. bottles, cartons, bricks, and/or bags.

The present inventors have discovered that surprisingly heat-treat beverage preparation which have been exposed to at least some protein denaturation tend to develop colour during storage under some conditions. The inventors have subsequently discovered that the colour development is at least partially caused by exposure to light (electromagnetic radiation) and that this phenomenon increases with increasing concentrations of BLG. The inventors have furthermore found that the problem can be reduced or even avoided by selecting a container that blocks at least some of the ambient light.

Thus, in some preferred embodiments of the invention, the container wall has a light transmission at any wave length in the range of 250-500 nm of at most 10%, preferably at most 1%, more preferably at most 0.1%, even more preferably at most 0.01%, and most preferably at most 0.001%.

In other preferred embodiments of the invention, the container wall has an average light transmission in the range of 250-500 nm of at most 10%, preferably at most 1%, more preferably at most 0.1%, even more preferably at most 0.01%, and most preferably at most 0.001%.

The light transmission of the container wall is measured by providing a planar piece of container wall and measuring the light transmission through the container wall at any relevant wave length. The measurement is performed using a standard spectrophotometer and by inserting a piece of container wall into the light path (e.g. using a cuvette or a similar arrangement) so the plane of the piece of container wall is arranged perpendicular to the light path. The transmission at wavelength i is calculated as $T_i = I_{i,after}/I_{i,before} * 100\%$ where $I_{i,before}$ is the light intensity at wavelength i before reaching the container wall and $I_{i,after}$ is the intensity of at wavelength i after the light beam of the light path has passed the piece of container wall.

The average light transmission is calculated by calculating the sum of all the transmission measurement $T_i$ made within the given range of wave lengths and dividing the sum with the number of transmission measurements within the given range of wave lengths.

In some preferred embodiments of the invention, the container wall has a light transmission at any wave length in the range of 250-800 nm of most 10%, preferably at most 1%, more preferably at most 0.1%, even more preferably at most 0.01%, and most preferably at most 0.001%.

In other preferred embodiments of the invention, the container wall has an average light transmission in the range of 250-800 nm of most 10%, preferably at most 1%, more preferably at most 0.1%, even more preferably at most 0.01%, and most preferably at most 0.001%.

Such low light transmission containers may e.g. be produced using pigmented, absorbant-containing or coated polymers or coloured or coated glass, or alternatively incorporating a metal layer in the container wall, e.g. in the form of an aluminium foil. Such no- or low-light transmission containers are known in the food and pharma industry.

Non-limiting examples of a suitable polymer materials are e.g. polyethylene terephthalate (PET) or PET-like polymers.

The inventors have furthermore found that the colour development can be reduced or even avoided if the beverage preparation primarily contains BLG in native conformation. Reducing the degree of protein denaturation, e.g. by using a less denaturing process, therefore has been found to reduce the colour problem.

Thus, in some preferred embodiments of the invention, embodiments of the invention, at least a portion of the container wall is transparent, and preferably the entire container is transparent. In some preferred embodiments of the invention, at least a portion of the container wall, and preferably the entire container wall has an average light transmission in the range of 400-700 nm of at least 11%, preferably at least 20%, more preferably at least 50%, even more preferably at least 60%, and most preferably at least 80%.

An aspect of the invention pertains to a method of producing a packaged, heat-treated beverage preparation having a pH in the range of 2-4.7, comprising the following steps:
a) Providing a liquid solution comprising:
  a total amount of protein of 2 to 45% by weight, wherein at least 85% of the protein is BLG
  optionally, sweetener, sugar polymers and/or flavour
b) packaging the liquid solution,
  wherein the liquid solution of step a) and/or the packaged liquid solution of step b) is subjected to a heat-treatment comprising at least pasteurisation.

The liquid solution of step a) preferably has same chemical composition as described in the content of the heat-treated beverage preparations, except that the liquid solution lacks the final heat-treatment. Embodiments and preferences mentioned in the context of the heat-treated beverage preparations therefore equally apply to the liquid solution.

In some preferred embodiments the liquid solution of the invention at least 85% w/w of the protein is BLG. Preferably, at least 88% w/w of the protein is BLG, more preferably at least 90% w/w, even more preferably at least 91% w/w, and most preferably at least 92% w/w of the protein is BLG.

Even higher relative amounts of BLG are both feasible and desirable thus in some preferred embodiments of the invention, at least 94% w/w of the protein of the liquid solution is BLG, more preferably at least 96% w/w of the protein is BLG, even more preferably at least 98% w/w of the protein is BLG, and most preferably approx. 100% w/w.

For example, the liquid solution preferably comprises BLG in an amount of at least 97.5% w/w relative to total protein, preferably at least 98.0% w/w, more preferably at least 98.5% w/w, even more preferably at least 99.0%, and most preferably BLG in an amount of at least 99.5% w/w relative to total protein, such as approx. 100.0% w/w relative to total protein.

The packaging of step b) may be any suitable packaging techniques, and any suitable container may be used for packaging the liquid solution.

However, in a preferred embodiment of the invention, the packaging of step b) is aseptic packaging, i.e. the liquid solution is packaged under aseptic conditions. For example, the aseptic packaging may be performed by using an aseptic filling system, and it preferably involves filling the liquid solution into one or more aseptic container(s).

Aseptic filling and sealing is particularly preferred if the liquid solution already is sterile or very low in microorganisms prior to filling.

Examples of useful containers are e.g. bottles, cartons, bricks, and/or bags.

In some preferred embodiment of the method the packaged liquid solution of step b) is subjected to a heat-treatment comprising at least pasteurisation. The embodiment is typically referred to as in-container heat-treatment or retort treatment and involves heating the entire container and its contents to achieve pasteurization or even sterility. When using in-container heat-treatment it is particularly preferred that the temperature is kept in the range 70-82 degrees C., more preferably in the range 70-80 degrees C., and most preferably in the range 70-78 degrees C. In this way the level of protein unfolding is kept to a minimum.

In other preferred embodiments of the inventive method the liquid solution of step a) is subjected to a heat-treatment comprising at least pasteurisation and then subsequently packaged in step b).

In particularly preferred embodiments heat-treatment involves heating the beverage preparation to a temperature in the range of 70-82 degrees C.

In some preferred embodiments of the invention, the temperature of the heat-treatment is in the range 70-80 degrees C., preferably in the range 70-79 degrees C., more preferably in the range 71-78 degrees C., even more preferably in the range 72-77 degrees C., and most preferably in the range 73-76 degrees C., such as approx. 75 degrees C.

Preferably, the duration of the heat-treatment, when performed in the temperature range 70-82, is 1 second to 30 minutes. The highest exposure times are best suited for the lowest temperatures of the temperature range and vice versa. The lower the pH of the liquid solution the higher temperature can be tolerated without unfolding.

In particularly preferred embodiments of the invention, the heat-treatment provides 70-80 degrees C. for 1 second to 30 minutes, more preferably 71-77 degrees C. for 1 minute to 25 minutes, and even more preferred 72-76 degrees C. for 2 minute to 20 minutes.

In some preferred embodiments of the invention, the heat-treatment involves heating to a temperature of 85° C.-95 degrees C. for 1 to 3 minutes.

Higher temperatures may also be preferred in some embodiments, especially if unfolding and optionally also aggregation for BLG is required. For example, the temperature of the heat-treatment may be at least 81 degrees C., preferably at least 91 degrees C., preferably at least 95 degrees C., more preferred at least 100 degrees C., even more preferred at least 120 degrees C., and most preferred at least 140 degrees C.

In some preferred embodiments of the invention, the sterilisation involves a temperature in the range of 120 to 150 degrees C. for 4 to 30 seconds.

The heat-treatment may for example involve a temperature in the range of 90-130 degrees C. and a duration in the range of 5 seconds-10 minutes. The heat-treatment may e.g. involve heating to a temperature in the range of 90-95 degrees C. for a duration of 1-10 minutes, e.g. approx. 120 degrees C. for 20 approx. seconds. Alternatively, the heat-treatment may involve heating to a temperature in the range of 115-125 degrees C. for a duration of 5-30 seconds, e.g. approx. 120 degrees C. for approx. 20 seconds.

Alternatively, the heat-treatment may for example be a UHT-type treatment which typically involves a temperature in the range of 135-144 degrees C. and a duration in the range of 2-10 seconds.

Alternatively, but also preferred, the heat-treatment may involve a temperature in the range of 145-180 degrees C. and a duration in the range of 0.01-2 seconds, and more preferably a temperature in the range of 150-180 degrees C. and a duration in the range of 0.01-0.3 seconds.

The implementation of the heat-treatment may involve the use of equipment such as a plate or tubular heat exchanger, scraped surface heat exchanger or a retort system. Alternatively, and particularly preferred for heat-treatments above 95 degrees C., direct steam-based heating may be employed, e.g. using direct steam injection, direct steam infusion, or spray-cooking. Additionally, such direct steam-based heating is preferably used in combination with flash cooling. Suitable examples of implementation of spray-cooking are found in WO2009113858A1, which are incorporated herein for all purposes. Suitable examples of implementation of direct steam injection and direct steam infusion are found in WO2009113858A1 and WO 2010/085957 A3, which are incorporated herein for all purposes. General aspects of high temperature treatment are e.g. found in "Thermal technologies in food processing" ISBN 185573558 X, which is incorporated herein by reference for all purposes.

In some preferred embodiments of the invention, the pasteurisation is combined with another physical microbial reduction.

Useful examples of physical microbial reduction involve one or more of germ filtration, UV radiation, high pressure treatment, pulsed electric field treatment, and ultrasound.

In some particularly preferred embodiments of the invention, the heat-treatment is selected so that it provides a degree of protein denaturation of at most 50%, preferably at most 20%, even more preferred at most 10%, and most preferred at most 5%.

It is furthermore preferred that the heat-treatment is selected so that is provides an intrinsic tryptophan fluorescence ratio (I330/I350) of at least 1.11, preferably at least 1.13, more preferably at least 1.15, and even more preferred at least 1.17.

In some preferred embodiments of the invention, the heat-treatment is a sterilization resulting in a sterile liquid beverage preparation. Such a sterilisation may preferably be obtained by combining germ filtration and heat-treatment, e.g. pasteurisation. The sterilisation may e.g. involve heat-treatment followed by germ filtration, or even more preferred germ filtration followed by heat-treatment.

In the context of the present invention, the term "germ filtration" relates to filtration performed with pore size sufficient to retain microorganisms such as bacteria and spores yet with a pore size that does not retain native BLG. Germ filtration is also sometimes referred to as a sterile filtration and involves microfiltration of the liquid in question. The germ filtration is typically performed with a membrane having a pore size of at most 1 micron, preferably at most 0.8 micron, more preferably at most 0.6 micron, even more preferably at most 0.4 micron, and most preferably at most 0.2 micron.

The germ filtration may for example involve a membrane having a pore size of 0.02-1 micron, preferably 0.03-0.8 micron, more preferably 0.04-0.6 micron, even more preferably 0.05-0.4 micron, and most preferably 0.1-0.2 micron.

In some preferred embodiments of the invention, the liquid solution is subjected to a germ filtration and subsequently to the heat-treatment using a temperature of at most 80 degrees C., and preferably at most 78 degrees C. The duration of this heat-treatment is preferably chosen sufficiently long to prepare a sterile beverage preparation.

In other preferred embodiments of the invention, the liquid solution is subjected to a germ filtration and subsequently to the heat-treatment using a temperature of 81-160 degrees C., more preferably 100-155 degrees C. The combination of temperature and duration of this heat-treatment of preferably chosen to provide a sterile beverage preparation.

Depending on the used heat-treatment temperatures it is beneficial that the beverage preparation is subjected to cooling. According to a preferred aspect of the inventive process, following the heat-treatment, the heat-treated beverage preparation is in an optional step cooled to preferably 0 to 50 degrees C., preferably 0 to 25 degrees C. or preferably 0 to 20 degrees C. or preferably 0 to 15 degrees C., preferably 0 to 10 degrees C. or preferably 4 to 8 degrees C. or preferably 2 to 5 degrees C. or preferably 1 to 5 degrees C.

If the beverage preparation has been pasteurized it is preferably cooled to 0 to 15 degrees C. after the heat-treatment, preferably to 1 to 10 degrees C., and more preferably to 1 to 6 degrees C.

According to an embodiment of the method, generally any acid or base may be used to adjust the pH, Those skilled in the art will recognize means suitable for adjusting the pH. Suitable acids include, e.g. citric acid, hydrochloric acid, malic acid or tartaric acid, or phosphoric acid most preferably citric acid and/or phosphoric acid.

Useful examples of useful bases are hydroxide salts, e.g. sodium hydroxide or potassium hydroxide, carbonate salts or hydrocarbonate salts, carboxylate salts such as e.g. citrate salts or lactic acid salts and combinations thereof. Preferably, a base such as KOH or NaOH is employed to adjust the pH.

In some preferred embodiments of the invention, the liquid solution has a pH in the range of 3.0-4.3. These pH-ranges are particularly preferred for production of transparent beverages having low viscosity and improved taste.

Regarding the appearance it was surprisingly found that use of whey protein beverages wherein at least 85% w/w of the protein is BLG enables the possibility to increase the pH during thermal treatment, which provides improvements in visual perception (colour and turbidity) and in viscosity when compared to heat-treated WPI beverages. Thus, the present invention increases the pH range in which it is possible to make low viscous and preferably also transparent acidic beverages containing whey protein.

It has surprisingly been found that there is a significant difference in the sensory parameters between beverages produced with WPI compared to the BLG beverages of the present invention. It was found that, surprisingly and advantageously, the BLG beverage had a lower level of astringency, drying mouth-feeling, sourness, whey aroma and citric acid flavour compared to a WPI beverage. It was furthermore found that by increasing the pH of an acidic beverage less sweetener was required to balance out the acidity of the beverage and a lower concentration of sweetener is therefore required in such beverages.

In some preferred embodiments of the invention, the packaged, heat-treated beverage preparation has a pH in the range of 3.0-4.1, or preferably 3.1-4.0 or preferably 3.2-3.9, or preferably 3.7-3.9, more preferably 3.4-3.9, and even more preferably 3.5-3.9.

Therefore it is preferred that the liquid solution has a pH in the range of 3.0-4.1, or preferably 3.1-4.0 or preferably 3.2-3.9, or preferably 3.7-3.9, more preferably 3.4-3.9, and even more preferably 3.5-3.9.

The inventors have found that it is particularly difficult to make acidic protein beverages at a pH above pH 3.6, especially if the beverage should be transparent. The present invention, however, makes this possible.

Thus, the pH of the liquid solution may preferably be in the range of 3.7-4.3, more preferably in the range of 3.9-4.3, even more preferred in the range of 4.1-4.3.

Alternatively, but also preferred, the pH of the packaged, heat-treated beverage preparation may be in the range of 3.7-4.1, and more preferably in the range of 3.9-4.1.

These pH ranges are particularly relevant when the beverage preparation is pasteurised.

In some preferred embodiments of the invention, the liquid solution preferably has a pH in the range of 3.0-3.9, or preferably 3.2-3.7, or preferably 3.4-3.6 or preferably 3.5-3.7, or preferably 3.4-3.6.

These pH-ranges combined with high temperature treatment, such as sterilisation, are particularly relevant for production of transparent beverages having low viscosity and improved taste.

In some preferred embodiments of the invention, the liquid solution has a pH in the range of 4.1-4.7, this pH range is particularly relevant for the production of stable beverages having a milky appearance and a high turbidity while still having a low viscosity. In some embodiments of the invention, the pH range is of 4.2-4.6. In some other embodiments of the invention, the pH range is of 4.2-4.5.

In some preferred embodiments of the present invention the liquid solution comprises a total amount of protein of 4.0 to 35% w/w relative to the weight of the beverage, and preferably 4.0 to 30% w/w, more preferably 5.0 to 30% w/w.

In other preferred embodiments of the present invention the liquid solution comprises a total amount of protein of 5.0 to 45% w/w relative to the weight of the liquid solution, more preferably 5.0 to 35% w/w, even more preferably 5.0 to 34% w/w, and most preferred 5.0 to 32% w/w.

In some preferred embodiments of the invention, the liquid solution contains a protein content in an amount of at least 3-45% w/w, more preferably 11-40% w/w, even more preferably 15-38% w/w and most preferably 20-36% w/w.

In some embodiments of the invention, it is advantageous that the liquid solution has a protein content of 2.0 to 10.0% w/w relative to the weight of the solution.

Therefore, in some embodiments of the invention, the liquid solution, preferably comprises a total amount of protein of 2.0 to 10% w/w relative to the weight of the liquid solution, preferably a total amount of protein of 3.0 to 10% w/w relative to the weight of the liquid solution, preferably a total amount of protein of 5.0 to 9.0% w/w relative to the weight of the liquid solution, preferably a total amount of protein of 6.0 to 8.0% w/w relative to the weight of the liquid solution.

In some it is advantageous that the protein content of the liquid solution is high such as 10.0 to 45.0% w/w relative to the weight of the liquid solution.

Therefore in some embodiments of the present invention the liquid solution preferably comprises a total amount of protein of 10.0 to 45.0% w/w relative to the weight of the liquid solution, preferably a total amount of protein of 10.0 to 20% w/w relative to the weight of the liquid solution, preferably a total amount of protein of 12 to 30% w/w relative to the weight of the liquid solution, preferably a total amount of protein of 15 to 25% w/w relative to the weight of the liquid solution, preferably a total amount of protein of 18 to 20% w/w relative to the weight of the liquid solution.

In other preferred embodiments of the invention it is advantageous that the protein content of the liquid solution is 5.0 to 45.0% w/w relative to the weight of the liquid solution, preferably 6.0 to 35% w/w, more preferably 7.0 to 34% w/w, even more preferred 8.0-32% w/w, and most preferred 10-30% w/w.

The present invention surprisingly makes it possible to provide packaged, heat-treated beverage preparations having a protein content of and exceeding 15% w/w and even 20% w/w. Thus in some preferred embodiments of the invention, the liquid solution preferably comprises a total amount of protein of 15 to 45.0% w/w relative to the weight of the liquid solution, preferably a total amount of protein of 20 to 35% w/w relative to the weight of the liquid solution, more preferably a total amount of protein of 21 to 34% w/w relative to the weight of the liquid solution, and even more preferably a total amount of protein of 25 to 32% w/w relative to the weight of the liquid solution.

In other preferred embodiments of the invention, the liquid solution preferably comprises a total amount of protein of 21 to 35% w/w relative to the weight of the liquid solution, preferably a total amount of protein of 25 to 35% w/w relative to the weight of the liquid solution, more preferably a total amount of protein of 28 to 35% w/w relative to the weight of the liquid solution, and even more preferably a total amount of protein of 30 to 35% w/w relative to the weight of the liquid solution.

In further preferred embodiments of the invention, the liquid solution preferably comprises a total amount of protein of 21 to 33% w/w relative to the weight of the liquid solution, preferably a total amount of protein of 25 to 33% w/w relative to the weight of the liquid solution, and more preferably a total amount of protein of 28 to 33% w/w relative to the weight of the liquid solution.

The protein of the liquid solution is preferably prepared from mammal milk, and preferably from ruminant milk, such as e.g. milk from cow, sheep, goat, buffalo, camel, llama, mare and/or deer. Protein derived from bovine milk is particularly preferred. The protein of the liquid solution is therefore preferably bovine milk protein.

The protein of the liquid solution is preferably whey protein and/or milk serum protein and even more preferably bovine whey protein and/or milk serum protein.

In some preferred embodiments of the invention, the sum of alpha-lactalbumin (ALA) and caseinomacropeptide (CMP) comprises at least 40% w/w of the non-BLG protein of the liquid solution, preferably at least 60% w/w, even more preferably at least 70% w/w, and most preferably at least 90% w/w of the non-BLG protein of the liquid solution.

In other preferred embodiments of the invention, each main non-BLG whey protein is present in a weight percentage relative to total protein which is at most 25% of its weight percentage relative to total protein in a standard whey protein concentrate from sweet whey, preferably at most 20%, more preferably at most 15%, even more preferably at most 10%, most preferably at most 6%.

Even lower concentrations of the main non-BLG whey proteins may be desirable. Thus, in additional preferred embodiments of the invention, each main non-BLG whey protein is present in a weight percentage relative to total protein which is at most 4% of its weight percentage relative to total protein in a standard whey protein concentrate from sweet whey, preferably at most 3%, more preferably at most 2%, even more preferably at most 1%.

In some preferred embodiments of the invention, ALA comprises at most 80% w/w of the non-BLG protein of the liquid solution, preferably at most 60% w/w, even more preferably at most 40% w/w, and most preferably at most 30% w/w of the non-BLG protein of the liquid solution.

Even lower contents of ALA may be preferred, thus in some preferred embodiments of the invention, ALA comprises at most 20% w/w of the non-BLG protein of the liquid solution, preferably at most 15% w/w, even more preferably at most 10% w/w, and most preferably at most 5% w/w of the non-BLG protein of the liquid solution.

In some preferred embodiments of the invention, the liquid solution has a pH in the range of 3.0-3.9 and a total amount of protein of 10-34% w/w relative to the weight of the liquid solution, more preferably 12-30% w/w, and even more preferably 15-25% w/w.

In other preferred embodiments of the invention, the liquid solution has a pH in the range of 3.7-3.9 and a total amount of protein of 10-34% w/w relative to the weight of the liquid solution, more preferably 12-30% w/w, and even more preferably 15-25% w/w.

In further preferred embodiments of the invention, the liquid solution has:
a pH in the range of 3.0-3.9, preferably 3.7-3.9,
a total amount of protein of 10-34% w/w relative to the weight of the liquid solution, more preferably 12-30% w/w, and even more preferably 15-25% w/w, and
an intrinsic tryptophan fluorescence emission ratio (I330 nm/I350 nm) of at least 1.13, more preferably at least 1.15, even more preferably at least 1.17, and most preferably at least 1.19.

In even further preferred embodiments of the invention, the liquid solution has:
a pH in the range of 3.0-3.9, preferably 3.7-3.9,
a total amount of protein of 10-34% w/w relative to the weight of the liquid solution, more preferably 12-30% w/w, and even more preferably 15-25% w/w, and
a degree of protein denaturation of at most 10%, preferably at most 5% and even more preferably at most 1%.

As mentioned above, it was surprisingly found by the inventors that transparent heat-treated beverages comprising at least 85% w/w BLG can be produced even at a pH higher than pH 3.0 without the addition of an antiaggregant.

Therefore, in some preferred embodiments of the present invention, the liquid solution does not comprise any anti-aggregant or alternatively only traces of antiaggregant.

In some embodiments of the invention, the liquid solution comprises at most 0.1% w/w antiaggregant, preferably at most 0.03% w/w antiaggregant, and most preferably no antiaggregant. The embodiments are particularly preferred in relation to transparent, low fat beverages.

In some preferred embodiments of the invention, the liquid solution does not comprise polyphenol.

However, in other preferred embodiments of the invention, the liquid solution comprises polyphenols. Thus, it may be preferred that the liquid solution liquid solution comprises a total amount of polyphenol in the range of 0.01-1% w/w, more preferably 0.02-0.6% w/w, even more preferred 0.03-0.4% w/w, and more preferred in the range of 0.04-0.2% w/w.

In some preferred embodiments of the invention, the polyphenol at least comprises, and may even essentially consist of, EGCG.

It is particularly preferred that the liquid solution comprises a BLG isolate, e.g. in combination with other protein sources, preferably as the main protein source and possibly even as the only protein source.

The BLG isolate is preferably a BLG isolate powder or a liquid BLG isolate contain water and the solids of the BLG isolate powder in an amount in the range from 1-50% w/w.

The beta-lactoglobulin (BLG) isolate powder, preferably prepared by spray-drying, has a pH in the range of i) 2-4.9, ii) 6.1-8.5, or iii) 5.0-6.0 and comprises:
total protein in an amount of at least 30% w/w,
BLG in an amount of at least 85% w/w relative to total protein, and
water in an amount of at most 10% w/w.

The BLG isolate powder preferably has one or more of the following:
a bulk density of at least 0.2 g/cm$^3$,
an intrinsic tryptophan fluorescence emission ratio (I330/I350) of at least 1.11,
a degree of protein denaturation of at most 10%,
a heat-stability at pH 3.9 of at most 200 NTU, and
at most 1000 colony-forming units/g.

The BLG isolate powder is preferably an edible composition.

In some preferred embodiments of the invention, the BLG isolate powder has a pH in the range of 2-4.9. Such powders are particularly useful for acidic food products and particularly acidic beverages.

In other preferred embodiments of the invention, BLG isolate powder has a pH in the range of 6.1-8.5.

In some preferred embodiments of the invention, the BLG isolate powder comprises total protein in an amount of at least 40% w/w, preferably at least 50% w/w, at least 60% w/w, more preferably at least 70% w/w, even more preferably at least 80% w/w.

Even higher protein contents may be required and in some preferred embodiments of the invention, the BLG isolate powder comprises total protein in an amount of at least 85% w/w, preferably at least 90% w/w, at least 92% w/w, more preferably at least 94% w/w, and even more preferably at least 95% w/w.

Total protein is measured according to Example 1.5.

In some preferred embodiments of the invention, the BLG isolate powder comprises BLG in an amount of at least 92% w/w relative to total protein, preferably at least 95% w/w, more preferably at least 97% w/w, even more preferably at least 98%, and most preferably BLG in an amount of at least 99.5% w/w relative to total protein.

In some preferred embodiments of the invention, the sum of alpha-lactalbumin (ALA) and caseinomacropeptide (CMP) comprises at least 40% w/w of the non-BLG protein of the powder, preferably at least 60% w/w, even more preferably at least 70% w/w, and most preferably at least 90% w/w of the non-BLG protein of the powder.

In other preferred embodiments of the invention, each main non-BLG whey protein is present in a weight percentage relative to total protein which is at most 25% of its weight percentage relative to total protein in a standard whey protein concentrate from sweet whey, preferably at most 20%, more preferably at most 15%, even more preferably at most 10%, most preferably at most 6%.

Even lower concentrations of the main non-BLG whey proteins may be desirable. Thus, in additional preferred embodiments of the invention, each main non-BLG whey protein is present in a weight percentage relative to total protein which is at most 4% of its weight percentage relative to total protein in a standard whey protein concentrate from sweet whey, preferably at most 3%, more preferably at most 2%, even more preferably at most 1%.

The inventors have seen indications that reduction of lactoferrin and/or lactoperoxidase is particularly advantageous for obtaining a colour-neutral whey protein product.

Thus in some preferred embodiments of the invention, lactoferrin is present in a weight percentage relative to total protein which is at most 25% of its weight percentage relative to total protein in a standard whey protein concentrate from sweet whey, preferably at most 20%, more preferably at most 15%, even more preferably at most 10%, most preferably at most 6%. Even lower concentrations of lactoferrin may be desirable. Thus, in additional preferred embodiments of the invention, lactoferrin is present in a weight percentage relative to total protein which is at most 4% of its weight percentage relative to total protein in a standard whey protein concentrate from sweet whey, preferably at most 3%, more preferably at most 2%, even more preferably at most 1%.

Similarly, in some preferred embodiments of the invention, lactoperoxidase is present in a weight percentage relative to total protein which is at most 25% of its weight percentage relative to total protein in a standard whey protein concentrate from sweet whey, preferably at most 20%, more preferably at most 15%, even more preferably at most 10%, most preferably at most 6%. Even lower concentrations of lactoperoxidase may be desirable. Thus, in additional preferred embodiments of the invention, lactoperoxidase is present in a weight percentage relative to total protein which is at most 4% of its weight percentage relative to total protein in a standard whey protein concentrate from sweet whey, preferably at most 3%, more preferably at most 2%, even more preferably at most 1%.

Lactoferrin and lactoperoxidase are quantified according to Example 1.29.

In some preferred embodiments of the invention, the BLG isolate powder has a water content in an amount of at most 10% w/w, preferably at most 7% w/w, more preferably at most 6% w/w, even more preferably at most 4% w/w, and most preferred at most 2% w/w.

In some preferred embodiments of the invention, the BLG isolate powder comprises carbohydrate in an amount of at most 60% w/w, preferably at most 50% w/w, more preferably at most 20% w/w, even more preferably at most 10% w/w, even more preferably at most 1% w/w, and most preferably at most 0.1%. The BLG isolate powder may for example contain carbohydrates, such as e.g. lactose, oligosaccharides and/or hydrolysis products of lactose (i.e. glucose and galactose), sucrose, and/or maltodextrin.

In some preferred embodiments of the invention, the BLG isolate powder comprises lipid in an amount of at most 10% w/w, preferably at most 5% w/w, more preferably at most 2% w/w, and even more preferably at most 0.1% w/w.

The present inventors have found that it can be advantageous to control the mineral content to reach some of the desired properties of the BLG isolate powder.

In some preferred embodiments of the invention, the sum of the amounts of Na, K, Mg, and Ca of the BLG isolate powder is at most 10 mmol/g protein. Preferably, the sum of the amounts of Na, K, Mg, and Ca of the BLG isolate powder is at most 6 mmol/g protein, more preferably at most 4 mmol/g protein, even more preferably at most 2 mmol/g protein.

In other preferred embodiments of the invention, the the sum of the amounts of Na, K, Mg, and Ca of the BLG isolate powder is at most 1 mmol/g protein. Preferably, the sum of the amounts of Na, K, Mg, and Ca of the BLG isolate powder is at most 0.6 mmol/g protein, more preferably at most 0.4 mmol/g protein, even more preferably at most 0.2 mmol/g protein, and most preferably at most 0.1 mmol/g protein.

In other preferred embodiments of the invention, the sum of the amounts of Mg and Ca of the BLG isolate powder is at most 5 mmol/g protein. Preferably, the sum of the amounts of Mg and Ca of the BLG isolate powder is at most 3 mmol/g protein, more preferably at most 1.0 mmol/g protein, even more preferably at most 0.5 mmol/g protein.

In other preferred embodiments of the invention, the sum of the amounts of Mg and Ca of the BLG isolate powder is at most 0.3 mmol/g protein. Preferably, the sum of the amounts of Mg and Ca of the BLG isolate powder is at most 0.2 mmol/g protein, more preferably at most 0.1 mmol/g protein, even more preferably at most 0.03 mmol/g protein, and most preferably at most 0.01 mmol/g protein.

The inventors have found that it is possible to use low phosphorus/low potassium variants of the BLG isolate powder that are particularly useful to patients with kidney diseases. To make such a product, the BLG isolate powder has to have an equally low content of phosphorus and potassium.

Thus, in some preferred embodiments of the invention, the BLG isolate powder has a total content of phosphorus of at most 100 mg phosphorus per 100 g protein. Preferably, the BLG isolate powder has a total content of at most 80 mg phosphorus per 100 g protein. More preferably, the BLG isolate powder has a total content of at most 50 mg phosphorus per 100 g protein. Even more preferably, the BLG isolate powder has a total content of phosphorus of at most 20 mg phosphorus per 100 g protein. The BLG isolate powder has a total content of phosphorus of at most 5 mg phosphorus per 100 g protein.

In some preferred embodiments of the invention, the BLG isolate powder comprises at most 600 mg potassium per 100 g protein. More preferably, the BLG isolate powder comprise at most 500 mg potassium per 100 g protein. More preferably, the BLG isolate powder comprises at most 400 mg potassium per 100 g protein. More preferably, the BLG isolate powder comprises at most 300 mg potassium per 100 g protein. Even more preferably, the BLG isolate powder at most 200 mg potassium per 100 g protein. Even more preferably, the BLG isolate powder comprises at most 100 mg potassium per 100 g protein. Even more preferably, the BLG isolate powder comprises at most 50 mg potassium per 100 g protein and even more preferably, the BLG isolate powder comprises at most 10 mg potassium per 100 g protein.

The content of phosphorus relates to the total amount of elemental phosphorus of the composition in question and is determined according to Example 1.19. Similarly, the content of potassium relates to the total amount of elemental potassium of the composition in question and is determined according to Example 1.19.

In some preferred embodiments of the invention, the BLG isolate powder comprises at most 100 mg phosphorus/100 g protein and at most 700 mg potassium/100 g protein, preferably at most 80 mg phosphorus/100 g protein and at most 600 mg potassium/100 g protein, more preferably at most 60 mg phosphorus/100 g protein and at most 500 mg potassium/100 g protein, more preferably at most 50 mg phosphorus/100 g protein and at most 400 mg potassium/100 g protein, or more preferably at most 20 mg phosphorus/100 g protein and at most 200 mg potassium/100 g protein, or even more preferably at most 10 mg phosphorus/100 g protein and at most 50 mg potassium/100 g protein. In some preferred embodiments of the invention, the BLG isolate powder comprises at most 100 mg phosphor/100 g protein and at most 340 mg potassium/100 g protein.

The low phosphorus and/or low potassium compositions according to the present invention may be used as a food ingredient for the production of a food product for patients groups that have a reduced kidney function.

The present inventors have found that for some applications, e.g. acidic food products and particularly acidic beverages, it is particularly advantageous to have an acidic BLG isolate powder having a pH of at most 4.9 and even more preferably at most 4.3. This is especially true for high protein, transparent acidic beverages.

In the context of the present invention, a transparent liquid has a turbidity of at most 200 NTU measured according to Example 1.7.

Thus, in some preferred embodiments of the invention, the BLG isolate powder has a pH in the range of 2-4.9. Preferably, the BLG isolate powder has a pH in the range of 2.5-4.7, more preferably 2.8-4.3, even more preferably 3.2-4.0, and most preferably 3.4-3.9. Alternatively, but also preferred, the BLG isolate powder may have a pH in the range of 3.6-4.3.

The present inventors have found that for some applications, e.g. pH-neutral food products and particularly pH-neutral beverages, it is particularly advantageous to have a pH-neutral BLG isolate powder. This is especially true for high protein, transparent or opaque pH-neutral beverages.

Thus, in some preferred embodiments of the invention, BLG isolate powder has a pH in the range of 6.1-8.5. Preferably, the powder has a pH in the range of 6.1-8.5, more preferably 6.2-8.0, even more preferably 6.3-7.7, and most preferably 6.5-7.5.

In other preferred embodiments of the invention, BLG isolate powder has a pH in the range of 5.0-6.0. Preferably, the powder has a pH in the range of 5.1-5.9, more preferably 5.2-5.8, even more preferably 5.3-5.7, and most preferably 5.4-5.6.

Advantageously, the BLG isolate powder used in the present invention may have bulk density of at least 0.20 g/cm$^3$, preferably at least 0.30 g/cm$^3$, more preferably at least 0.40 g/cm$^3$, even more preferably at least 0.45 g/cm$^3$, even more preferably at least 0.50 g/cm$^3$, and most preferably at least 0.6 g/cm$^3$.

Low density powders such as freeze-dried BLG isolates are fluffy and easily drawn into the air of the production site during use. This is problematic as it increases the risk of cross-contamination of the freeze-dried powder to other foods products and a dusty environment is known to be a cause of hygiene issues. In extreme cases, a dusty environment also increases the risk of dust explosions.

The high density variants of the present invention are easier to handle and less prone to flow into the surrounding air.

An additional advantage of the high density variants of the present invention is that they take up less space during transportation and thereby increase weight of BLG isolate powder that can be transported in one volume unit.

Yet an advantage of the high density variants of the present invention is that they are less prone to segregation when used in powder mixtures with other powdered food ingredients, such as e.g. powdered sugar (bulk density of approx. 0.56 g/cm$^3$), granulated sugar (bulk density of approx. 0.71 g/cm$^3$), powdered citric acid (bulk density of approx. 0.77 g/cm$^3$).

The BLG isolate powder of the present invention may have bulk density in the range of 0.2-1.0 g/cm$^3$, preferably in the range of 0.30-0.9 g/cm$^3$, more preferably in the range of 0.40-0.8 g/cm$^3$, even more preferably in the range of 0.45-0.75 g/cm$^3$, even more preferably in the range of 0.50-0.75 g/cm$^3$, and most preferably in the range of 0.6-0.75 g/cm$^3$.

The bulk density of a powder is measured according to Example 1.17.

The present inventors have found that it is advantageous to maintain the native conformation of BLG and have seen indications that increased unfolding of BLG gives rise to an increased level of drying mouthfeel when the BLG is used for acidic beverages.

The intrinsic tryptophan fluorescence emission ratio (I330/I350) is a measure of degree of unfolding of BLG and the inventors have found that at high intrinsic tryptophan fluorescence emission ratios, which correlate with low or no unfolding of BLG, less drying mouthfeel was observed. The intrinsic tryptophan fluorescence emission ratio (I330/I350) is measured according to Example 1.1.

In some preferred embodiments of the invention, the BLG isolate powder has an intrinsic tryptophan fluorescence emission ratio (I330/I350) of at least 1.11.

In some preferred embodiments of the invention, the BLG isolate powder has an intrinsic tryptophan fluorescence emission ratio (I330/I350) of at least 1.12, preferably at least 1.13, more preferably at least 1.15, even more preferably at least 1.17, and most preferably at least 1.19.

If BLG isolate powder contains considerable amounts of non-protein matter it is preferred to isolate the protein fraction before measuring the intrinsic tryptophan fluorescence emission ratio. Thus in some preferred embodiments of the invention, the protein fraction of the BLG isolate powder has an intrinsic tryptophan fluorescence emission ratio of at least 1.11.

In some preferred embodiments of the invention, the protein fraction of the BLG isolate powder has an intrinsic tryptophan fluorescence emission ratio (I330/I350) of at least 1.12, preferably at least 1.13, more preferably at least 1.15, even more preferably at least 1.17, and most preferably at least 1.19.

The protein fraction can e.g. be separated from the BLG isolate powder by dissolving the BLG isolate powder in demineralised water and subjecting the solution to dialysis or ultrafiltration-based diafiltration using a filter that retains the protein. If the BLG isolate powder contains interfering levels of lipid such lipid can e.g. be removed by microfiltration. Steps of microfiltration and ultrafiltration/diafiltration can be combined to remove both lipid and small molecules from the protein fraction.

It is often preferred that a substantial amount of the BLG of the BLG isolate powder is non-aggregated BLG. Preferably at least 50% of the BLG is non-aggregated BLG. More preferably at least at least 80% of the BLG is non-aggregated BLG. Even more preferred at least 90% of the BLG is non-aggregated BLG. Most preferred, at least 95% of the BLG is non-aggregated BLG. Even more preferred approx. 100% of the BLG of the BLG isolate powder is non-aggregated BLG.

In some preferred embodiments of the invention, the BLG isolate powder has a degree of protein denaturation of at most 10%, preferably at most 8%, more preferably at most 6%, even more preferably at most 3%, even more preferably at most 1%, and most preferably at most 0.2%.

However, it may also be preferred that the BLG isolate powder has a significant level of protein denaturation, e.g. if an opaque beverage is desired. Thus, in other preferred embodiments of the invention, the BLG isolate powder has a degree of protein denaturation of at least 11%, preferably at least 20%, more preferably at least 40%, even more preferably at least 50%, even more preferably at least 75%, and most preferably at least 90%.

If BLG isolate powder has a significant level of protein denaturation it is often preferred to keep a low level of insoluble protein matter, i.e. precipitated protein matter that would settle in a beverage during storage. The level of insoluble matter is measure according to Example 1.10.

In some preferred embodiments of the invention, the BLG isolate powder comprises at most 20% w/w insoluble protein matter, preferably at most 10% w/w insoluble protein matter, more preferably at most 5% w/w insoluble protein matter, even more preferred at most 3% w/w insoluble protein matter, and most preferred at most 1% w/w insoluble protein matter. It may even be preferred that the BLG isolate powder does not contain any insoluble protein matter at all.

The present inventors have found that the heat-stability at pH 3.9 of a BLG isolate powder is a good indicator for its usefulness for transparent high protein beverages. The heat-stability at pH 3.9 is measured according to Example 1.2.

It is particularly preferred that the BLG isolate powder has a heat-stability at pH 3.9 of at most 200 NTU, preferably at most 100 NTU, more preferred at most 60 NTU, even more preferred at most 40 NTU, and most preferred at most 20 NTU. Even better heat-stabilities are possible and the BLG isolate powder preferably has a heat-stability at pH 3.9 of at most 10 NTU, preferably at most 8 NTU, more preferred at most 4 NTU, even more preferred at most 2 NTU.

The content of microorganisms of the BLG isolate powder is preferably kept to a minimum. However, it is a challenge to obtain both a high degree of protein nativeness and a low content of microorganism as processes for microbial reduction tend to lead to protein unfolding and denaturation. The present invention makes it possible to obtain a very low content of microorganism while at the same time maintain a high level of the nativeness of BLG.

Thus, in some preferred embodiments of the invention, the BLG isolate powder contains at most 15000 colony-forming units (CFU)/g. Preferably, the BLG isolate powder contains at most 10000 CFU/g. More preferably, the BLG isolate powder contains at most 5000 CFU/g. Even more preferably, the BLG isolate powder contains at most 1000 CFU/g. Even more preferably, the BLG isolate powder contains at most 300 CFU/g. Most preferably, the BLG isolate powder contains at most 100 CFU/g such as e.g. at most 10 CFU/g. In a particularly preferred embodiment the powder is sterile. A sterile BLG isolate powder may e.g. be prepared by combining several physical microbial reduction processes during the production of the BLG isolate powder, such as e.g. microfiltration and heat-treatment at acidic pH.

In some preferred embodiments of the invention, the BLG isolate powder has a pH in the range of i) 2-4.9, ii) 6.1-8.5, or iii) 5.0-6.0 and comprises:
total protein in an amount of at least 30% w/w, preferably at least 80% w/w, and even more preferably at least 90% w/w
beta-lactoglobulin (BLG) in an amount of at least 85% w/w relative to total protein, preferably at least 90% w/w,
water in an amount of at most 6% w/w,
lipid in an amount of at most 2% w/w, preferably at most 0.5% w/w,
said BLG isolate powder having:
an intrinsic tryptophan fluorescence emission ratio (I330/I350) of at least 1.11,
a degree of protein denaturation of at most 10%, and
a heat-stability at pH 3.9 of at most 200 NTU.

In some preferred embodiments of the invention, the BLG isolate powder has a pH in the range of i) 2-4.9 or ii) 6.1-8.5 and comprises:
total protein in an amount of at least 30% w/w, preferably at least 80% w/w, and even more preferably at least 90% w/w
beta-lactoglobulin (BLG) in an amount of at least 85% w/w relative to total protein, preferably at least 90% w/w, and more preferably at least 94% w/w relative to total protein
water in an amount of at most 6% w/w,
lipid in an amount of at most 2% w/w, preferably at most 0.5% w/w,
said BLG isolate powder having:
an intrinsic tryptophan fluorescence emission ratio (I330/I350) of at least 1.11,
a degree of protein denaturation of at most 10%, preferably at most 5%, and
a heat-stability at pH 3.9 of at most 70 NTU, preferably at most 50 NTU and even more preferably at most 40 NTU.

In some preferred embodiments of the invention, the BLG isolate powder has a pH in the range of i) 2-4.9 or ii) 6.1-8.5 and comprises:
total protein in an amount of at least 30% w/w,
beta-lactoglobulin (BLG) in an amount of at least 85% w/w relative to total protein, preferably at least 90% w/w, water in an amount of at most 6% w/w,
said BLG isolate powder having:
  a bulk density of at least 0.2 g/cm³,
  an intrinsic tryptophan fluorescence emission ratio (I330/I350) of at least 1.11,
  a degree of protein denaturation of at most 10%, and
  a heat-stability at pH 3.9 of at most 200 NTU.

In other preferred embodiments of the invention, the BLG isolate powder has a pH in the range of 2-4.9 and comprises:
  total protein in an amount of at least 80% w/w, preferably at least 90% w/w, and even more preferably at least 94% w/w
  beta-lactoglobulin (BLG) in an amount of at least 85% w/w relative to total protein, preferably at least 90% w/w, and even more preferably at least 94% w/w relative to total protein,
  water in an amount of at most 6% w/w,
  lipid in an amount of at most 2% w/w, preferably at most 0.5% w/w,
said BLG isolate powder having:
  a bulk density of at least 0.2 g/cm³, preferably at least 0.3 g/cm³, and more preferably at least 0.4 g/cm³,
  an intrinsic tryptophan fluorescence emission ratio (I330/I350) of at least 1.11,
  a degree of protein denaturation of at most 10%, preferably at most 5%, and more preferably at most 2%, and
  a heat-stability at pH 3.9 of at most 50 NTU, preferably at most 30 NTU and even more preferably at most 10 NTU.

In yet other preferred embodiments of the invention, the BLG isolate powder has a pH in the range of 6.1-8.5 and comprises:
  total protein in an amount of at least 80% w/w, preferably at least 90% w/w, and even more preferably at least 94% w/w
  beta-lactoglobulin (BLG) in an amount of at least 85% w/w relative to total protein, preferably at least 90% w/w, and even more preferably at least 94% w/w relative to total protein,
  water in an amount of at most 6% w/w,
  lipid in an amount of at most 2% w/w, preferably at most 0.5% w/w,
said BLG isolate powder having:
  a bulk density of at least 0.2 g/cm³, preferably at least 0.3 g/cm³, and more preferably at least 0.4 g/cm³,
  a degree of protein denaturation of at most 10%, preferably at most 5%, and more preferably at most 2%, and
  a heat-stability at pH 3.9 of at most 50 NTU, preferably at most 30 NTU, and even more preferably at most 10 NTU.

In further preferred embodiments of the invention, the BLG isolate powder has a pH in the range of 6.1-8.5 and comprises:
  total protein in an amount of at least 80% w/w, preferably at least 90% w/w, and even more preferably at least 94% w/w
  beta-lactoglobulin (BLG) in an amount of at least 85% w/w relative to total protein, preferably at least 90% w/w, and even more preferably at least 94% w/w relative to total protein,
  water in an amount of at most 6% w/w,
  lipid in an amount of at most 2% w/w, preferably at most 0.5% w/w,
said BLG isolate powder having:
  a bulk density of at least 0.2 g/cm³, preferably at least 0.3 g/cm³, and more preferably at least 0.4 g/cm³,
  a degree of protein denaturation of at most 10%, preferably at most 5%, and more preferably at most 2%, and
  a heat-stability at pH 3.9 of at most 50 NTU, preferably at most 30 NTU, and even more preferably at most 10 NTU.

In further preferred embodiments of the invention, the BLG isolate powder has a pH in the range of 5.0-6.0 and comprises:
  total protein in an amount of at least 80% w/w, preferably at least 90% w/w, and even more preferably at least 94% w/w,
  beta-lactoglobulin (BLG) in an amount of at least 85% w/w relative to total protein, preferably at least 90% w/w, and even more preferably at least 94% w/w relative to total protein,
  water in an amount of at most 6% w/w,
  lipid in an amount of at most 2% w/w, preferably at most 0.5% w/w,
said BLG isolate powder having:
  a bulk density of at least 0.2 g/cm³, preferably at least 0.3 g/cm³, and more preferably at least 0.4 g/cm³,
  a degree of protein denaturation of at most 10%, preferably at most 5%, and more preferably at most 2%,
  a heat-stability at pH 3.9 of at most 50 NTU, preferably at most 30 NTU, and even more preferably at most 10 NTU, and
  preferably, a BLG crystallinity of less than 10%.

The BLG isolate powder containing BLG in an amount of at least 85% w/w relative to total protein, is typically provided by a method comprising the steps of:
  a) providing a liquid BLG isolate having
    i) a pH in the range of 2-4.9,
    ii) a pH of in the range of 6.1-8.5, or
    iii) a pH of in the range of 5.0-6.0 said liquid BLG isolate containing BLG in an amount of at least 85 w/w relative to total protein,
  b) optionally, subjecting the liquid BLG isolate to a physical microbial reduction,
  c) drying the liquid BLG isolate, preferably by spray-drying.

The BLG isolate is preferably prepared from mammal milk, and preferably from ruminant milk such as e.g. milk from cow, sheep, goat, buffalo, camel, llama, mare and/or deer. Protein derived from bovine milk is particularly preferred. The BLG is therefore preferably bovine BLG.

The liquid BLG isolate may be provided in a number of different ways.

Typically, the provision of the liquid BLG isolate involves, or even consists of, isolating BLG from a whey protein feed to provide a BLG-enriched composition by one or more of the following methods:
  crystallisation or precipitation of BLG by salting-in,
  crystallisation or precipitation of BLG of BLG by salting-out,
  ion exchange chromatography, and
  fractionation of whey proteins by ultrafiltration.

A particularly preferred way of providing the BLG-enriched composition is by crystallisation of BLG, preferably by salting-in or alternatively by salting-out.

The whey protein feed is preferably a WPC, a WPI, an SPC, an SPI, or a combination thereof.

The term "whey protein feed" pertains to the composition from which the BLG-enriched composition and subsequently the liquid BLG isolate are derived.

In some embodiments of the invention, the preparation of the BLG-enriched composition includes, or even consist of, high salt BLG crystallisation in the pH range 3.6-4.0 according to U.S. Pat. No. 2,790,790 A1.

In other embodiments of the invention, the preparation of the BLG-enriched composition includes, or even consists of, the method described by de Jongh et al (Mild Isolation Procedure Discloses New Protein Structural Properties of β-Lactoglobulin, J Dairy Sci., vol. 84(3), 2001, pages 562-571) or by Vyas et al (Scale-Up of Native β-Lactoglobulin Affinity Separation Process, J. Dairy Sci. 85:1639-1645, 2002).

However, in particularly preferred embodiments of the invention, the BLG-enriched composition is prepared by crystallisation at pH 5-6 under salting-in conditions as described in the PCT application PCT/EP2017/084553, which is incorporated herein by reference for all purposes.

In some preferred embodiments of the invention, the BLG-enriched composition is an edible BLG composition according to PCT/EP2017/084553 containing at least 90% BLG relative to total protein and preferably containing BLG crystals.

If it does not already have the required characteristics to be used as liquid BLG isolate, the BLG-enriched composition which has been isolated from whey protein feed may be subjected to one or more steps selected from the group of:
demineralisation,
addition of minerals
dilution,
concentration,
physical microbioal reduction, and
pH adjustment
as part of providing the liquid BLG isolate.

Non-limiting examples of demineralisation include e.g. dialysis, gel filtration, UF/diafiltration, NF/diafiltration, and ion exchange chromatography.

Non-limiting examples of addition of minerals include addition of soluble, food acceptable salts, such as e.g. salts of Na, K, Ca, and/or Mg. Such salts may e.g. be phosphate-salts, chloride salts or salts of food acids, such as e.g. citrate salt or lactate salt. The minerals may be added in solid, suspended, or dissolved form.

Non-limiting examples of dilution include e.g. addition of liquid diluent such as water, demineralised water, or aqueous solutions of minerals, acids or bases.

Non-limiting examples of concentration include e.g. evaporation, reverse osmosis, nanofiltration, ultrafiltration and combinations thereof.

If the concentration has to increase the concentration of protein relative to total solids, it is preferred to use concentration steps such as ultrafiltration or alternatively dialysis. If the concentration does not have to increase the concentration of protein relative to total solids, methods such as e.g. evaporation, nanofiltration and/or reverse osmosis can be useful.

Non-limiting examples of physical microbial reduction include e.g. heat-treatment, germ filtration, UV radiation, high pressure treatment, pulsed electric field treatment, and ultrasound. These methods are well-known to the person skilled in the art.

Non-limiting examples of pH adjustment include e.g. addition of bases and/or acids, and preferably food acceptable bases and/or acids. It is particularly preferred to employ acids and/or bases that are capable of chelating divalent metal cations. Examples of such acids and/or bases are citric acid, citrate salt, EDTA, lactic acid, lactate salt, phosphoric acid, phosphate salt, and combinations thereof.

In some preferred embodiments of the present invention, the liquid solution has a colour value delta b* in the range of −0.10 to +0.51 at the CIELAB colour scale, particularly if the preparation has a turbidity of at most 200 NTU, and more preferably at most 40 NTU.

In other preferred embodiments of the invention, the liquid solution has a colour value delta b* in the range of 0.0 to 0.40 at the CIELAB colour scale, preferably in the range of +0.10 to +0.25.

The liquid solution of the present invention may comprise other macronutrients than proteins. In some embodiments of the invention, the liquid solution furthermore comprises carbohydrates. The total carbohydrate content in the liquid solution of the invention depends on the intended use of the final heat-treated beverage preparation.

In some preferred embodiments of the invention, the liquid solution furthermore comprises at least one source of carbohydrate. In one exemplary embodiment, the at least one source of carbohydrate is selected from the group consisting of: sucrose, maltodextrin, corn syrup solids, sucromalt, glucose polymers, corn syrup, modified starches, resistant starches, rice-derived carbohydrates, isomaltulose, white sugar, glucose, fructose, lactose, galactose, maltose, dextrose, high fructose corn syrup, honey, sugar alcohols, fructooligosaccharides, soy fiber, corn fiber, guar gum, konjac flour, polydextrose, Fibersol, and combinations thereof.

In some preferred embodiments of the invention, the liquid solution comprises sugar polymers, i.e. oligosaccharides and/or polysaccharides.

In some preferred embodiments the liquid solution furthermore comprises carbohydrates in a range between 0 to 95% of the total energy content of the liquid solution, preferably in a range between 10 to 85% of the total energy content of the liquid solution, preferably in a range between 20 to 75% of the total energy content of the liquid solution or preferably in a range between 30 to 60% of the total energy content of the liquid solution.

Even lower carbohydrate content is often preferred, thus in some preferred embodiments of the invention, the carbohydrate content of the liquid solution is preferably in a range between 0 to 30% of the total energy content of the preparation more preferably in a range between 0 to 20% of the total energy content of the preparation even more preferably in a range between 0 to 10% of the total energy content of the preparation.

In some preferred embodiments of the invention, the carbohydrate content of the liquid solution is at most 5% of the total energy content of the liquid solution, more preferably at most 1% of the total energy content of the liquid solution, and even more preferably at most 0.1% of the total energy content of the liquid solution.

In one embodiment of the invention, the liquid solution furthermore comprises at least one additional ingredient selected from the group consisting of vitamins, flavouring agent, minerals, sweeteners, antioxidants, food acid, lipids, carbohydrate, prebiotics, probiotics and non-whey protein.

In one embodiment of the invention, the liquid solution furthermore comprises at least one high intensity sweetener. In one embodiment, the at least one high intensity sweetener is selected from the group consisting of aspartame, cyclamate, sucralose, acesulfame salt, neotame, saccharin, stevia extract, a steviol glycoside such as e.g. rebaudioside A, or a combination thereof. In some embodiments of the invention, it is particularly preferred that the sweetener comprises or even consists of one or more high intensity sweeteners (HIS).

HIS are both found among both natural and artificial sweeteners and typically have a sweetening intensity of at least 10 times that of sucrose.

If used, the total amount of HIS is typically in the range of 0.01-2% w/w. For example, the total amount of HIS may be in the range of 0.05-1.5% w/w. Alternatively, the total amount of HIS may be in the range of 0.1-1.0% w/w.

The choice of the sweetener may depend on the beverage to be produced, e.g. high-intensity sweeteners (e.g. aspartame, acesulfame-K or sucralose) may be used in beverage where no energy contribution from the sweetener is desired, whereas for beverages having a natural profile natural sweeteners (e.g. steviol glycosides, sorbitol or sucrose) may be used.

Alternatively or additionally, a carbohydrate sweetener may be used.

It may furthermore be preferred that the sweetener comprises or even consists of one or more polyol sweetener(s). Non-limiting examples of useful polyol sweeteners are maltitol, mannitol, lactitol, sorbitol, inositol, xylitol, threitol, galactitol or combinations thereof. If used, the total amount of polyol sweetener is typically in the range of 1-20% w/w. For example, the total amount of polyol sweetener may be in the range of 2-15% w/w. Alternatively, the total amount of polyol sweetener may be in the range of 4-10% w/w.

The liquid solution of the present invention may comprise other macronutrients than proteins. In some embodiments of the invention, the liquid solution furthermore comprises lipids. The total lipid content in the final heat-treated beverage preparation of the invention depends on the intended use of the heat-treated beverage preparation.

In some preferred embodiments of the invention, the liquid solution has a lipid content between 0 to 60% of the total energy content of the liquid solution, or preferably in a range between 0 to 50% of the total energy content of the liquid solution, or preferably in a range between 0 to 45% of the total energy content of the liquid solution, or preferably in a range between 0 to 30% of the total energy content of the liquid solution or preferably in a range between 0 to 20% of the total energy content of the liquid solution or preferably in a range between 0 to 10% of the total energy content of the liquid solution or preferably in a range between 0 to 5% of the total energy content of the liquid solution.

The amount of lipid is determined according to ISO 1211:2010 (Determination of Fat Content—Röse-Gottlieb Gravimetric Method).

In some preferred embodiments of the invention, the lipid content of the liquid solution is at most 3% of the total energy content of the liquid solution, more preferably at most 1% of the total energy content of the liquid solution, and even more preferably at most 0.1% of the total energy content of the liquid solution.

The liquid solution typically contains a total amount of water in the range of 50-99% w/w, preferably in the range of 45-97% w/w, more preferably in the range of 40-95% w/w, even more preferably in the range of 35-90% w/w, and most preferably in the range of 30-85% w/w.

In some preferred embodiments of the invention, the liquid solution contains a total amount of water in the range of 55-90% w/w, preferably in the range of 57-85% w/w, more preferably in the range of 60-80% w/w, even more preferably in the range of 62-75% w/w, and most preferably in the range of 65-70% w/w.

In some preferred embodiments of the invention, the liquid solution contains a total amount of water in the range of 90-99% w/w, preferably in the range of 92-98.5% w/w, more preferably in the range of 94-98% w/w, even more preferably in the range of 95-98% w/w, and most preferably in the range of 96-98% w/w. These embodiments are e.g. useful for transparent, water-like beverages.

In some preferred embodiments of the invention, the liquid solution is non-alcoholic meaning that it contains at most 1.0% w/w ethanol, more preferably at most 0.5% w/w, even more preferably at most 0.1% w/w, and most preferably no detectable ethanol.

The liquid solution typically contains an amount of total solids in the range of 1-45% w/w, preferably in the range of 5-40% w/w, more preferably in the range of 10-35% w/w, even more preferably in the range of 12-30% w/w, and most preferably in the range of 16-25% w/w.

In some preferred embodiments of the invention, the liquid solution contains an amount of total solids in the range of 10-45% w/w, preferably in the range of 15-43% w/w, more preferably in the range of 20-40% w/w, even more preferably in the range of 25-38% w/w, and most preferably in the range of 30-35% w/w.

In some preferred embodiments of the invention, the liquid solution contains an amount of total solids in the range of 1-10% w/w, preferably in the range of 1.5-8% w/w, more preferably in the range of 2-6% w/w, even more preferably in the range of 2-5% w/w, and most preferably in the range of 2-4% w/w. These embodiments are e.g. useful for transparent, water-like beverages.

The part of the liquid solution that is not solids is preferably water.

The present inventors have found that it can be advantageous to control the mineral content to reach some of the desired properties of the packaged, heat-treated beverage preparation.

In some embodiments of the invention, the packaged, heat-treated beverage preparation comprises a plurality of minerals. In one exemplary embodiment, the liquid solution comprises at least four minerals. In one embodiment the four minerals are sodium, potassium, magnesium and calcium.

The present inventors have surprisingly found that when a BLG isolate is used as defined herein and in example 2, heat-treated beverage preparations having a high mineral concentration can be produced, without compromising the viscosity. This provides the possibility that packaged, heat-treated beverage preparations can be produced having a high mineral content and that beverages that are nutritionally complete nutritional supplements or nutritionally incomplete supplements can be produced.

In some preferred embodiments of the invention, the sum of the amounts of Na, K, Mg and Ca is within the range of 0 to 750 mM in the liquid solution, preferably within the range of 100-600 mM or preferably within the range of 200-500 mM.

In some preferred embodiments of the invention, the sum of the amounts of Na, K, Mg and Ca is at most 750 mM in the liquid solution.

In other preferred embodiments of the invention, the sum of the amounts of Na, K, Mg and Ca is at most 600 mM in the liquid solution, preferably at most 500 mM, or preferably at most 400 mM, or preferably at most 300 mM, or preferably at most 200 mM, preferably at most 170 mM, most preferably at most 150 mM, or preferably at most 130 mM, or preferably at most 100 mM or preferably at most 80 mM or preferably at most 60 mM or preferably at most 40 mM or preferably at most 30 mM or preferably at most 20 mM or preferably at most 10 mM or preferably at most 5 mM or preferably at most 1 mM.

In another exemplary embodiment, the liquid solution comprises a plurality of minerals selected from the group consisting of: Calcium, Iodine, Zinc, Copper, Chromium, Iron, Phosphorus, Magnesium, Selenium, Manganese, Molybdenum, Sodium, Potassium, and combinations thereof.

In some preferred embodiments of the present invention the liquid solution comprises at most 150 mM KCl and at most 150 mM CaCl2, or the liquid solution comprises at most 130 mM KCl and at most 130 mM CaCl2 or the liquid solution comprises at most 110 mM KCl and at most 110 mM CaCl2 or the liquid solution comprises at most 100 mM KCl and at most 100 mM CaCl2 or preferably the liquid solution comprises at most 80 mM KCl and at most 80 mM CaCl2 or preferably the liquid solution comprises at most 50 mM KCl and at most 50 mM CaCl2 or preferably the liquid solution comprises at most 40 mM KCl and at most 40 mM CaCl2.

In other preferred embodiments of the invention, the liquid solution is a low mineral beverage.

In the context of the present invention the term "low mineral" pertains to a composition, e.g. a liquid, beverage, a powder or another food product, that has at least one, preferably two, and even more preferably all, of the following:
  an ash content of at most 1.2% w/w relative to total solids,
  a total content of calcium and magnesium of at most 0.3% w/w relative to total solids,
  a total content of sodium and potassium of at most 0.10% w/w relative to total solids,
  a total content of phosphorus of at most 100 mg phosphorus per 100 g protein.

Preferably, a low mineral composition has at least one, preferably two or more, and even more preferably all, of the following:
  an ash content of at most 0.7% w/w relative to total solids,
  a total content of calcium and magnesium of at most 0.2% w/w relative to total solids,
  a total content of sodium and potassium of at most 0.08% w/w relative to total solids,
  a total content of phosphorus of at most 80 mg phosphorus per 100 g protein.

Even more preferably, a low mineral composition has at least one, preferably two or more, and even more preferably all, of the following:
  an ash content of at most 0.5% w/w relative to total solids,
  a total content of calcium and magnesium of at most 0.15% w/w relative to total solids,
  a total content of sodium and potassium of at most 0.06% w/w relative to total solids,
  a total content of phosphorus of at most 50 mg phosphorus per 100 g protein.

It is particularly preferred that a low mineral composition has the following:
  an ash content of at most 0.5% w/w relative to total solids,
  a total content of calcium and magnesium of at most 0.15% w/w relative to total solids,
  a total content of sodium and potassium of at most 0.06% w/w relative to total solids,
  a total content of phosphorus of at most 50 mg phosphorus per 100 g protein.

The present inventors have found that the present invention makes it possible to prepare a packaged, heat-treated beverage preparation having a very low content of phosphorus and other minerals such as Potassium, which is advantageous for patients suffering from kidney diseases or otherwise having a reduced kidney function.

The liquid solution is preferably a low phosphorus solution.

The liquid solution is preferably a low Potassium solution.

The liquid solution is preferably low phosphorus and a low Potassium solution.

In the context of the present invention the term "low phosphorus" pertains to a composition, e.g. a liquid, a powder or another food product, that has a total content of phosphorus of at most 100 mg phosphorus per 100 g protein. Preferably, a low phosphorus composition has a total content of at most 80 mg phosphorus per 100 g protein. More preferably, a low phosphorus composition may have a total content of at most 50 mg phosphorus per 100 g protein. Even more preferably, a low phosphorus composition may have a total content of phosphorus of at most 20 mg phosphorus per 100 g protein. Even more preferably, a low phosphorus composition may have a total content of phosphorus of at most 5 mg phosphorus per 100 g protein. Low phosphorus compositions according to the present invention may be used as a food ingredient for the production of a food product for patient groups that have a reduced kidney function.

Thus, in some particularly preferred embodiments of the invention, the liquid solution comprises at most 80 mg phosphorus per 100 g protein. Preferably, the liquid solution comprises at most 30 mg phosphorus per 100 g protein. More preferably, the liquid solution comprises at most 20 mg phosphorus per 100 g protein. Even more preferably, the liquid solution comprises at most 10 mg phosphorus per 100 g protein. Most preferably, the liquid solution comprises at most 5 mg phosphorus per 100 g protein.

The content of phosphorus relates to the total amount of elemental phosphorus of the composition in question and is determined according to Example 1.19.

In the context of the present invention the term "low potassium" pertains to a composition, e.g. a liquid, a powder or another food product, that has a total content of potassium of at most 700 mg potassium per 100 g protein. Preferably, a low phosphorus composition has a total content of at most 600 mg potassium per 100 g protein. More preferably, a low potassium composition may have a total content of at most 500 mg potassium per 100 g protein. More preferably, a low potassium composition may have a total content of potassium of at most 400 mg potassium per 100 g protein. More preferably, a low potassium composition may have a total content of potassium of at most 300 mg potassium per 100 g protein. Even more preferably, a low potassium composition may have a total content of potassium of at most 200 mg potassium per 100 g protein. Even more preferably, a low potassium composition may have a total content of potassium of at most 100 mg potassium per 100 g protein. Even more preferably, a low potassium composition may have a total content of potassium of at most 50 mg potassium per 100 g protein and even more preferably, a low potassium composition may have a total content of potassium of at most 10 mg potassium per 100 g protein.

Low potassium compositions according to the present invention may be used as a food ingredient for the production of a food product for patient groups that have a reduced kidney function.

Thus, in some particularly preferred embodiments of the invention, the liquid solution comprises at most 600 mg potassium per 100 g protein. More preferably, the liquid solution comprises at most 500 mg potassium per 100 g protein. More preferably, the liquid solution comprises at most 400 mg potassium per 100 g protein. More preferably, the liquid solution comprises at most 300 mg potassium per 100 g protein. Even more preferably, the liquid solution comprises at most 200 mg potassium per 100 g protein. Even more preferably, the liquid solution comprises at most 100 mg potassium per 100 g protein. Even more preferably, the liquid solution comprises at most 50 mg potassium per 100 g protein and even more preferably, the liquid solution comprises at most 10 mg potassium per 100 g protein The content of potassium relates to the total amount of elemental potassium of the composition in question and is determined according to Example 1.19.

In some preferred embodiments of the invention, the liquid solution comprises at most 100 mg phosphorus/100 g protein and at most 700 mg potassium/100 g protein, preferably at most 80 mg phosphorus/100 g protein and at most 600 mg potassium/100 g protein, more preferably at most 60 mg phosphorus/100 g protein and at most 500 mg potassium/100 g protein, more preferably at most 50 mg phosphorus/100 g protein and at most 400 mg potassium/100 g protein, or more preferably at most 20 mg phosphorus/100 g protein and at most 200 mg potassium/100 g protein, or even more preferably at most 10 mg phosphorus/100 g protein and at most 50 mg potassium/100 g protein. In some preferred embodiments of the invention, the packaged, heat-treated beverage preparation comprises at most 100 mg phosphor/100 g protein and at most 340 mg potassium/100 g protein.

The liquid solution comprising low amounts of phosphorus and Potassium may advantageously be supplemented with carbohydrates and lipids, the heat-treated beverage preparation preferably furthermore comprises a total amount of carbohydrates in a range between 30-60% of the total energy content of the liquid solution, preferably in a range between 35-50 E % and a total amount of lipid in the range of 20-60% of the total energy content, preferably in a range between 30-50 E %.

In one embodiment of the invention, the liquid solution comprises a plurality of vitamins. In one exemplary embodiment, the liquid solution comprises at least ten vitamins. In one exemplary embodiment, the liquid solution comprises a plurality of vitamins selected from the group consisting of: Vitamin A, vitamin B1, vitamin B2, vitamin B3, vitamin B5, vitamin B6, vitamin B7, vitamin B9, vitamin B12, vitamin C, vitamin D, vitamin K, Riboflavin, pantothenic Acid, vitamin E, thiamin, niacin, folic acid, biotin, and combinations thereof.

In one embodiment of the invention, the liquid solution comprises a plurality of vitamins and a plurality of minerals.

In some preferred embodiments of the present invention the liquid solution contains one or more food acids selected from the group consisting of citric acid, malic acid, tartaric acid, acetic acid, benzoic acid, butyric acid, lactic acid, fumaric acid, succinic acid, ascorbic acid, adipic acid, phosphoric acid, and mixtures thereof.

In an embodiment of the present invention, the liquid solution furthermore comprises a flavor selected from the group consisting of salt, flavorings, flavor enhancers and/or spices. In a preferred embodiment of the invention, the flavor comprises chocolate, cocoa, lemon, orange, lime, strawberry, banana, forest fruit flavor or combinations thereof. The choice of flavor may depend on the beverage to be produced.

An aspect of the invention pertains to the use of a protein solution comprising a total amount of protein of 2 to 45% w/w relative to the weight of the solution, preferably 3 to 35% w/w, wherein at least 85 w/w % of the protein is BLG, preferably at least 90% w/w, for controlling the turbidity of a heat-treated acidic beverage preparation having a pH in the range of 2.0-4.7.

Another aspect of the invention pertains to the use of a protein solution comprising a total amount of protein of 2 to 45% w/w relative to the weight of the solution, wherein at least 85 w/w % of the protein is BLG, preferably 90 w/w % for controlling the astringency of a heat-treated acidic beverage preparation having a pH in the range of 2.0-4.7.

Another aspect of the invention pertains to a packaged, heat-treated beverage preparation as defined herein, for use in a method for the treatment of diseases associated with protein malabsorption.

Another aspect of the invention pertains to use of the packaged, heat-treated beverage preparation as defined herein as a dietary supplement.

In a preferred embodiment of the invention, the packaged, heat-treated beverage preparation as defined herein is used as a dietary supplement and it is ingested before, during or after exercise.

In a preferred embodiment of the present invention the packaged, heat-treated beverage preparation has a pH in the range of 2.0-4.2, preferably 3.0-3.9 or preferably 3.2-3.7, the beverage comprising
  a total amount of protein of 2 to 45% w/w relative to the weight of the beverage, wherein at least 85% w/w of the protein is BLG, preferably at least 90% w/w, and
  optionally, sweetener and/or flavour,
  wherein:
    the protein fraction of the beverage preparation has an intrinsic tryptophan fluorescence emission ratio (I330 nm/I350 nm) of at least 1.11
    a lipid content of at most 5% of the total energy content of the preparation.

In a preferred embodiment of the present invention the packaged, heat-treated beverage preparation has a pH in the range of 2.0-4.2, preferably 3.0-3.9 or preferably 3.2-3.7, the beverage comprising
  a total amount of protein of 2 to 10% w/w relative to the weight of the beverage, wherein at least 85% w/w of the protein is BLG, preferably at least 90% w/w, and
    optionally, sweetener and/or flavour,
    wherein:
    the protein fraction of the beverage preparation has an intrinsic tryptophan fluorescence emission ratio (I330 nm/I350 nm) of at least 1.11
    a lipid content of at most 5% of the total energy content of the preparation.

In a preferred embodiment of the present invention the packaged, heat-treated beverage preparation has a pH in the range of 2.0-4.2, preferably 3.0-3.9 or preferably 3.2-3.7 the beverage comprising
  a total amount of protein of 10 to 45% w/w relative to the weight of the beverage, preferably 10-35% w/w, wherein at least 85% w/w of the protein is BLG, preferably at least 90% w/w, and
    optionally, sweetener and/or flavour,
    wherein:
    the protein fraction of the beverage preparation has an intrinsic tryptophan fluorescence emission ratio (I330 nm/I350 nm) of at least 1.11
    a lipid content of at most 5% of the total energy content of the preparation.

In a preferred embodiment of the present invention the packaged, heat-treated beverage preparation has a pH in the range of 2.0-4.2, preferably 3.0-3.9 or preferably 3.2-3.7, the beverage comprising
  a total amount of protein of 2 to 45% w/w relative to the weight of the beverage, wherein at least 85% w/w of the protein is BLG, preferably at least 90% w/w, and optionally, sweetener and/or flavour, the packaged, heat-treated beverage preparation has a turbidity of at most 200 NTU, preferably at most 40 NTU.

In other preferred embodiments of the present invention, the packaged, heat-treated beverage preparation has a pH in the range of 2.0-4.2, preferably 3.0-3.9 or preferably 3.2-3.7, the beverage comprising:

a total amount of protein of 2 to 45% w/w relative to the weight of the beverage, wherein at least 85% w/w of the protein is BLG, preferably at least 90% w/w, and optionally, sweetener and/or flavour, the packaged, heat-treated beverage preparation has a turbidity of at most 200 NTU, preferably at most 40 NTU.

In yet preferred embodiments of the present invention, the packaged, heat-treated beverage preparation has a pH in the range of 3.5-4.7, preferably 3.7-4.3, and even more preferably 3.7-4.1, the beverage preparation comprising:

a total amount of protein of 2 to 45% w/w relative to the weight of the beverage, preferably 5.0-35%, and more preferably 6.0-32% w/w, at least 88% w/w of the protein is BLG, preferably at least 90% w/w, and more preferably at least 92% w/w a total amount of lipid of at most 5% w/w, preferably at most 1% % w/w and even more preferably at most 0.2% w/w, optionally, sweetener and/or flavour, the beverage preparation having:

a viscosity of at most 100 cP, preferably at most 20 cP and more preferably at most 10 cP, an intrinsic tryptophan fluorescence emission ratio (I330 nm/I350 nm) of at least 1.13, preferably at least 1.15 and more preferably at least 1.16, and optionally, a turbidity of at most 50 NTU, preferably at most 20 NTU, and more preferably at most 10 NTU.

In a preferred embodiment of the present invention the packaged, heat-treated beverage preparation has a pH in the range of 2.0-4.2, preferably 3.0-3.9 or preferably 3.2-3.7 the beverage comprising a total amount of protein of 2 to 10% w/w relative to the weight of the beverage, wherein at least 85% w/w of the protein is BLG, preferably at least 90% w/w, and optionally, sweetener and/or flavour, the packaged, heat-treated beverage preparation has a turbidity of at most 200 NTU, preferably at most 40 NTU.

In a preferred embodiment of the present invention the packaged, heat-treated beverage preparation has a pH in the range of 2.0-4.2, preferably 3.0-3.9 or preferably 3.2-3.7 the beverage comprising a total amount of protein of 10 to 45% w/w relative to the weight of the beverage, preferably 10-20% w/w, wherein at least 85% w/w of the protein is BLG, preferably at least 90% w/w, and optionally, sweetener and/or flavour, the packaged, heat-treated beverage preparation has a turbidity of at most 200 NTU, preferably at most 40 NTU.

In a preferred embodiment of the present invention the packaged, heat-treated beverage preparation has a pH in the range of 2.0-4.2, preferably 3.0-3.9 or preferably 3.2-3.7, the beverage comprising a total amount of protein of 2 to 45% w/w relative to the weight of the beverage, wherein at least 85% w/w of the protein is BLG, preferably at least 90% w/w, and optionally, sweetener and/or flavour, wherein:

the protein fraction of the beverage preparation has an intrinsic tryptophan fluorescence emission ratio (I330 nm/I350 nm) of at least 1.11 the protein fraction of the beverage preparation has a colour value delta b* in the range of −0.10 to +0.51 at the CIELAB colour scale, wherein delta b*= $b_{sample\ standardized\ to\ 6.0\ w/w\ \%\ protein}^{*} - b_{demin.\ water}^{*}$, measured at room temperature.

In a preferred embodiment of the present invention the packaged, heat-treated beverage preparation has a pH in the range of 2.0-4.2, preferably 3.0-3.9 or preferably 3.2-3.7, the beverage comprising a total amount of protein of 2 to 10% w/w relative to the weight of the beverage, wherein at least 85% w/w of the protein is BLG, preferably at least 90% w/w, and optionally, sweetener and/or flavour, wherein:

the protein fraction of the beverage preparation has an intrinsic tryptophan fluorescence emission ratio (I330 nm/I350 nm) of at least 1.11 the protein fraction of the beverage preparation has a colour value delta b* in the range of −0.10 to +0.51 at the CIELAB colour scale, wherein delta b*= $b_{sample\ standardized\ to\ 6.0\ w/w\ \%\ protein}^{*} - b_{demin.\ water}^{*}$, measured at room temperature.

In a preferred embodiment of the present invention the packaged, heat-treated beverage preparation has a pH in the range of 2.0-4.2, preferably 3.0-3.9 or preferably 3.2-3.7, the beverage comprising a total amount of protein of 10 to 45% w/w relative to the weight of the beverage, preferably 10-20% w/w, wherein at least 85% w/w of the protein is BLG, preferably at least 90% w/w, and optionally, sweetener and/or flavour, wherein:

the protein fraction of the beverage preparation has an intrinsic tryptophan fluorescence emission ratio (I330 nm/I350 nm) of at least 1.11 the protein fraction of the beverage preparation has a colour value delta b* in the range of −0.10 to +0.51 at the CIELAB colour scale, wherein delta b*= $b_{sample\ standardized\ to\ 6.0\ w/w\ \%\ protein}^{*} - b_{demin.\ water}^{*}$, measured at room temperature.

In a preferred embodiment of the present invention the packaged, heat-treated beverage preparation has a pH in the range of 2.0-4.2, preferably 3.0-3.9 or preferably 3.2-3.7, the beverage comprising a total amount of protein of 2 to 45% w/w relative to the weight of the beverage, wherein at least 85% w/w of the protein is BLG, preferably at least 90% w/w, and optionally, sweetener and/or flavour, wherein:

the protein fraction of the beverage preparation has an intrinsic tryptophan fluorescence emission ratio (I330 nm/I350 nm) of at least 1.11 the sum of the amounts of Na, K, Mg and Ca is at most 750 mM, preferably at most 400 mM, preferably at most 200 mM.

In a preferred embodiment of the present invention the packaged, heat-treated beverage preparation has a pH in the range of 2.0-4.2, preferably 3.0-3.9 or preferably 3.2-3.7, the beverage comprising a total amount of protein of 2 to 10% w/w relative to the weight of the beverage, wherein at least 85% w/w of the protein is BLG, preferably at least 90% w/w, and optionally, sweetener and/or flavour, wherein:

the protein fraction of the beverage preparation has an intrinsic tryptophan fluorescence emission ratio (I330 nm/I350 nm) of at least 1.11 the sum of the amounts of Na, K, Mg and Ca is at most 750 mM, preferably at most 400 mM, preferably at most 200 mM.

In a preferred embodiment of the present invention the packaged, heat-treated beverage preparation has a pH in the range of 2.0-4.2, preferably 3.0-3.9 or preferably 3.2-3.7, the beverage comprising a total amount of protein of 10 to 45% w/w relative to the weight of the beverage, preferably 10-20% w/w, wherein at least 85% w/w of the protein is BLG, preferably at least 90% w/w, and optionally, sweetener and/or flavour, wherein:

the protein fraction of the beverage preparation has an intrinsic tryptophan fluorescence emission ratio (I330 nm/I350 nm) of at least 1.11 the sum of the amounts of Na, K, Mg and Ca is at most 750 mM, preferably at most 400 mM, preferably at most 200 mM.

In a preferred embodiment of the present invention the packaged, heat-treated, opaque beverage preparation has a pH in the range of 3.0-4.7, preferably 3.9-4.6, more preferably 4.0-4.5, the beverage comprising:

a total amount of protein of 2 to 45% w/w relative to the weight of the beverage, wherein at least 85% w/w of the protein is BLG, preferably at least 90% w/w, and optionally, sweetener and/or flavour, wherein:

the protein fraction of the beverage preparation has an intrinsic tryptophan fluorescence emission ratio (I330 nm/I350 nm) of at least 1.11 and/or wherein the protein fraction has a degree of protein denaturation of at most 5% and/or a lipid content of more than 5% of the total energy content of the preparation.

In a preferred embodiment of the present invention the packaged, heat-treated beverage preparation has a pH in the range of 3.0-4.7, preferably 3.9-4.6, more preferably 4.0-4.5, the beverage comprising:

a total amount of protein of 2 to 45% w/w relative to the weight of the beverage, wherein at least 85% w/w of the protein is BLG preferably at least 90% w/w, and optionally, sweetener and/or flavour, wherein:

the turbidity is more than 200 NTU, preferably more than 1000 NTU and/or the viscosity is at most 200 cP.

In a preferred embodiment of the present invention the packaged, heat-treated, opaque beverage preparation has a pH in the range of 3.0-4.7, preferably 3.9-4.6, more preferably 4.0-4.5, the beverage comprising:

a total amount of protein of 2 to 10% w/w relative to the weight of the beverage, wherein at least 85% w/w of the protein is BLG, preferably at least 90% w/w, and optionally, sweetener and/or flavour, wherein:

the protein fraction of the beverage preparation has an intrinsic tryptophan fluorescence emission ratio (I330 nm/I350 nm) of at least 1.11 and/or wherein the protein fraction has a degree of protein denaturation of at most 5% and/or a lipid content of more than 5% of the total energy content of the preparation.

In a preferred embodiment of the present invention the packaged, heat-treated beverage preparation has a pH in the range of 3.0-4.7, preferably 3.9-4.6, more preferably 4.0-4.5, the beverage comprising:

a total amount of protein of 2 to 10% w/w relative to the weight of the beverage, wherein at least 85% w/w of the protein is BLG preferably at least 90% w/w, and optionally, sweetener and/or flavour, wherein:

the turbidity is more than 200 NTU, preferably more than 1000 NTU and/or the viscosity is at most 200 cP.

In a preferred embodiment of the present invention the packaged, heat-treated, opaque beverage preparation has a pH in the range of 3.0-4.7, preferably 3.9-4.6, more preferably 4.0-4.5, the beverage comprising:

a total amount of protein of 10 to 45% w/w relative to the weight of the beverage, preferably 10-20% w/w, wherein at least 85% w/w of the protein is BLG, preferably at least 90% w/w, and optionally, sweetener and/or flavour, wherein:

the protein fraction of the beverage preparation has an intrinsic tryptophan fluorescence emission ratio (I330 nm/I350 nm) of at least 1.11 and/or wherein the protein fraction has a degree of protein denaturation of at most 5% and/or a lipid content of more than 5% of the total energy content of the preparation.

In a preferred embodiment of the present invention the packaged, heat-treated beverage preparation has a pH in the range of 3.0-4.7, preferably 3.9-4.6, more preferably 4.0-4.5, the beverage comprising a total amount of protein of 10 to 45% w/w relative to the weight of the beverage, wherein at least 85% w/w of the protein is BLG preferably at least 90% w/w, and optionally, sweetener and/or flavour, wherein:

the turbidity is more than 200 NTU, preferably more than 1000 NTU and/or the viscosity is at most 200 cP.

In a preferred embodiment of the present invention, the packaged, heat-treated beverage preparation has a pH in the range of 2.0-4.2, preferably 3.0-3.9 or preferably 3.2-3.7, the beverage comprising:

a total amount of protein of 5 to 34% w/w relative to the weight of the beverage, wherein at least 85% w/w of the protein is BLG, preferably at least 90% w/w, and optionally, sweetener and/or flavour, wherein:

the protein fraction of the beverage preparation has an intrinsic tryptophan fluorescence emission ratio (I330 nm/I350 nm) of at least 1.13 a lipid content of at most 5% of the total energy content of the preparation.

In a preferred embodiment of the present invention, the packaged, heat-treated beverage preparation has a pH in the range of 2.0-4.7, preferably 3.0-3.9 or preferably 3.2-3.7, the beverage comprising:

a total amount of protein of 5 to 10% w/w relative to the weight of the beverage, wherein at least 85% w/w of the protein is BLG, preferably at least 90% w/w, and optionally, sweetener and/or flavour, wherein:
the protein fraction of the beverage preparation has an intrinsic tryptophan fluorescence emission ratio (I330 nm/I350 nm) of at least 1.13,
a lipid content of at most 5% of the total energy content of the preparation.

In a preferred embodiment of the present invention the packaged, heat-treated beverage preparation has a pH in the range of 3.7-4.3, preferably 3.9-4.3 or preferably 4.1-4.3, the beverage comprising:
a total amount of protein of 5 to 10% w/w relative to the weight of the beverage, wherein at least 85% w/w of the protein is BLG, preferably at least 90% w/w, and optionally, sweetener and/or flavour,
wherein:
the protein fraction of the beverage preparation has an intrinsic tryptophan fluorescence emission ratio (I330 nm/I350 nm) of at least 1.13
a lipid content of at most 5% of the total energy content of the preparation.

In a preferred embodiment of the present invention the packaged, heat-treated beverage preparation has a pH in the range of 3.7-4.3, preferably 3.9-4.3 or preferably 4.1-4.3, the beverage comprising:
a total amount of protein of 10 to 35% w/w relative to the weight of the beverage, wherein at least 85% w/w of the protein is BLG, preferably at least 90% w/w, and optionally, sweetener and/or flavour,
wherein:
the protein fraction of the beverage preparation has an intrinsic tryptophan fluorescence emission ratio (I330 nm/I350 nm) of at least 1.13
a lipid content of at most 5% of the total energy content of the preparation.

In some embodiments of the invention, the heat-treated beverage has a shelf-life at 25 degrees C. for at least 6 months, which comprises:
an edible BLG composition as defined in PCT/EP2017/084553 to provide at total amount of BLG of at least 1% (w/w), preferably at least 5% (w/w),
a sweetener, e.g. a sugar sweetener and/or a non-sugar sweetener,
at least one food acid, e.g. citric acid or other suitable food acids,
optionally, a flavouring agent, and
at most 80 mg phosphorus/100 g protein
which has a pH in the range of 2.5-4.0.

In a preferred embodiment of the present invention it relates to use of a protein solution comprising a total amount of protein of 3 to 30% w/w relative to the weight of the solution, wherein at least 85 w/w % of the protein is BLG, preferably at least 90 w/w % for controlling the turbidity of a heat-treated acidic beverage preparation having a pH in the range of 3.0-4.5.

In a preferred embodiment of the present invention it relates to use of a protein solution comprising a total amount of protein of 3 to 30% w/w relative to the weight of the solution, wherein at least 85 w/w % of the protein is BLG, preferably at least 90 w/w % for controlling the astringency of a heat-treated acidic beverage preparation having a pH in the range of 2.0-4.0.

A preferred embodiment of the invention, pertains to a heat-treated beverage preparation obtainable by one or more methods described herein.

It should be noted that the embodiments and features described in the context of one of the aspects of the present invention also apply to the other aspects of the invention.

All patent and non-patent references cited in the present application are hereby incorporated by reference in their entirety.

The invention will now be described in further details in the following non-limiting examples.

EXAMPLES

Example 1: Methods of Analysis

Example 1.1: Determination of Protein Nativeness by Intrinsic Tryptophan Fluorescence Tryptophan (Trp) fluorescence spectroscopy is a well-described tool to monitor protein folding and unfolding. Trp residues buried within native proteins typically display highest fluorescence emission around 330 nm than when present in more solvent exposed positions such as unfolded proteins. In unfolded proteins, the wavelengths for Trp fluorescence emission typically shift to higher wavelengths and are often measured around 350 nm. We here exploit this transition to monitor thermally induced unfolding by calculating the ratio between fluorescence emission at 330 nm and 350 nm to investigate the influence of heating temperature.

The analysis comprises the following steps:
Beverage compositions were diluted to 0.6 mg/ml in MQ water.
300 µl sample was transferred to white 96-well plate avoiding bubbles or 3 mL was transferred to 10 mm quartz cuvette.
The tryptophan fluorescence emission intensity between 310 and 400 nm was recorded from the top by excitation at 295 using 5 nm slits.
Samples were measured at 22° C. using a Cary Eclipse fluorescence spectrophotometer equipped with a plate reader accessory (G9810A) or single cuvette holder.
The emission intensity ratio was calculated by dividing the measured fluorescence emission intensity at 330 nm with the emission intensity at 350 nm, R=I330/I350, and used as a measure of protein nativity.
R of at least 1.11 describes a predominant native BLG conformation and
R of less than 1.11 reports on at least partial unfolding and aggregation.

Example 1.2: Heat-Stability at pH 3.9

Heat-Stability at pH 3.9:
The heat-stability at pH 3.9 is a measure of the ability of protein composition to stay clear upon prolonged pasteurization at pH 3.9.

The heat-stability at pH 3.9 is determined by forming an aqueous solution having a pH of 3.9 and comprising 6.0% w/w protein by mixing a sample of the powder or liquid to be tested with water (or alternatively concentrating it by low temperature evaporation if it is a dilute liquid) and adjusting the pH to 3.9 with the minimum amount of 0.1 M NaOH or 0.1 M HCl required.

The pH-adjusted mixture is allowed to rest for 30 minutes after which 25 mL of the mixture is transferred to a 30 mL thin-walled glass test tube. It is heated to 75.0 degrees C. for 300 seconds by immersion into a water-bath having a temperature of 75.0 degrees C. Immediately after the heating, the glass test tube is cooled to 1-5 degrees C. by transferring it to an ice bath and the turbidity of the heat-treated sample is measured according to Example 1.7.

Example 1.3: Determination of the Degree of Protein Denaturation of a Whey Protein Composition Denatured whey protein is known to have a lower solubility at pH 4.6 than at pH values below or above pH 4.6, therefore the degree of denaturation of a whey protein composition is determined by measuring the amount of soluble protein at pH 4.6 relative to the total amount of protein at a pH where the proteins in the solution are stable.

More specifically for whey proteins, the whey protein composition to be analysed (e.g. a powder or an aqueous solution) is converted to:

a first aqueous solution containing 5.0% (w/w) total protein and having a pH of 7.0 or 3.0, and a second aqueous solution containing 5.0% (w/w) total protein and having a pH of 4.6.

pH adjustments are made using 3% (w/w) NaOH (aq) or 5% (w/w) HCl (aq).

The total protein content ($P_{pH\ 7.0\ or\ 3.0}$) of the first aqueous solution is determined according to example 1.5.

The second aqueous solution is stored for 2 h at room temperature and subsequently centrifuged at 3000 g for 5 minutes. A sample of the supernatant is recovered and analysed according to Example 1.5 to give the protein concentration in the supernatant ($S_{pH\ 4.6}$).

The degree of protein denaturation, D, of the whey protein composition is calculated as:

$$D=((P_{pH\ 7.0\ or\ 3.0}-S_{pH\ 4.6})/P_{pH\ 7.0\ or\ 3.0})*100\%$$

Example 1.4 Determination of Protein Denaturation (with pH 4.6 Acid Precipitation) Using Reverse Phase UPLC Analysis BLG samples (such as non-heated reference and heated BLG beverage compositions) were diluted to 2% in MQ water. 5 mL protein solution, 10 mL Milli-Q, 4 mL 10% acetic acid and 6 mL 1.0M NaOAc are mixed and stirred for 20 minutes to allow precipitation agglomeration of denatured protein around pH 4.6. The solution is filtered through 0.22 μm filter to remove agglomerates and non-native proteins.

All samples were subjected to the same degree of dilution by adding polished water.

For each sample, the same volume was loaded on an UPLC system with a UPLC column (Protein BEH C4; 300 Å; 1.7 μm; 150×2.1 mm) and detected at 214 nm.

The samples were run using the following conditions:

Buffer A: Milli-Q water, 0.1% w/w TFA

Buffer B: HPLC grade acetonitrile, 0.1% w/w TFA

Flow: 0.4 ml/min

Gradient: 0-6.00 minutes 24-45% B; 6.00-6.50 minutes 45-90% B; 6.50-7.00 minutes 90% B; 7.00-7.50 minutes 90-24% B and 7.50-10.00 minutes 24% B.

The area of BLG peaks against a protein standard (Sigma L0130) was used to determine the concentration of native bLG in samples (5 level calibration curve) Samples were diluted further and reinjected if outside linear range.

Example 1.5: Determination Total Protein

The total protein content (true protein) of a sample is determined by:

1) Determining the total nitrogen of the sample following ISO 8968-1/2|DF 020-1/2—Milk—Determination of nitrogen content—Part 1/2: Determination of nitrogen content using the Kjeldahl method.

2) Determining the non-protein nitrogen of the sample following ISO 8968-4|DF 020-4—Milk—Determination of nitrogen content—Part 4: Determination of non-protein-nitrogen content.

3) Calculating the total amount protein as ($m_{total\ nitrogen} - m_{non-protein-nitrogen}$)*6.38.

Example 1.6: Determination of Non-Aggregated BLG, ALA, and CMP

The content of non-aggregated alpha-lactalbumin (ALA), beta-lactoglobulin (BLG) and caseinomacropeptide (CMP), respectively was analysed by HPLC analysis at 0.4 mL/min. 25 microL filtered sample is injected onto 2 TSKgel3000PWxl (7.8 mm 30 cm, Tosohass, Japan) columns connected in series with attached pre-column PWxl (6 mm×4 cm, Tosohass, Japan) equilibrated in the eluent (consisting of 465 g Milli-Q water, 417.3 g acetonitrile and 1 mL triflouroacetic acid) and using a UV detector at 210 nm.

Quantitative determination of the contents of native alpha-lactalbumin ($C_{alpha}$), beta-lactoglobulin ($C_{beta}$), and caseinomacropeptide ($C_{CMP}$) was performed by comparing the peak areas obtained for the corresponding standard proteins with those of the samples.

The total amount of additional protein (non-BLG protein) was determined by subtracting the amount of BLG from the amount of total protein (determined according to Example 1.5)

Example 1.7: Determination of Turbidity

Turbidity is the cloudiness or haziness of a fluid caused by large number of particles that are generally invisible to the naked eye, similar to smoke in air.

Turbidity is measured in nephelometric turbidity units (NTU).

20 mL beverages/samples were added to NTU-glass and placed in the Turbiquant® 3000 IR Turbidimeter. The NTU-value was measured after stabilisation and repeated twice.

Example 1.8: Determination of Viscosity

The viscosity of beverage preparations was measured using a Rheometer (Anton Paar, Physica MCR301).

3.8 mL sample was added to cup DG26.7. Samples were equilibrated to 22° C., then pre-sheared for 30 sec. at 50 s$^{-1}$, followed by a 30 sec. equilibration time and shear rate sweeps between 1 s$^{-1}$ and 200 s$^{-1}$ and 1 s$^{-1}$ were performed.

The viscosity is presented in the unit centipoise (cP) at a shear rate of 100 s$^{-1}$ unless otherwise stated. The higher the measured cP values, the higher the viscosity.

Alternatively, the viscosity was estimated using a Viscoman by Gilson and reported at a shear rate of about 300 s$^{-1}$

Example 1.9: Determination of Colour

The colour was measured using a Chroma Meter (Konica Minolta, CR-400). 15 g sample was added to a small petri dish (55×14.2 mm, VWR Cat #391-0895) avoiding bubble formation. The protein content of the samples was standardised to 6.0 w/w % protein or less.

The Chroma Meter was calibrated to a white calibration plate (No. 19033177). The illuminant was set to D65 and the observer to 2 degree. The color (CIELAB color space, a*-, b*-, L*-value) was measured with lids covering the suspension, as the average of three individual readings in different places of the petri dish.

Demineralised water reference has the following values:
L* 39.97±0.3
a* 0.00±0.06
b*−0.22±0.09

The measurements were converted to delta/difference values based on demineralised water measurement.

$$\text{delta } L^* = L_{sample\ standardised\ to\ 6.0\ w/w\ \%\ protein}^* - L_{demin.\ water}^*, \text{ measured at room temperature.}$$

$$\text{delta } a^* = a_{sample\ standardised\ to\ 6.0\ w/w\ \%\ protein}^* - a_{demin.\ water}^*, \text{ measured at room temperature.}$$

$$\text{delta } b^* = b_{sample\ standardised\ to\ 6.0\ w/w\ \%\ protein}^* - b_{demin.\ water}^*, \text{ measured at room temperature.}$$

The samples is standardized to 6.0 w/w % protein or below.

The L*a*b* colour space (also referred to as the CIELAB space) is one of the uniform colour spaces defined by the International Commission on Illumination (CIE) in 1976 and was used to quantitatively report lightness and hue (ISO 11664-4:2008(E)/CIE S 014-4/E:2007).

In this space, L* indicates lightness (value from 0-100), the darkest black at L*=0, and the brightest white at L*=100.

The colour channels a* and b*, represent true neutral grey values at a*=0 and b*=0. The a* axis represents the green-red component, with green in the negative direction and red in the positive direction. The b* axis represents the blue-yellow component, with blue in the negative direction and yellow in the positive direction.

Example 1.10 Beverage Stability Test/Insoluble Protein Matter

Whey protein beverage compositions were considered stable if less than 15% of total protein in heated samples precipitated upon centrifugation at 3000 g for 5 minutes:
Approx. 20 g samples were added to centrifuge tubes and centrifugated at 3000 g 5 min.
Kjeldahl analysis of protein before centrifugation and the supernatant after centrifugation were used to quantify protein recovery See example 1.5
The loss of protein is calculated:

$$\text{Denaturation \%} = \left(\frac{P_{total} - P_{3000xg}}{P_{total}}\right) * 100\%$$

This parameter is also sometimes referred to as the level of insoluble protein matter and can be used for analyzing both liquid and powder samples. If the sample is a powder, 10 g of the powder is suspended in 90 g demineralized water and allowed to hydrate at 22 degrees C. under gentle stirring for 1 hours. Approx. 20 g of sample (e.g. liquid sample or the suspended powder sample) to centrifuge tubes and centrifugated at 3000 g 5 min. Kjeldahl analysis of protein before centrifugation ($P_{total}$) and the supernatant after centrifugation ($P_{3000xg}$) were used to quantify protein recovery according to Example 1.5.

The amount of insoluble protein matter is calculated:

$$\text{percentage of insoluble protein matter} = \left(\frac{P_{total} - P_{3000xg}}{P_{total}}\right) * 100\%$$

Example 1.11: Sensory Evaluation

The heat-treated beverage preparations underwent a descriptive sensory evaluation. The beverage preparations had been subjected to heat using plate heat exchangers.

1 volume sample was mixed with 1 volume water and compared to non-heated whey protein isolate, lactic acid and citric acid are also used to form an attribute list prior to the final tasting session:

| Category | Attributes |
| --- | --- |
| Aroma | Whey, acidic (sour milk product) |
| Basic taste | Acid, bitter |
| Flavour | Whey, citric acid, lactic acid |
| Mouth feeling | Drying, astringency |

Crackers, white tea, melon and water were used to cleanse the mouth of participants between each sample.

15 mL test sample at ambient temperature (20-25° C.) was served in small cups.

Test samples were each served to 10 individuals three times in three different blocks in randomised order.

The attributes (see table above) were rated on a 15 cm scale with 0=low intensity and 15=high intensity.

The statistical analysis was conducted in 'Panelcheck' software using a 3-way ANOVA test for multiple replicates. Samples were fixed and panel was set to random.

Bonferroni correction implying least significance difference values (pairwise comparisons of groups associated to a letter) was used to evaluate significant differences between samples.

Example 1.12: Determination of Transparency by Imaging

Photographs of beverage preparations were conducted by placing samples in turbidity NTU measuring vials touching a piece of paper with 'lorem ipsum' text. Vials were photographed using a smartphone and the inventors evaluated whether the text could be clearly observed through the vial.

Example 1.13: Determination of Ash Content

The ash content of a food product is determined according to NMKL 173:2005 "Ash, gravimetric determination in foods".

Example 1.14: Determination of Conductivity

The "conductivity" (sometimes referred to as the "specific conductance") of an aqueous solution is a measure of the ability of the solution to conduct electricity. The conductivity may e.g. be determined by measuring the AC resistance of the solution between two electrodes and the result is typically given in the unit milliSiemens per cm (mS/cm). The conductivity may for example be measured according to the EPA (the US Environmental Protection Agency) Method No. 120.1.

Conductivity values mentioned herein have been normalised to 25 degrees C. unless it is specified otherwise.

The conductivity is measured on a Conductivity meter (WTW Cond 3210 with a tetracon 325 electrode).

The system is calibrated as described in the manual before use. The electrode is rinsed thoroughly in the same type of medium as the measurement is conducted on, in order to avoid local dilutions. The electrode is lowered into the medium so that the area where the measurement occurs is completely submerged. The electrode is then agitated so that any air trapped on the electrode is removed. The electrode is then kept still until a stable value can be obtained and recorded from the display.

Example 1.15: Determination of the Total Solids of a Solution

The total solids of a solution may be determined according NMKL 110 $2^{nd}$ Edition, 2005 (Total solids (Water)—Gravimetric determination in milk and milk products). NMKL is an abbreviation for "Nordisk Metodikkomité for Næringsmidler".

The water content of the solution can be calculated as 100% minus the relative amount of total solids (% w/w).

Example 1.16: Determination of pH

All pH values are measured using a pH glass electrode and are normalised to 25 degrees C.

The pH glass electrode (having temperature compensation) is rinsed carefully before and calibrated before use.

When the sample is in liquid form, then pH is measured directly in the liquid solution at 25 degrees C.

When the sample is a powder, 10 gram of a powder is dissolved in 90 ml of demineralised water at room temperature while stirring vigorously. The pH of the solution is then measured at 25 degrees C.

Example 1.17: Determination of Loose Density and Bulk Density

The density of a dry powder is defined as the relation between weight and volume of the powder which is analysed using a special Stampf volumeter (i.e. a measuring cylinder) under specified conditions. The density is typically expressed in g/ml or kg/L.

In this method, a sample of dried powder is tamped in a measuring cylinder. After a specified number of tappings, the volume of the product is read and the density is calculated.

Three types of densities can be defined by this method:
Poured density, which is the mass divided with the volume of powder after it has been transferred to the specified measuring cylinder.
Loose density, which is the mass divided with the volume of powder after 100 tappings according to the specified conditions in this standard.
Bulk density, which is the mass divided with the volume of powder after 625 tappings according to the specified conditions in this standard.

The method uses a special measuring cylinder, 250 ml, graduated 0-250 ml, weight 190±15 g (J. Engelsmann A. G. 67059 Ludwigshafen/Rh) and a Stampf volumeter, e.g. J. Engelsmann A. G.

The loose density and the bulk density of the dried product are determined by the following procedure.

Pre-Treatment:

The sample to be measured is stored at room temperature.

The sample is then thoroughly mixed by repeatedly rotating and turning the container (avoid crushing particles). The container is not filled more than ⅔.

Procedure:

Weigh 100.0±0.1 gram of powder and transfer it to the measuring cylinder. The volume Vo is read in ml.

If 100 g powder does not fit into the cylinder, the amount should be reduced to 50 or 25 gram.

Fix the measuring cylinder to the Stampf volumeter and let it tap 100 taps. Level the surface with the spatula and read the volume $V_{100}$ in ml.

Change the number of tabs to 625 (incl. the 100 taps). After tapping, level the surface and read the volume $V_{625}$ in ml.

Calculation of Densities:

Calculate the loose and the bulk densities expressed in g/ml according to the following formula:

Bulk density=$M/V$ where M designates weighed sample in grams and V designates volume after 625 tappings in ml.

Example 1.18: Determination of the Water Content of a Powder

The water content of a food product is determined according to ISO 5537:2004 (Dried milk—Determination of moisture content (Reference method)). NMKL is an abbreviation for "Nordisk Metodikkomité for Næringsmidler".

Example 1.19: Determination of the Amounts of Calcium, Magnesium, Sodium, Potassium, Phosphorus (ICP-MS Method)

The total amounts of calcium, magnesium, sodium, potassium, and phosphorus are determined using a procedure in which the samples are first decomposed using microwave digestion, and then the total amount of mineral(s) is determined using an ICP apparatus.

Apparatus:

The microwave is from Anton Paar and the ICP is an Optima 2000DV from PerkinElmer Inc.

Materials:
1 M $HNO_3$
Yttrium in 2% $HNO_3$
Suitable standards for calcium, magnesium, sodium, potassium, and phosphorus in 5% $HNO_3$ Pre-Treatment:

Weigh out 0.2 gram of powder sample or 1 g of liquid samples and transfer the powder to a microwave digestion tube. Add 5 mL 1M $HNO_3$. Digest the samples in the microwave in accordance with microwave instructions. Place the digested tubes in a fume cupboard, remove the lid and let volatile fumes evaporate.

Measurement Procedure:

Transfer pre-treated sample to DigiTUBE using a known amount of Milli-Q water. Add a solution of yttrium in 2% $HNO_3$ to the digestion tube (about 0.25 mL per 50 mL diluted sample) and dilute to known volume using Milli-Q water. Analyse the samples on the ICP using the procedure described by the manufacturer.

A blind sample is prepared by diluting a mixture of 10 mL 1M $HNO_3$ and 0.5 mL solution of yttrium in 2% $HNO_3$ to a final volume of 100 mL using Milli-Q water.

At least 3 standard samples are prepared having concentrations which bracket the expected sample concentrations.

The detection limit for liquid samples is 0.005 g/100 g sample for Ca, Na, K and Phosphor and 0.0005 g/100 g sample for Mg. The detection limit for powder samples is 0.025 g/100 g sample for Ca, Na, K and Pho and 0.0005 g/100 g sample for Mg.

When at or below detection limits of Pho the value of the detection limit is used in examples to demonstrate the maximum amount of Pho present as a worst-case scenario.

Example 1.20: Determination of the Furosine-Value

The furosine value is determined as described in "Maillard Reaction Evaluation by Furosine Determination During Infant Cereal Processing", Guerra-Hernandez et al, Journal of Cereal Science 29 (1999) 171-176, and the total amount of protein is determined according to Example 1.5. The furosine value is reported in the unit mg furosine per 100 g protein.

Example 1.21: Determination of the Crystallinity of BLG in a Liquid

The following method is used to determine the crystallinity of BLG in a liquid having a pH in the range of 5-6.
a) Transfer a 10 mL sample of the liquid in question to a Maxi-Spin filter with a 0.45 micron pore size CA membrane.
b) Immediately spin the filter at 1500 g for 5 min. keeping the centrifuge at 2 degrees C.
c) Add 2 mL cold Milli-Q water (2 degrees C.) to the retentate side of the spin filter and immediately, spin the filter at 1500 g for 5 min while keeping the centrifuge cooled at 2 degrees C., collect the permeate (permeate A), measure the volume and determine BLG concentration via HPLC using the method outlined in Example 1.31.
d) Add 4 mL 2M NaCl to the retentate side of the filter, agitate quickly and allow the mixture to stand for 15 minutes at 25 degrees C.
e) Immediately spin the filter at 1500 g for 5 min and collect the permeate (permeate B)
f) Determine the total weight of BLG in permeate A and permeate B using the method outlined in Example 1.31 and convert the results to total weight of BLG instead of weight percent. The weight of BLG in permeate A is referred to as $m_{Permeate\ A}$ and the weight of BLG in permeate B is referred to as $m_{Permeate\ B}$.
g) The crystallinity of the liquid with respect to BLG is determined as:

$$crystallinity = m_{Permeate\ B} / (m_{Permeate\ A} + m_{Permeate\ B}) * 100\%$$

Example 1.22: Determination of the Crystallinity of BLG in a Dry Powder

This method is used to determine the crystallinity of BLG in a dry powder.
a) 5.0 gram of the powder sample is mixed with 20.0 gram of cold Milli-Q water (2 degrees C.) and allowed to stand for 5 minute at 2 degrees C.
b) Transfer the sample of the liquid in question to a Maxi-Spin filter with a 0.45 micron CA membrane.
c) Immediately spin the filter at 1500 g for 5 min. keeping the centrifuge at 2 degrees C.
d) Add 2 mL cold Milli-Q water (2 degrees C.) to the retentate side of the spin filter and immediately, spin the filter at 1500 g for 5 min, collect the permeate (permeate A), measure the volume and determine BLG concentration via HPLC using the method outlined in Example 1.31 and convert the results to total weight of BLG instead of weight percent. The weight of BLG in permeate A is referred to as $m_{permeate\ A}$
f) The crystallinity of BLG in the powder is then calculated using the following formula:

$$crystallinity = \frac{m_{BLG\ total} - m_{permeate\ A}}{m_{BLG\ total}} * 100\%$$

where $m_{BLG\ total}$ is the total amount of BLG in the powder sample of step a).

If the total amount of BLG of powder sample is unknown, this may be determined by suspending another 5 g powder sample (from the same powder source) in 20.0 gram of Milli-Q water, adjusting the pH to 7.0 by addition of aqueous NaOH, allowing the mixture to stand for 1 hour at 25 degrees C. under stirring, and finally determining the total amount of BLG of the powder sample using Example 1.31.

Example 1.23: Determination of UF Permeate Conductivity 15 mL of sample is transferred to an Amicon Ultra-15 Centrifugal Filter Units with a 3 kDa cut off (3000 NMWL) and centrifugated at 4000 g for 20-30 minutes or until a sufficient volume of UF permeate for measuring conductivity is accumulated in the bottom part of the filter units. The conductivity is measured immediately after centrifugation. The sample handling and centrifugation are performed at the temperature of the source of the sample.

Example 1.24: Detection of Dried BLG Crystals in a Powder

The presence of dried BLG crystals in a powder can be identified the following way:

A sample of the powder to be analysed is re-suspended and gently mixed in demineralised water having a temperature of 4 degrees C. in a weight ratio of 2 parts water to 1 part powder, and allowed to rehydrate for 1 hour at 4 degrees C.

The rehydrated sample is inspected by microscopy to identify presence of crystals, preferably using plan polarised light to detect birefringence.

Crystal-like matter is separated and subjected to x-ray crystallography in order verify the existence of crystal structure, and preferably also verifying that the crystal lattice (space group and unit cell dimensions) corresponds to those of a BLG crystal.

The chemical composition of the separated crystal-like matter is analysed to verify that its solids primarily consists of BLG.

Example 1.25: Determination of the Total Amount of Lactose

The total amount of lactose is determined according to ISO 5765-2:2002 (IDF 79-2: 2002) "Dried milk, dried ice-mixes and processed cheese—Determination of lactose content—Part 2: Enzymatic method utilizing the galactose moiety of the lactose".

Example 1.26: Determination of the Total Amount of Carbohydrate

The amount of carbohydrate is determined by use of Sigma Aldrich Total Carbohydrate Assay Kit (Cat MAK104-1KT) in which carbohydrates are hydrolysed and converted to furfural and hydroxyfurfurals which are converted to a chromagen that is monitored spectrophotometrically at 490 nm.

Example 1.27: Determination of the Total Amount of Lipids

The amount of lipid is determined according to ISO 1211:2010 (Determination of Fat Content—Rôse-Gottlieb Gravimetric Method).

Example 1.28: Determination of Brix

Brix measurements were conducted using a PAL-α digital hand-held refractometer (Atago) calibrated against polished water (water filtered by reverse osmosis to obtain a conductivity of at most 0.05 mS/cm).

Approx. 500 μl of sample was transferred to the prism surface of the instrument and the measurement was started. The measured value was read and recorded.

The Brix of a whey protein solution is proportional to the content of total solids (TS) and TS (% w/w) is approx. Brix*0.85.

Example 1.29 Determination of Lactoferrin and Lactoperoxidase

The concentration of lactoferrin is determined by an ELISA immunoassay as outlined by Soyeurt 2012 (Soyeurt et al; Mid-infrared prediction of lactoferrin content in bovine milk: potential indicator of mastitis; Animal (2012), 6:11, pp 1830-1838)

The concentration of lactoperoxidase is determined using a commercially available bovine lactoperoxidase kit.

Example 1.30: Determination the Number of Colony-Forming Units

The determination of the number of colony-forming units per gram sample is performed according to ISO 4833-1: 2013(E): Microbiology of food and animal feeding stuffs—horizontal method for the enumeration of microorganisms—Colony-count technique at 30° C.

Example 1.31: Determination of the Total Amount of BLG, ALA, and CMP

This procedure is a liquid chromatographic (HPLC) method for the quantitative analysis of proteins such as ALA, BLG and CMP and optionally also other protein species in a composition. Contrary to the method of Example 1.6 the present method also measures proteins that are present in aggregated and therefore provides a measure of the total amount of the protein species in the composition in question.

The mode of separation is Size Exclusion Chromatography (SEC) and the method uses 6M Guanidine HCl buffer as both sample solvent and HPLC mobile phase. Mercaptoethanol is used as a reducing agent to reduce the disulphide (S—S) in the proteins or protein aggregates to create unfolded monomeric structures.

The sample preparation is easily achieved by dissolving 10 mg protein equivalent in the mobile phase.

Two TSK-GEL G3000SWXL (7.7 mm×30.0 cm) columns (GPC columns) and a guard column are placed in series to achieve adequate separation of the major proteins in raw materials.

The eluted analytes are dectected and quantified by UV detection (280 nm).

Equipment/Materials:
1. HPLC Pump 515 with manual seal wash (Waters)
2. HPLC Pump Controller Module II (Waters)
3. Autosampler 717 (Waters)
4. Dual Absorbance Detector 2487 (Waters)
5. Computer software capable of generating quantitative reports (Empower 3, Waters)
6. Analytical column: Two TSK-GEL G3000SWXL (7.8× 300 mm, P/N: 08541). Guard Column: TSK-Guard Column SWxL (6.0×40 mm, P/N: 08543).
7. Ultrasonic Bath (Branson 5200)
8. 25 mm Syringe filter with 0.2 μm Cellulose Acetate membrane. (514-0060, VWR)

Procedure:

Mobile Phase

A. Stock Buffer Solution.
1. Weigh 56.6 g of $Na_2HPO_4$, 3.5 g of $NaH_2PO_4$, and 2.9 g of EDTA in to a 1000 mL beaker. Dissolve in 800 mL of water.
2. Measure pH and adjust to 7.5±0.1, if necessary, with HCl (decrease pH) or NaOH (increase pH).
3. Transfer to a 1000 mL volumetric flask and dilute to volume with water.

B. 6M Guanidine HCl Mobile Phase.
1. Weigh 1146 g of Guanidine HCl in to a 2000 mL beaker, and add 200 mL of the stock buffer solution (A)
2. Dilute this solution to about 1600 mL with water while mixing with a magnetic stir bar (50° C.)
3. Adjust the pH to 7.5±0.1 with NaOH.
4. Transfer into a 2000 mL volumetric flask and dilute to volume with water.
5. Filter using the solvent filtration apparatus with the 0.22 μm membranefilter.

Calibration Standards.

Calibration standards of each protein to be quantified are prepared the following way:
1. Weigh accurately (to 0.01 mg) about 25 mg of the protein reference standard into a 10 mL volumetric flask and dissolve in 10 mL of water.
   This is the protein stock standard solution (S1) of the protein
2. Pipette 200 μl of S1 into a 20 ml volumetric flask and dilute to volume with mobile phase.
   This is the low working standard solution WS1.
3. Pipette 500 μL of S1 into a 10 mL volumetric flask and dilute to volume with mobile phase.
   This is standard solution WS2.
4. Pipette 500 μL of S1 into a 5 mL volumetric flask and dilute to volume with mobile phase.
   This is standard solution WS3.
5. Pipette 750 μL of S1 into a 5 mL volumetric flask and dilute to volume with mobile phase.
   This is standard solution WS4.
6. Pipette 1.0 mL of S1 into a 5 mL volumetric flask and dilute to volume with mobile phase.
   This is the high working standard solution WS5.
7. Using graduated disposable pipettes transfer 1.5 mL of WS1-5 into separate vials.

Add 10 µL of 2-mercaptoethanol to each vial and cap. Vortex the solutions for 10 sec.

Let the standards stay at ambient temperature for about 1 hr.

8. Filter the standards using 0.22 µm Cellulose Acetate syringe filters.

The purity of protein is measured using Kjeldahl (N×6.38) and the area % from standard solution WS5 using the HPLC.

protein (mg)="protein standard weight" (mg)×P1×P2

P1=P % (Kjeldahl)
P2=protein area % (HPLC)

Sample Preparation
1. Weigh the equivalent of 25 mg of protein of the original sample into a 25 mL volumetric flask.
2. Add approximately 20 mL of mobile phase and let the sample dissolve for about 30 min.
3. Add mobile phase to volume and add 167 µL of 2-mercaptoethanol to the 25 ml sample solution.
4. Sonicate for about 30 min and afterwards let the sample stay at ambient temperature for about 1½ hours.
5. Mix the solution and filter using 0.22 µl Cellulose Acetate syringe filters.

HPLC System/Columns
Column Equilibration
1. Connect the GPC guard column and the two GPC analytical columns in series. New columns are generally shipped in a phosphate-salt buffer.
2. Run water through a new column gradually from 0.1 to 0.5 mL/min in 30 to 60 mins. Continue flushing for about 1 hour.
3. Gradually decrease flow rate from 0.5 mL/min to 0.1 mL/min and replace with mobile phase in the reservoir.
4. Increase pump flow rate gradually from 0.1 to 0.5 mL/min in 30 to 60 mins to avoid pressure shock and leave at 0.5 mL/min.
5. Inject ten samples to allow the column to be saturated and wait for the peaks to elute.
This will aid in the conditioning of the column.
This step is done without the need of waiting for each injection to be complete before injecting the next.
6. Equilibrate with the mobile phase at least 1 hour.

Calculation of the Results

Quantitative determination of the contents of the proteins to be quantified, e.g. alpha-lactalbumin, beta-lactoglobulin, and caseinomacropeptide, is performed by comparing the peak areas obtained for the corresponding standard proteins with those of the samples. The results are reported as g specific protein/100 g of the original sample or weight percentage of the specific protein relative to the weight of the original sample.

Example 2: Production of a Spray-Dried, Acidic BLG Isolate Powder

Whey Protein Feed

Lactose-depleted UF retentate derived from sweet whey from a standard cheese production process was filtered through a 1.2 micron filter and had been fat-reduced via a Synder FR membrane prior to being used as feed for the BLG crystallisation process. The chemical composition of the feed can be seen in Table A. We note that all weight percentages of specific proteins, such as BLG, ALA, mentioned in this Example pertain to the weight percentage of the non-aggregated proteins relative to total protein.

Conditioning

The sweet whey feed was conditioned on an ultrafiltration setup at 20 degrees C., using a Koch HFK-328 type membrane (70 m$^2$ membrane) with a 46 mill spacer feed pressure 1.5-3.0 bar, to a feed concentration of 21% total solids (TS)+5, and using as diafiltration medium polished water (water filtered by reverse osmosis to obtain a conductivity of at most 0.05 mS/cm). The pH was then adjusted by adding HCl so that the pH was approx. 5.5. Diafiltration continued until the drop in conductivity of the retentate was below 0.1 mS/cm over a 20 min period. The retentate was then concentrated until the permeate flow was below 1.43 L/h/m$^2$. A first sample of concentrated retentate was taken and subjected to centrifugation at 3000 g for 5 minutes. The supernatant of the first sample was used for the determination of BLG yield.

Crystallisation

The concentrated retentate was transferred to a 300 L crystallisation tank where it was seeded with pure BLG crystal material made from rehydrated, spray-dried BLG crystals. Subsequently, the seeded whey protein solution was cooled from 20 degrees C. to approx. 6 degrees C. over approx. 10 hours to allow the BLG crystals to form and grow.

After cooling, a sample of the crystal-containing whey protein solution (the second sample) was taken and the BLG crystals were separated by centrifugation at 3000 g for 5 minutes. The supernatant and crystal pellets from the second sample were subjected to HPLC analysis as described below. The yield of crystallisation was calculated as outlined below and determined to 57%.

TABLE A

| Chemical composition of the feed Feed standardized to 95% total solids | |
| --- | --- |
| Protein composition % w/w of total protein | |
| ALA | 10.2 |
| BLG | 59.6 |
| Other proteins | 30.2 |
| Selected other components % w/w | |
| Ca | 0.438 |
| K | 0.537 |
| Mg | 0.077 |
| Na | 0.131 |
| Pho | 0.200 |
| Fat | 0.220 |
| protein concentration | 87 |

BLG Yield Determination Using HPLC:

The supernatants of the first and second samples were subjected to the same degree of dilution by adding polished water and the diluted supernatants were filtered through a 0.22 µm filter. For each filtered and diluted supernatant the same volume was loaded on an HPLC system with a Phenomenex Jupiter® 5 µm C4 300 Å, LC Column 250×4.6 mm, Ea. and detected at 214 nm.

The samples were run using the following conditions:
Buffer A: MilliQ water, 0.1% w/w TFA
Buffer B: HPLC grade acetonitrile, 0.085% w/w TFA
Flow: 1 mL/min
Column temperature: 40 degrees C.
Gradient: 0-30 minutes 82-55% A and 18-45% B; 30-32 minutes 55-10% A and 45-90% B; 32.5-37.5 minutes 10% A and 90% B; 38-48 minutes 10-82% A and 90-18% B.

Data Treatment:

As both supernatants were treated in the same way, one can directly compare the area of the BLG peaks to calculate a relative yield. As the crystals only contain BLG and the samples all have been treated in the same way, the concentration of alpha-lactalbumin (ALA) and hence the area of ALA should be the same in all of the samples. Therefore, the area of ALA before and after crystallisation is used as a correction factor (cf) when calculating the relative yield.

$$cf_\alpha = \frac{\text{area of } ALA_{before\ crystallization}}{\text{area of } ALA_{after\ crystallization}}$$

The relative yield is calculated by the following equation:

$$Yield_{BLG} = \left(1 - \frac{cf_\alpha \times \text{area of } BLG_{after\ crystallization}}{\text{area of } BLG_{before\ crystallization}}\right) \times 100$$

Acid Dissolution of BLC Crystals

The remainder of the material from the crystallisation tank was separated using a decanter at 350 g, 2750 RPM, 150 RPM Diff. with a 64 spacer and a feed flow of 75 L/h before separation the feed was mixed 1:2 with polished water. The BLG crystal/solid phase from the decanter was then mixed with polished water in order to make it into a thinner slurry before a phosphoric acid or HCl was added to lower the pH to approx. 3.0 in order to quickly dissolve the crystals.

After dissolving the BLG crystals, the pure BLG protein liquid was concentrated to 15 Brix on the same UF setup as used to prepare the feed for crystallisation and the pH was adjusted to final pH of approx. 3.8. The liquid BLG isolate was then heated to 75 degrees for 5 minutes and subsequently cooled to 10 degrees C. The heat-treatment was found to reduce the microbial load from 137.000 CFU/g prior to the heat-treatment to <1000 CFU/g after the heat-treatment. The heat-treatment did not cause any protein denaturation and the intrinsic tryptophan fluorescence ratio (I330 nm/I350 nm) was determined to 1.20 indicating native confirmation of the BLG molecules.

The BLG was dried on a pilot plant spray drier with an inlet temperature of 180 degrees C. and an exit temperature of 75 degrees C. The resulting powder sampled at the exit had a water content of approx. 4% w/w, the chemical composition of the powder is shown in Table B. A sample of the dried powder was dissolved and the degree of protein denaturation was determined to 1.5% and the intrinsic tryptophan fluorescence emission ratio (I330/I350) was measured to 1.20.

TABLE B

The composition of the BLG isolate powder (BDL = below the detection limit) BLG isolate powder standardized to 95% total solids

| Protein composition % w/w of total protein | |
|---|---|
| ALA | 0.4 |
| BLG | 98.2 |
| Other protein | 1.4 |

TABLE B-continued

The composition of the BLG isolate powder (BDL = below the detection limit) BLG isolate powder standardized to 95% total solids

| Other selected components (% w/w) | |
|---|---|
| Ca | BDL |
| K | BDL |
| Mg | BDL |
| Na | BDL |
| Pho | 0.781 |
| fat | 0.09 |
| protein concentration | 90 |

The bulk density (625 taps) of the spray-dried powder was estimated at 0.2-0.3 g/cm$^3$.

Example 3: Preparation of Generic Whey Protein Beverage

Dried BLG isolate protein powders containing≥85% BLG on protein basis are dispersed in up to about 95% of the demineralized water required to reach the desired final protein concentration. Acidic BLG isolate powders is produced as outlined in example 2 while pH 5.5 BLG isolate powder are produced as outlined in example 7 of PCT/EP2017/084553.

As described in PCT/EP2017/084553, dissolution of BLG material may be aided by addition of acid (selected among one or more food-grade acid such as phosphoric acid, hydrochloric acid, citric acid, malic acid or salts in their dissolved or powder forms. If pH is reduced during dissolution by acid addition, the pH should preferably not pass desired target pH (i.e. avoid unnecessary titration with acid and/or base).

Optionally, minerals, sweeteners, flavours, stabilizers, emulsifiers or other components can be added also including sources of fats and carbohydrates. The employed process comprises the following steps:

In case fat is included then first heat oil to 70° C. in water bath, mix with emulsifier (typically to 0.2 w/w % in final recipe); for example the emulsifier Grindsted Citrem LR10 which is a citric acid ester, recommended for phosphate-free applications. Allow to cool to 60° C. (to avoid/reduce potential denaturation/aggregation when mixed with protein)

Mix slowly with preheated water (60° C.)

Add all powdered ingredients in premixed form (to avoid 'fisheyes'); this includes premixing of carbohydrates and protein, Optionally add minerals (NaCl, KCl, CaCl2 and MgCl2) to achieve concentrations of Na, K, Ca and Mg that comply with Foods for Special Medical Purposes (FSMP) requirements (target is middle of allowed range). Minerals were dissolved in demineralized water and added to reach desired concentrations of Na, K, Ca and Mg. Other food grade minerals that enable compliance with FMSP may further be used and added in dissolved or powder forms.

Adjust pH if necessary to final the pH using up to 10% phosphoric acid (or other food grade acid) or up to 10% NaOH.

Remaining water is added to reach desired protein concentration and the composition is optionally homogenized ('upstream homogenization')

subject the composition to heat-treatment

Optionally homogenize ('downstream homogenization').

For comparison, whey protein isolate replace the ≥85% BLG product in the making of reference samples while preserving remaining steps.

Samples were stored at 20° C. in a dark environment.

Example 4: Thermal Treatment of Whey Protein Compositions

Thermal treatment of the beverages was conducted using plate heat exchanger (Manufacturer: OMVE HTST/UHT pilot plant HT320-20) by heating at 120° C. for 20 seconds (High temperature, short time (HTST), results in denaturation of BLG) or 75° C. with 15 seconds to 5 minute holding times (BLG remain native) equipped with a 10 μm bonded Microfibre filter element, Code 12-57-60k (Headline filters). Other heat treatment conditions may also be applied.

Heat-treated beverage composition was tapped at 75-85° C. into 100 mL sterile bottles, then immediately sealed and placed on ice.

In other experiments, the thermal treatment was conducted by transfer of the whey protein source to thin-walled glass vials containing 15-30 mL sample. Vials immersed for 1 to 5 minutes in water baths pre-equilibrated at the target temperature ranging from 75° C. to 95° C. and followed by cooling on ice.

Example 5: Production of Heat-Treated Beverage Preparation

In the present example BLG beverages and WPI beverages comprising 6% protein and having a pH of 3.7 were prepared.

The BLG beverages were prepared by dissolving a pH 5.5 BLG isolate Powder (as described in example 7 of PCT/EP2017/084553) in demineralized water at 10 degrees C. 10% $H_3PO_4$ was slowly added to the solution. The final pH was adjusted to pH 3.7.

The solutions were heat-treated at 120° C. for 20 seconds using a plate heat exchanger or heat-treated at 75° C. with 15 seconds to 5 minute holding times as described in example 4. The beverages were tapped to provide a heat sterilized whey protein beverage composition. WPI beverages were prepared using the same procedure but from a WPI powder.

Below in table 1 is given the composition of the BLG powder used for the preparation of the beverage preparation, for comparison the composition of the WPI is also listed.

TABLE 1

Composition of BLG powder
(pH 5.5 powder) and WPI powder

| Description | Dry B-LG (w/w %) | WPI-B (w/w %) |
|---|---|---|
| ALA (w/w %) | 0.4 | 8 |
| BLG (w/w %) | 95.9 | 57 |
| Ash | 0.76 | 3 |
| Ca | 0.186 | 0.458 |
| Cl | BDL | BDL |
| Lipid | <0.04 | 0.1 |
| K | 0.0635 | 0.449 |

TABLE 1-continued

Composition of BLG powder
(pH 5.5 powder) and WPI powder

| Description | Dry B-LG (w/w %) | WPI-B (w/w %) |
|---|---|---|
| Mg | 0.02885 | 0.0818 |
| Na | BDL | 0.324 |
| $NO_3$ (ppm) | 1.0 | 3.5 |
| $NO_2$ (ppm) | 0.07 | n.d. |
| NPN | 0.09 | n.d. |
| Phosphorous | BDL | 0.215 |
| Protein | 94.57 | 90.45 |

Beverage preparations comprising BLG and WPI having a pH of 3.7 and a protein content of 6% w/w were heat-treated at 120° C. for 20 seconds and 75° C. for 15 seconds, wherein 95.9 w/w % of the proteins was BLG. In the WPI beverage (WPI-B) 57 w/w % of the proteins was BLG. The turbidity (example 1.7), the viscosity (example 1.8) and colour (example 1.9) of the different samples were analysed.

The results are presented in table 2 below and in FIG. 1.

TABLE 2

| | 120° C./20 s BLG pH 3.7 | 120° C./20 s WPI-B pH 3.7 | 75° C./15 s WPI-B pH 3.7 | 75° C./15 s BLG pH 3.7 |
|---|---|---|---|---|
| Turbidity (NTU) | 7.0 | 263 | 400 | 1.5 |
| Viscosity (cP) | 2.15 | 10.5 | 1.8 | 1.3 |

Conclusion

The turbidity of the BLG samples remained low at 75° C. while the WPI samples had a high turbidity. The WPI samples were also opaque see FIG. 1.

The sterilized BLG samples had a turbidity of 7.0 NTU compared to WPI which had a turbidity of 263 NTU.

The viscosity also remained low.

It is thus possible to produce transparent beverages having a BLG content of about 96 w/w % of the protein content at pH 3.7, while this is not possible in the WPI samples which became opaque under the same conditions.

Example 6a: Demonstrating that the Accessible pH Range for Clear Whey Protein Beverages can be Extended BLG samples were prepared wherein about 92 w/w % of the 6 w/w % protein was BLG and for comparison two different WPI samples were prepared comprising respectively about 60 w/w % (WPI-A) and 57 w/w % (WPI-B) of BLG.

The 6 w/w % whey protein compositions were prepared as described in example 3 (BLG isolate powders are produced according to example 2) adjusting the final pH using 10% phosphoric acid to obtain selected pH values between 3.0 and 3.9, respectively. In one aspect of the experiment, samples adjusted to pH levels between 3.0 and 3.9 were UHT treated at 120° C. for 20 seconds, tapped, sealed and cooled. In another aspect of the experiment, pH 3.0 and 3.9 samples were pasteurized at 75° C. for 15 seconds as described in example 4.

The turbidity (example 1.7), the viscosity (example 1.8), the colour (example 1.9) and the visual appearance (example 1.12) of the different samples were analyzed.

The results are presented in FIGS. 2-10.

Figure 2:
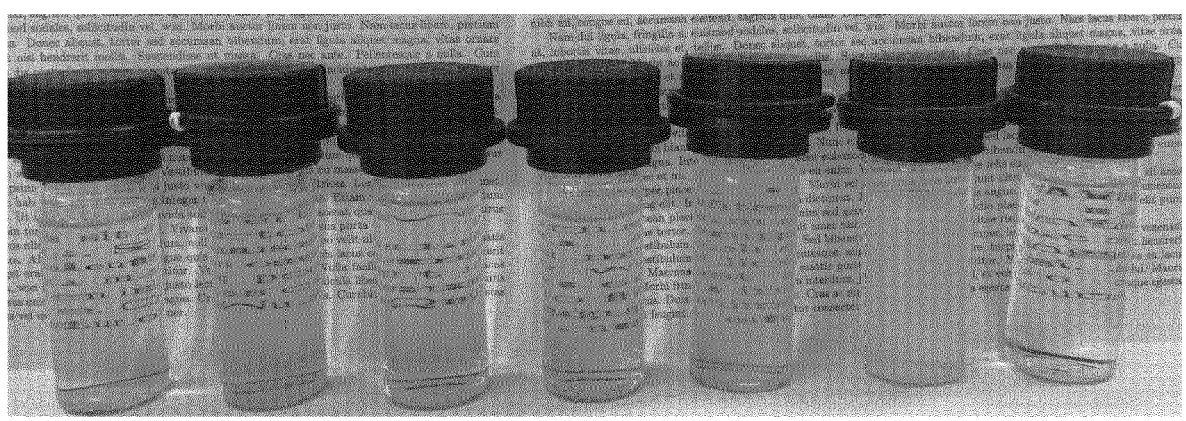
FIG. 2 shows images of WPI-B pH 3.0-3.7 120° C. and BLG pH 3.7 120° C./20 s.
Figure 3:
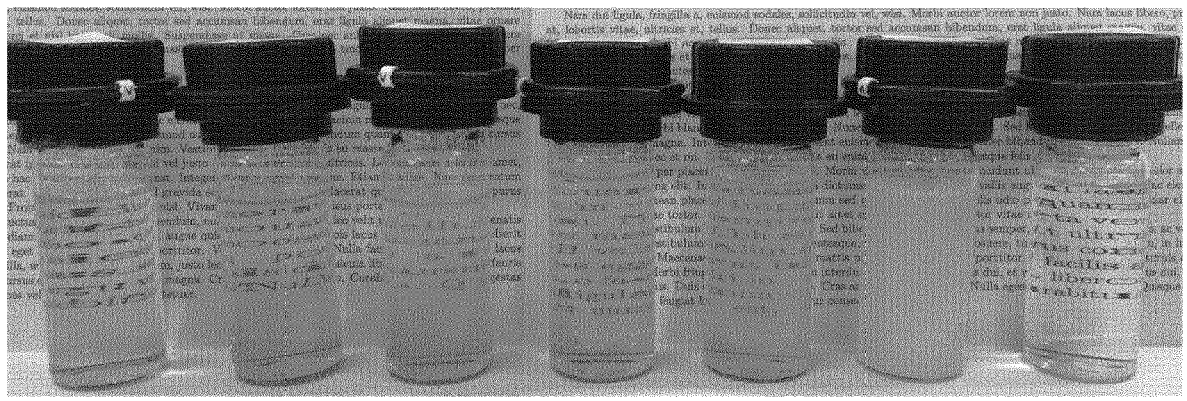
FIG. 3 shows images of WPI-B pH 3.0-3.7 75° C. and BLG pH 3.7 at 75° C./15 seconds.
Figure 4:
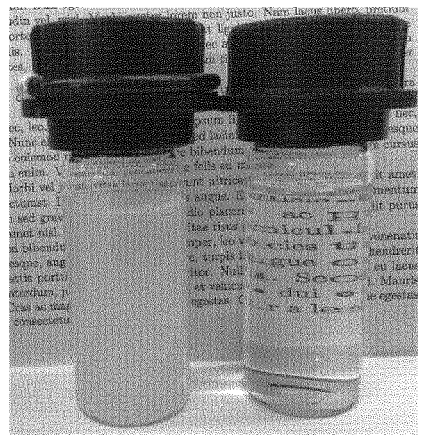
FIG. 4 shows images of WPI-B pH 3.7 and BLG pH 3.9, 75° C./15 seconds.

Results:

FIG. 2 shows images of WPI-B at pH 3.0-3.7 heat-treated at 120° C. for 20 seconds and BLG beverages at pH 3.7 heat-treated at 120° C. for 20 seconds. FIG. 3 shows images of WPI-B at pH 3.0-3.7, heat-treated at 75° C. and BLG at pH 3.7 at heat-treated at 75° C./15 seconds. FIG. 4 shows images of WPI-B at pH 3.7 and BLG beverages at pH 3.9, heated at 75° C. for 15 seconds.

Figure 5:
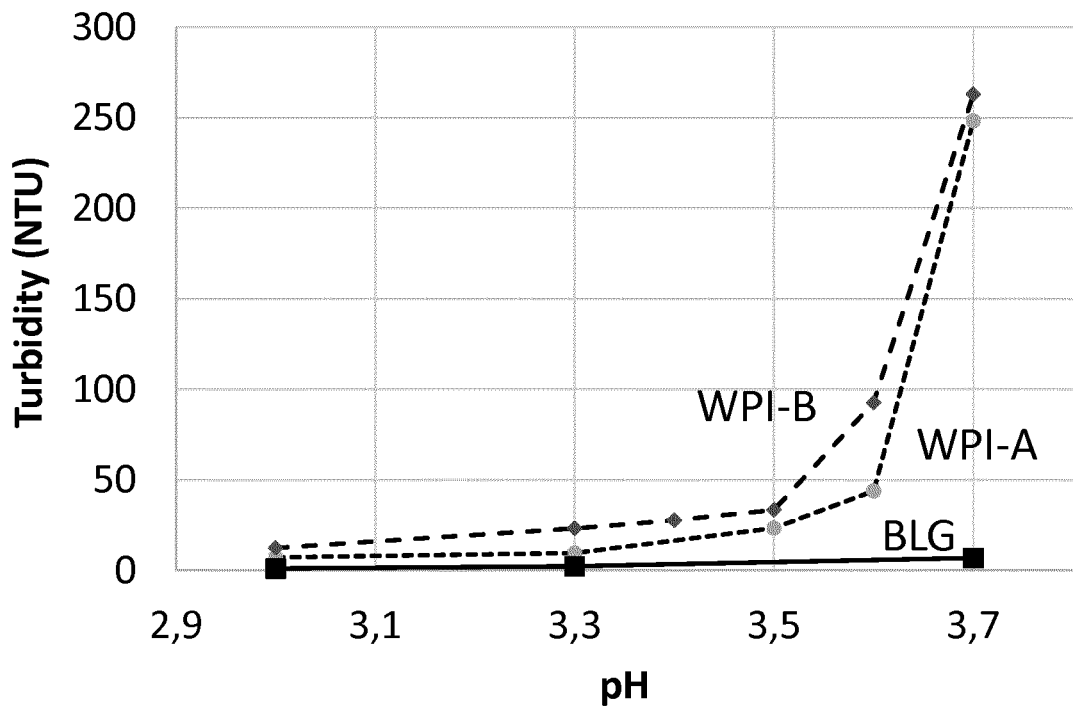
FIG. 5 illustrates the turbidity of a 6% UHT treated (120° C./20 s) BLG beverage preparation.
Figure 6:
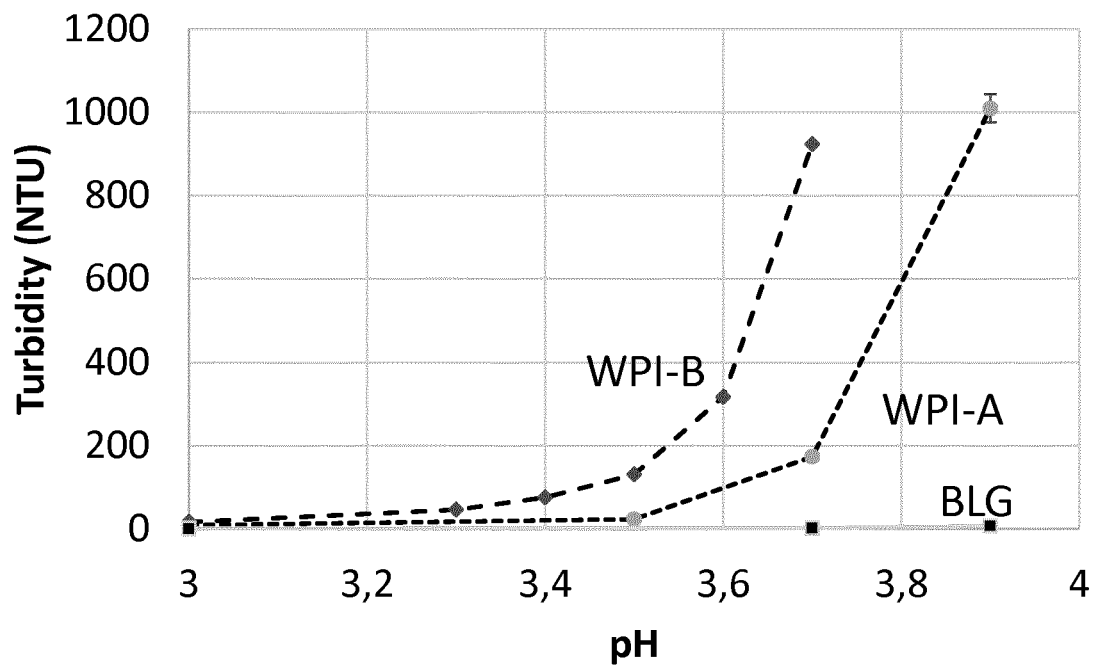
FIG. 6 illustrates the turbidity of a 6% pasteurized (75° C./15 s) BLG beverage composition.

Surprisingly the inventors found that the BLG beverage preparations remain visually clear even at pH 3.7 when it is either UHT sterilized (FIG. 2) and may even exceed pH 3.7 (pH 3.9-4.1) when pasteurized (FIG. 3 and FIG. 4) under which circumstances WPI is opaque. These findings are further supported by turbidity measurements as shown in FIG. 5 (UHT) and FIG. 6 (pasteurization) that remained below 40 NTU even at pH 3.7 and 3.9 where WPI greatly exceed 40 NTU, respectively.

Figure 7:
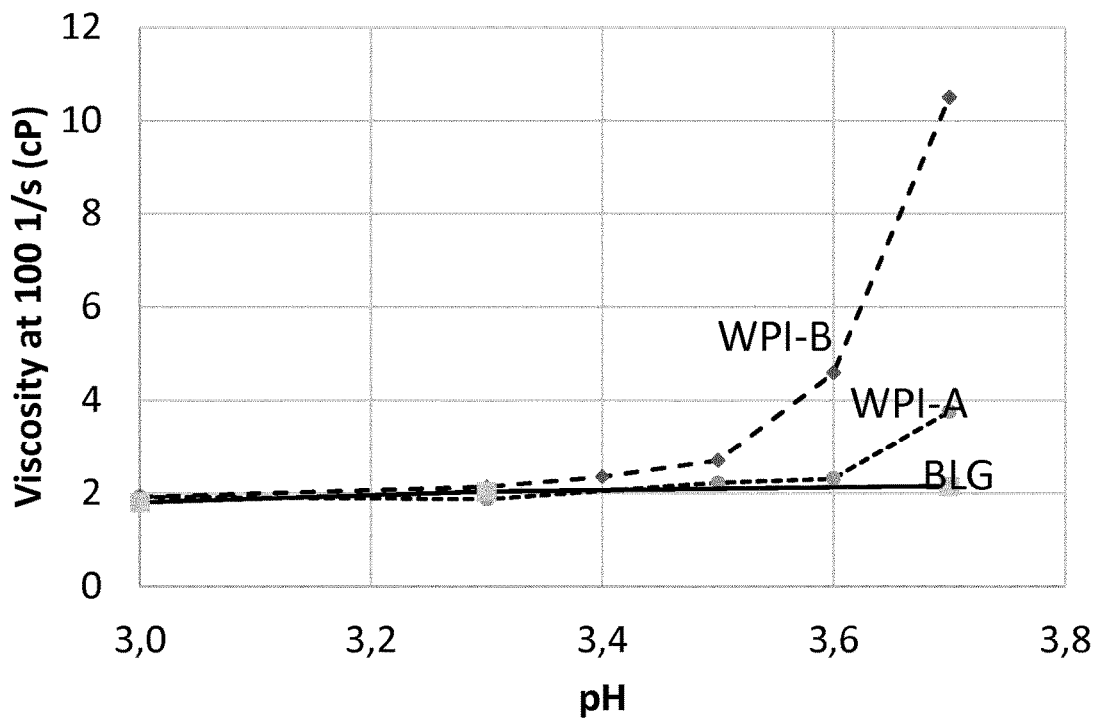
FIG. 7 illustrates the viscosity of a 6% UHT treated (120° C./20 s) BLG beverage preparation.

Viscosity remains low upon UHT treatment of BLG beverage preparations. The low viscosities demonstrate that the beverage samples were easily drinkable. The viscosity increases dramatically using WPI especially at high pH values (FIG. 7).

Figure 8:
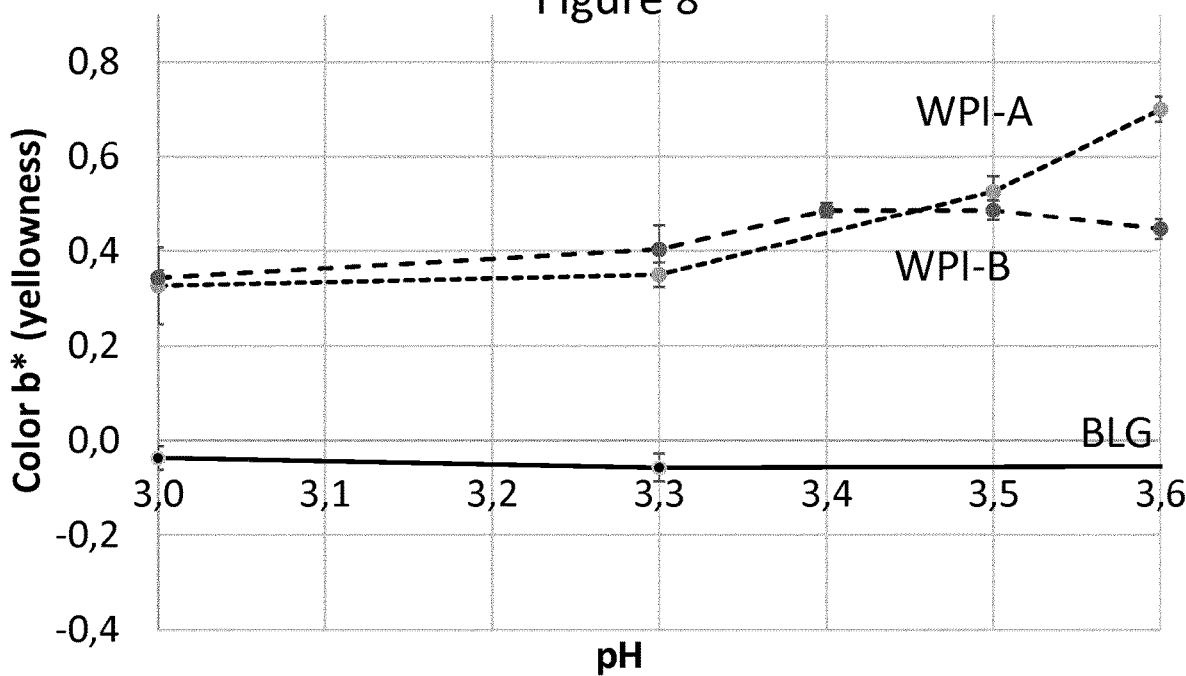
FIG. 8 illustrates the yellowness (b*) of a 6% UHT treated (120° C./20 s) beverage compositions
Figure 9:
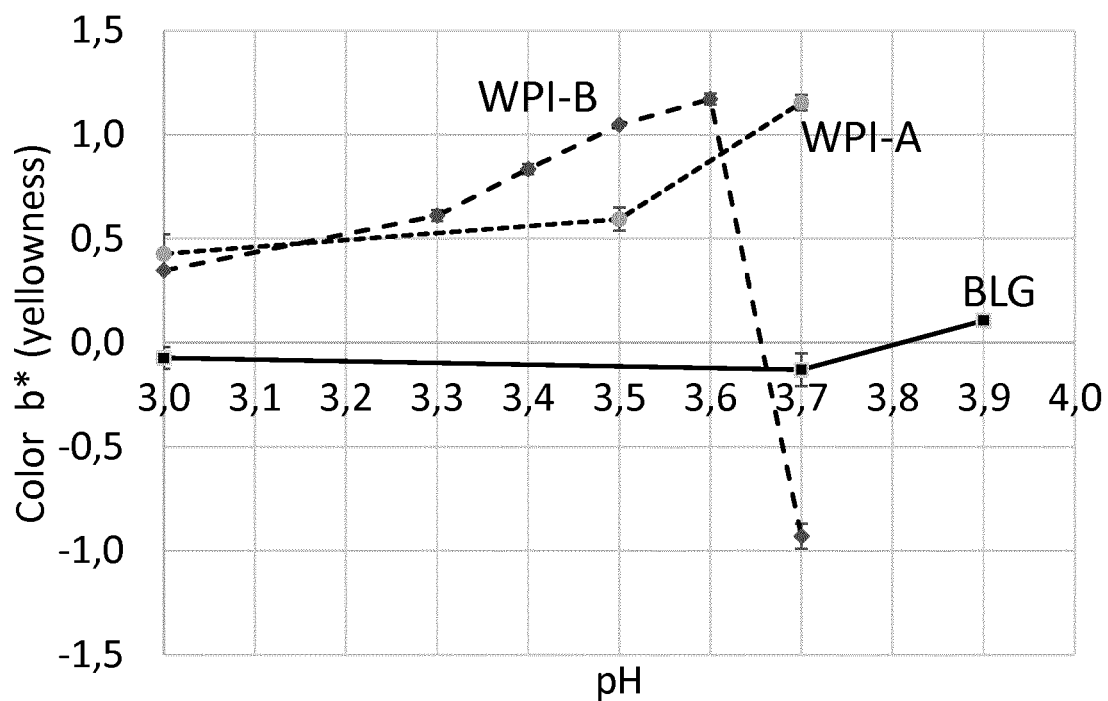
FIG. 9 illustrates the yellowness (b*) of a 6% pasteurized (75° C./15 s) beverage compositions

The inventors further found that the yellowness (b*-value) of heat-treated WPI beverages comprising a low amount of BLG (both UHT and pasteurization) greatly exceeded BLG up to at least pH 3.7, see FIGS. 8 (UHT) and 9 (pasteurized).

Conclusion

Use of whey protein beverages wherein at least 85% w/w of the protein is BLG enables at least two significant opportunities to provide whey protein beverages with desired attributes to consumers:
1. Increase pH during thermal treatment providing improvements in visual perception (colour, turbidity), and viscosity when compared to WPI.
2. Allow pasteurization to preserve advantages in 1) while extending accessible pH range even further.

Example 6b: Demonstrating that the Accessible pH Range for Clear Whey Protein Beverages can be Extended In the present example BLG beverages comprising 6 wt % and 12 wt % proteins and having a pH of 2.7, 3.0, 3.3 and 3.7 were prepared as described in Example 3. The BLG powder used for the preparation of the beverages is presented in table 3, the powder comprises 98.2 w/w % of the protein as BLG. The amount of Na, K, Ca and Mg is below the detection level.

TABLE 3

The composition of the BLG isolate powder (BDL = below the detection limit)

| Protein contribution: | % |
| --- | --- |
| Protein/dry matter | 96.9 |
| w/w % bLG of protein | 98.2% |
| w/w % aLA of protein | Not detected |
| w/w % cGMP of protein | Not detected |
| Sodium (Na) | BDL |

TABLE 3-continued

The composition of the BLG isolate powder (BDL = below the detection limit)

| Protein contribution: | % |
| --- | --- |
| Potassium (K) | BDL |
| Calcium (Ca) | BDL |
| Magnesium (Mg) | BDL |
| Phosphor (P) | BDL |
| pH of unadjusted 6% solution | 3.79 |

The final pH of the beverages was adjusted to pH 2.7, 3.0, 3.3 and 3.7 using 1M phosphoric acid. The beverages were heat treated to 75° C. or 95° C. for 5 min using a water bath as outlined in example 4.

The turbidity (example 1.7) and the nativeness of the proteins determined as intrinsic tryptophan fluorescence emission ratio R=I330/I350 (example 1.1) of the different samples were analyzed.

The results are presented in table 4.

TABLE 4

Analysis data of high protein beverages (6 and 12 w/w %) prepared from BLG at pH 2.7 to 3.7 with heating at 75° C. and 95° C. for 5 min.

| Protein weight-% | pH | Temperature ° C. (5 min.) | Turbidity NTU | Fluorescence Trp ratio I330/350 |
| --- | --- | --- | --- | --- |
| 6% | 2.7 | 75 | 0.8 | 1.18 |
|  | 3.0 |  | 0.9 | 1.18 |
|  | 3.3 |  | 0.9 | 1.17 |
|  | 3.7 |  | 2.0 | 1.17 |
| 12% | 2.7 |  | 1.2 | 1.17 |
|  | 3.0 |  | 1.3 | 1.17 |
|  | 3.3 |  | 1.7 | 1.18 |
|  | 3.7 |  | 3.3 | 1.17 |
| 6% | 2.7 | 95 | 1.0 | 1.14 |
|  | 3.0 |  | 0.9 | 1.13 |
|  | 3.3 |  | 1.3 | 1.13 |
|  | 3.7 |  | 3.8 | 1.10 |
| 12% | 2.7 |  | 6.49 | 1.12 |
|  | 3.0 |  | 11.5 | 1.11 |
|  | 3.3 |  | 15.9 | 1.09 |
|  | 3.7 |  | 8.4 | 1.02 |

Results:

The results clearly demonstrate that it was possible to produce clear BLG beverages having a turbidity below 16 NTU, comprising either 6 w/w % or 12 w/w % protein. The beverages were heat-treated at 75° C. for 5 min or 95° C. for 5 min. The beverages showed no aggregation or sedimentation by visual inspection. Compared to this the WPI samples of example 6a, see FIG. 4, shows that a WPI sample (6 w/w % protein) at pH 3.7 is turbid after a heat treatment of 75° C. for 15 seconds.

In addition it was also surprisingly found that beverages comprising 6 w/w % or 12 w/w % protein in the pH range of 2.7 to 3.7 heat-treated at 75° c. for 5 minutes all had a predominant native conformation, as demonstrated by surprisingly high Trp flu ratios of 1.17-1.18.

Example 6c: Colour Stability of the Beverages after 6 Months Storage at 20° C.

In the present example BLG beverages comprising 6 wt % proteins and having a pH of 3.0 and 3.7 were prepared as described in Example 3. The BLG powder used for the preparation of the beverages is described in table 3.

The final pH of the beverages was adjusted to pH of 3.0 and 3.7 using 10% phosphoric acid. The beverages were heat-treated at 75° C. for 15 seconds using a plate heat exchanger or UHT treated at 120° C. for 20 seconds as outlined in example 4.

After the heat-treatment the beverages were stored in the dark for 6 months at 20° C.

The colour (example 1.9) of the different samples were analyzed at day zero and after 6 weeks, 3 and 6 months.

Figure 25:
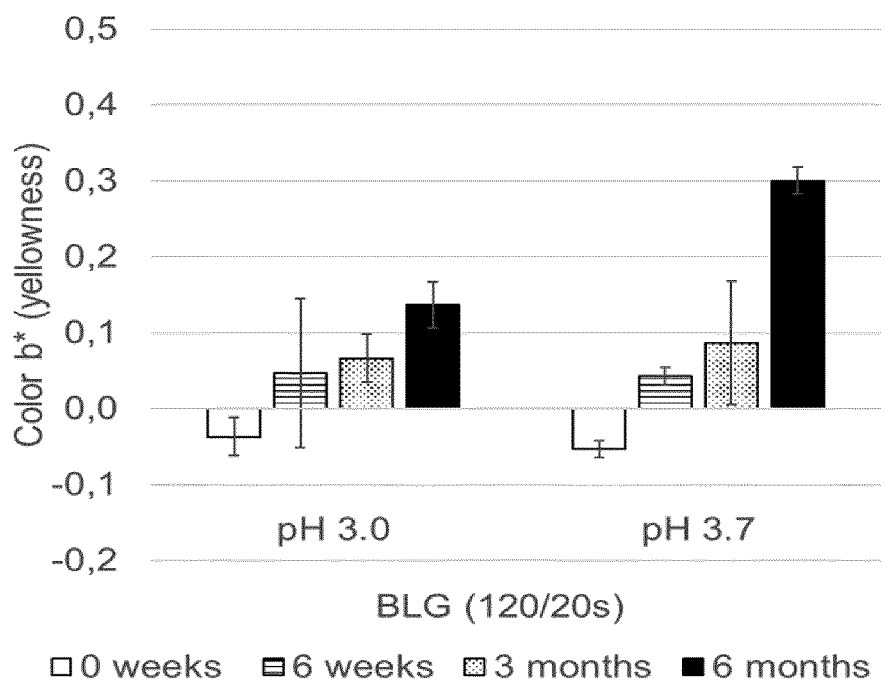
FIG. 25 illustrates the yellowness (b*) of a 6 w/w % BLG UHT treated (120° C./20 s) beverage compositions (pH 3.0 and 3.7), stored in the dark (20° C.) for up to 6 months.
Figure 26:
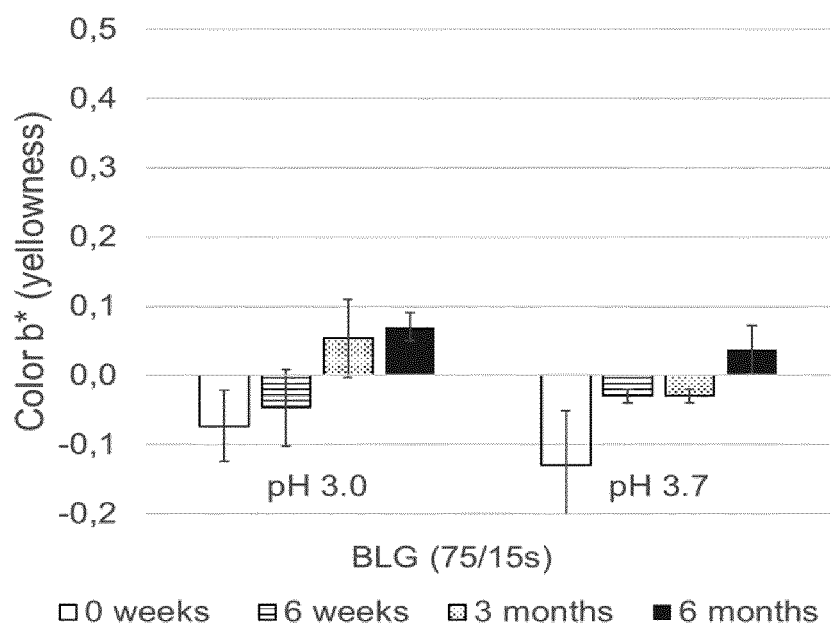
FIG. 26 illustrates the yellowness (b*) of 6 w/w % BLG pasteurized (75° C./15 s) beverages (pH 3.0 and 3.7), stored in the dark (20° C.) for up to 6 months.

The results are presented in FIGS. 25 and 26.

The solutions were thermally treated at 75-120° C. for a duration of time between 15 seconds to 5 minutes according to example 4 and as described in Table 5 and immediately cooled on ice.

The viscosity (example 1.8), the nativeness of the proteins determined as intrinsic tryptophan fluorescence emission ratio R=I330/I350 (example 1.1), the visual appearance (example 1.12) and the turbidity (example 1.7) of the different samples were analysed.

TABLE 5

Analysis data of high protein beverages prepared from BLG at pH 3.7 with heating at 75° C., 90° C. and 120° C..

| Protein weight-% | Temperature | Heating time in seconds | Viscosity cP | Fluorescence Trp ratio I330/I350 | Visual appearance | Turbidity NTU |
|---|---|---|---|---|---|---|
| 6 | — | — | 1.31 | 1.16 | Transparent | 0.9 |
| 6 | 120° C. | 20 | 2.15 | 1.08 | Transparent | 6.9 |
| 6 | 75° | 15 | 1.30 | 1.17 | Transparent | 1.0 |
| 10 | 75° | 300 | n.d. (liquid) | 1.17 | Transparent | — |
| 10 | 90° C. | 300 | n.d. (liquid) | 1.00 | Transparent | — |
| 12 | 75 | 300 | n.d. (liquid) | 1.17 | Transparent | 3.3 |
| 12 | 95 | 300 | n.d. (liquid) | 1.02 | Transparent | 8.4 |
| 15 | 75° | 15 | 2.91 | 1.19 | Transparent | 2.6 |
| 20 | 75° | 300 | 3.6 ± 0.03 | 1.16 | Transparent | — |
| 25 | 75° | 300 | 6.6 ± 0.1 | 1.16 | Transparent | 9.7 |
| 27.5 | 75° | 300 | 10.5 ± 0.1 | 1.16 | Transparent | |
| 32 | 75° | 300 | 16.1 ± 0.2 | 1.16 | Opaque | — |

Results:

The results demonstrate that the colour development in BLG beverages during storage was found to be slower in samples subjected to pasteurization (75° C./15 s) compared to UHT treated (120° C./20 s) BLG beverages. It was surprisingly found that the colour (yellowness) after 6 month storage in both pasteurized and UHT treated BLG beverages were even below the yellowness of freshly prepared WPI-beverages (WPI-A and WPI-B). FIGS. 8 (UHT) and 9 (pasteurised) showed a b*-value of 0.33-0.43 at pH 3.0 and a b*-value of 0.7-1.15 at pH 3.7 in freshly prepared WPI-beverages. This makes the use of beverages comprising at least 6 w/w % bLG as the protein source for whey protein beverages, particularly useful for production of colour-less beverages.

Example 7: Preparation of Heat Sterilised High Protein Beverage Using BLG

BLG samples were prepared wherein about 92 w/w % of the protein was BLG (0.42 w/w % was ALA), and for comparison WPI samples were prepared using WPI-A wherein about 60 w/w % of the protein was BLG (8 w/w % was ALA), the WPI powder had a pH of 3.3).

A BLG isolate powder product (from example 2, pH of powder was 3.9) was dispersed in tap water to produce beverages having protein concentrations ranging from 6.0, 10, 15, 20, 25 and 32 w/w % and adjusted to pH 3.7 using 10% phosphoric acid.

A BLG isolate powder comprising 98.2 w/w % of the protein as BLG (see table 3 above) was dispersed in demineralized water to produce beverages having a protein concentration of 12 w/w %. pH was adjusted to pH 3.7 using 1M HCl.

Figure 10:
FIG. 10 shows images of a 15% BLG beverage pH 3.7 (left) and 6% WPI-a pH 3.7 (right), at 75 C/15 sec.
Figure 11:
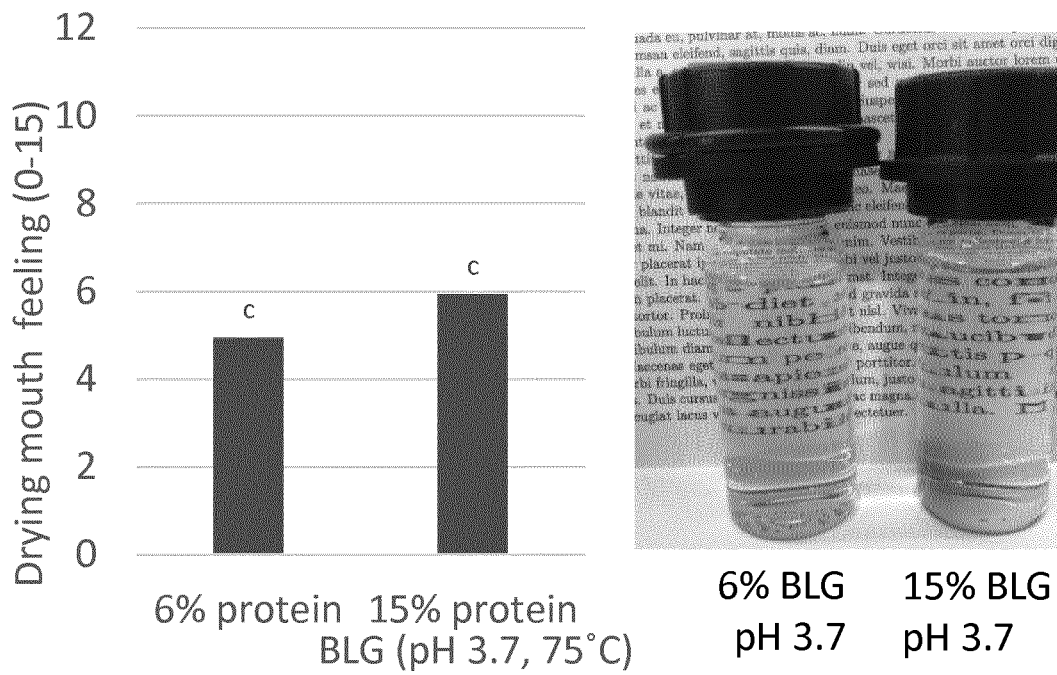
FIG. 11 shows the results of sensory evaluation of high protein BLG beverage compositions and images of 6 w/w % and 15 w/w % BLG samples at pH 3.7.
Figure 12:
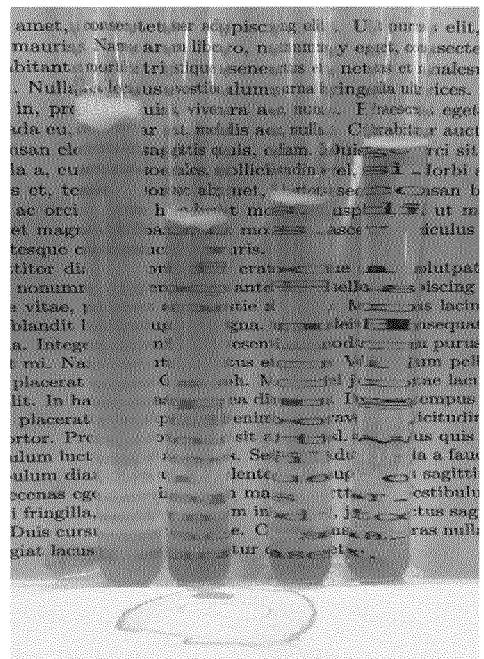
FIG. 12 shows high protein beverage preparations prepared by heating of (left to right) 30, 27.5, 25, 20% BLG beverage preparations at 75° C. for 5 minutes. The viscosity remained low even after heating.

Results:

The results are presented in table 5 above and in FIGS. 10 to 12.

FIG. 10 shows images of 15 w/w % BLG beverage at pH 3.7 heated at 75 C/15 sec that is clear and translucent (left), while a 6% WPI-A at pH 3.7 (right) heated at 75 C/15 sec was opaque.

FIG. 11 shows sensory evaluation of high protein BLG beverage compositions and images of 6 w/w % and 15 w/w % BLG samples at pH 3.7, both samples are clear.

FIG. 12 shows high protein beverage preparations prepared by heating of BLG beverages having a protein content of 32 w/w %, 27.5 w/w %, 25 w/w %, 20 w/w % (left to right) at 75° C. for 5 minutes all samples had a low viscosity and were liquid.

The inventors surprisingly found that all solutions remained at low viscosity even when heated at 75° C. for up to 5 minutes suggesting little or no denaturation.

Viscosities observed at high protein were typical of non-aggregated, native proteins (flow behavior described by (Inthavong, Kharlamova, Nicolai, Chassenieux, & Nicolai, 2016) stating around 10 cP at 200 g/l.

Tryptophan fluorescence spectroscopy confirmed that BLG remains in native conformation as evidenced by having an intrinsic tryptophan emission ratio (I330/I350) of at least 1.11 when heated gently (75° C.) whereas more severe heating caused denaturation as shown by intrinsic tryptophan emission ratio (I330/I350) of less than 1.11.

RP-HPLC analysis confirmed the tryptophan fluorescence results revealing denaturation of a 6% BLG beverage heated at 75° C. for 5 min and 41% denaturation when heated at 95° C. for 5 minutes.

It was shown that viscosity remained low even after heating.

It was found that BLG beverage preparations can be heated above the denaturation temperature. Heating at 95° C./5 min did, however, result in gelation for BLG beverages comprising above 16 w/w % protein whereas 12 w/w % at 95°/5 min, 10 w/w % at 90° C./5 min and 6 w/w % at 120° C./15 sec remained liquid. As evidenced by a lowering of the intrinsic tryptophan emission ratio (I330/I350), at least partial denaturation/aggregation occurs under these heating conditions.

However, it was found that the BLG remained in native conformation, in the BLG beverage preparation comprising 12 w/w % protein when heat treated at 75° C./5 min, as evidenced by an intrinsic tryptophan emission ratio (I330/I350) of 1.17, this beverage was also transparent and in liquid form.

To the inventors big surprise, the sensory panel (for analysis see example 1.11 and FIG. 11) did not identify significant differences in drying mouthfeel of 6 and 15% BLG beverage preparations heated at 75° C.

Example 8: Whey Protein Beverage Preparations with Improved Taste

BLG samples and WPI samples were prepared. The composition of the samples is shown below. The used BLG isolate powder is produced according to example 2.

|  | BLG | WPI -A |
|---|---|---|
| w/w % BLG of protein | 92 | 60 |
| w/w % ALA of protein | 0.42 | 8 |
| pH of powder | 3.9 | 3.0 |

The samples were analysed by a sensory panel of 10 people (see example 1.11). The WPI samples were more yellow and had a higher b*-value and they had a higher turbidity than the BLG beverages, especially at higher pH values. The analysis data is presented in table 6.

For calculation of Delta L* the following formula is used:

$$\text{delta } L^* = L^*_{\text{sample standardized to 6.0 w/w \% protein}} - L^*_{\text{demin. water}}, \text{ measured at room temperature.}$$

Figure 14:
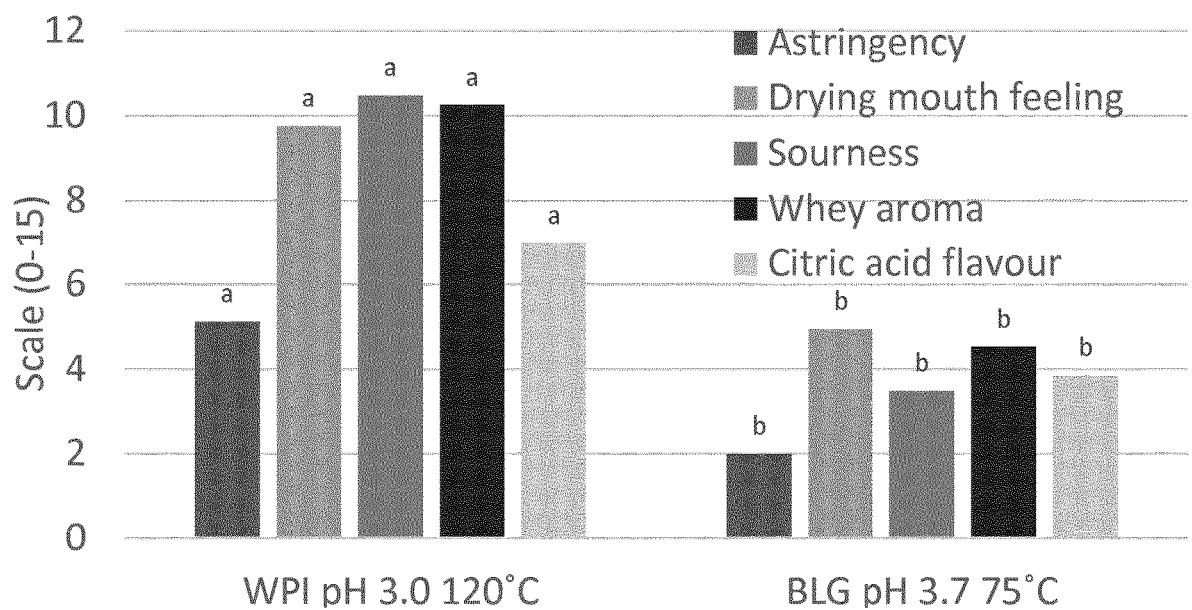
FIG. 14 shows sensory evaluation on beverages (scale from 0 to 15). WPI pH 3.0 120° C./20 s and BLG pH 3.7 75° C./15 sec.

The colour values for demineralized water are:
L*=39,97, a*=0 and b*=−0.22.
Results:

By exploiting the opportunity of increasing pH and decreasing the heating temperature while maintaining clarity and colourless characteristic, a significant difference in the taste between the beverages produced with WPI-A and BLG was observed. The BLG beverage has a lower astringency, drying mouthfeeling, sourness, whey aroma and citric acid flavour compared to the WPI-beverage, shown in FIG. 14.

Figure 15:
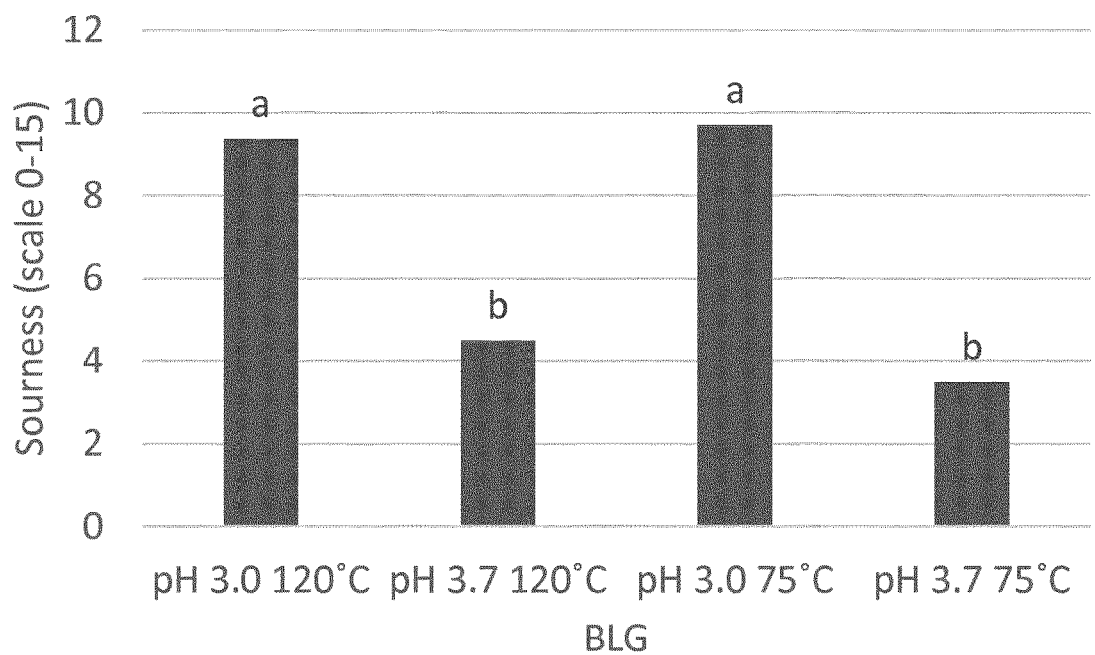
FIG. 15 demonstrates the effect of pH and temperature on taste of protein beverages.

FIG. 15 shows that by increasing the pH to 3.7 before heat-treatment the acid taste in BLG beverages is decreased both at 120° C. and 75° C. while retaining product clarity and low colour.

This was not possible with WPI, because no transparent and clear beverage can be produced at pH 3.7, as seen in table 2 and in FIG. 1.

Figure 16:
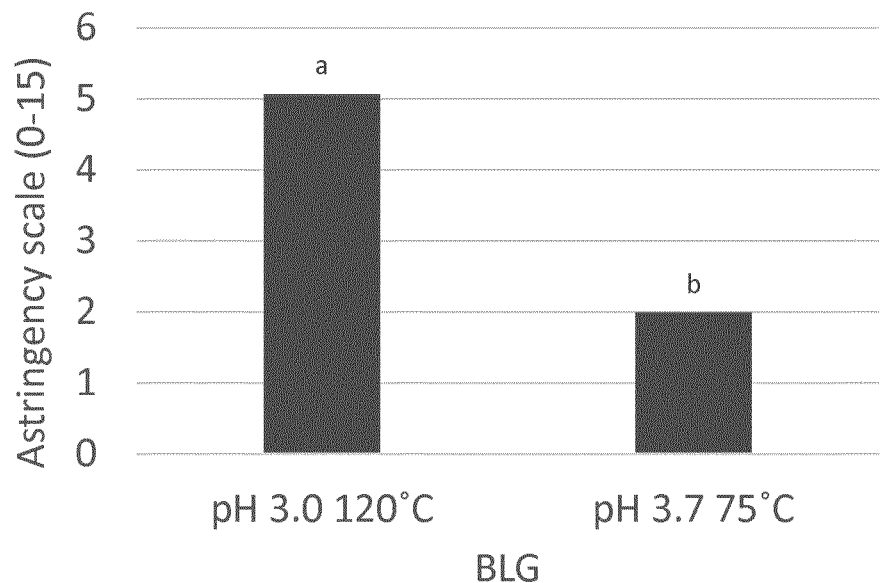
FIG. 16 shows sensory data on the astringency of BLG beverages at pH 3.0 (120° C./20 sec) and pH 3.7 (75° C./15 sec).

FIG. 16 demonstrates a significant reduction in astringency when both temperature and pH are altered from pH 3.0, 120° C./20 sec to pH 3.7, 75° C./15 sec.

Figure 17:
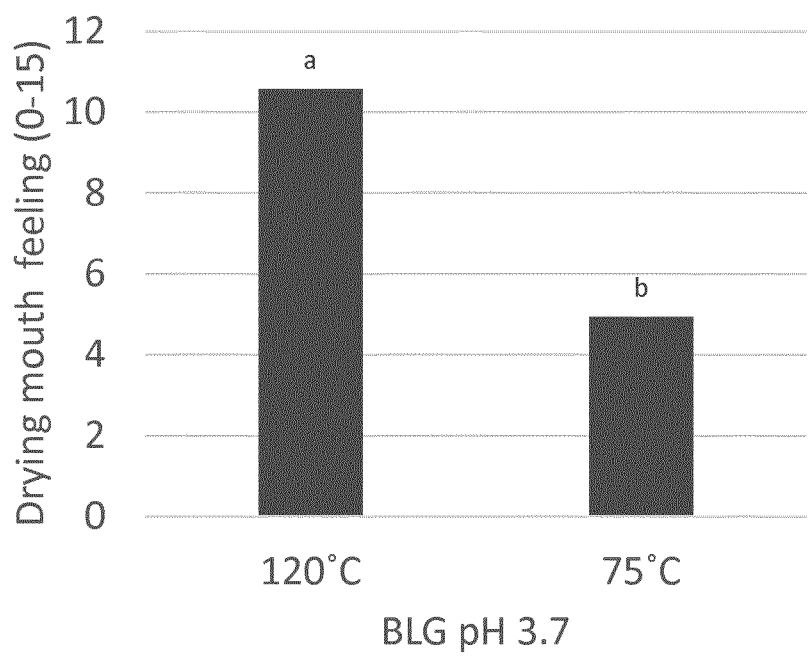
FIG. 17 shows sensory data on the drying mouthfeel of BLG beverages at pH 3.7 heat-treated at 120° C./20 sec or 75° C./15 sec.

FIG. 17 demonstrates a significant decrease in drying mouthfeel by lowering the heating temperature from 120° C./20 sec to 75° C./15 sec (Native at 75° C. versus denaturized proteins at 120° C.).

Figure 18:
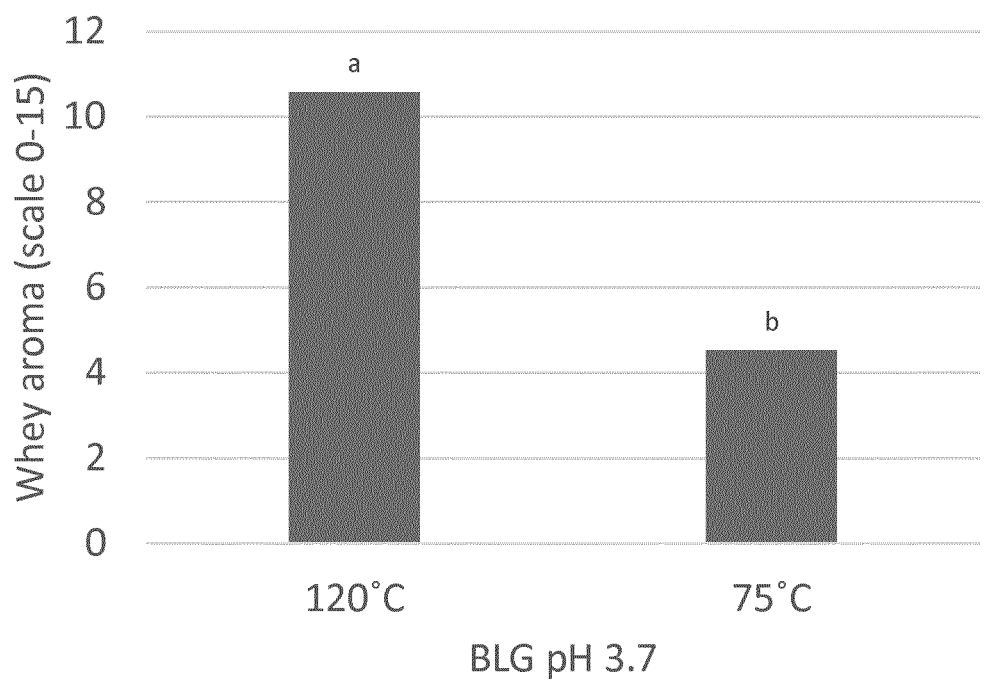
FIG. 18 shows sensory data documenting how the heat-treatment temperature affects the whey aroma.

FIG. 18 demonstrates that whey aroma is reduced when maintaining BLG in native state by using 75 C/15 sec heating at pH 3.7 where transparent and clear, colourless WPI beverages cannot be produced.

It was not possible to produce a clear beverage with WPI at pH 3.7 and heat-treated at 75° C./15 s see also FIG. 3.

Example 9a: Low Colour Sweetened BLG Beverage Preparations

6% w/w BLG beverages were prepared, see composition of the BLG powder used below. The beverages were prepared as described in example 3.

TABLE 6

Analysis data of whey protein beverages prepared from BLG at pH 3.0 and pH 3.7 with heating at 75° C. and 120° C.

|  | WPI-A (6 %) pH 3.0 120° C./20 s | WPI-A (6 %) pH 3.0 75° C./15 s | BLG (6 %) pH 3.0 120° C./20 s | BLG (6 %) pH 3.7 120° C./20 s | BLG (6 %) pH 3.0 75° C./15 s | BLG (6 %) pH 3.7 75° C./15 s | BLG (15 %) pH 3.7 75° C./15 s |
|---|---|---|---|---|---|---|---|
| NTU | 7.17 | 8.63 | 1.02 | 7.0 | 0.88 | 0.99 | 2.6 |
| cP | 2.19 | 1.70 | 1.75 | 2.15 | 1.49 | 1.38 | 2.91 |
| b* | 0.36 ± 0.03 | 0.30 ± 0.03 | −0.01 ± 0.06 | −0.05 ± 0.01 | −0.07 ± 0.05 | −0.07 ± 0.02 | 0.15 ± 0.02 |
| L* | 39.7 ± 0.26 | 39.7 ± 0.2 | 39.7 ± 0.2 | 39.9 ± 0.05 | 39.8 ± 0.12 | 38.9 ± 0.24 | 39.9 ± 0.12 |
| a* | −0.14 ± 0.03 | 0.02 ± 0.05 | −0.01 ± 0.03 | −0.05 ± 0.04 | −0.05 ± 0.01 | −0.08 ± 0.03 | −0.1 ± 0.05 |

Turbididy (NTU), viscosity at 100 s$^{-1}$ (cP) and colour values b*, L* and a*.

Figure 13:
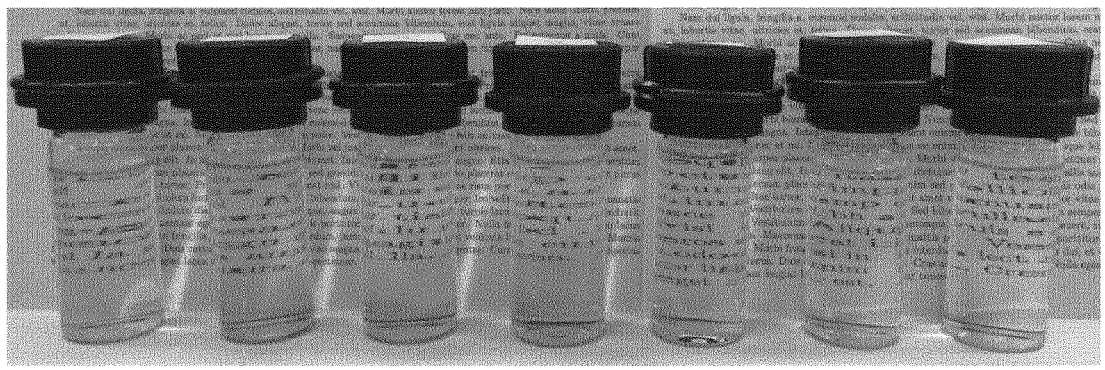
FIG. 13 shows images of different WPI and BLG beverage samples.

Visual appearance of the samples in table 6 is shown in FIG. 13.

The data from the sensory evaluation is shown in FIGS. 14-18.

For calculation of Delta b* the following formula is used:

$$\text{delta } b^* = b^*_{\text{sample standardized to 6.0 w/w \% protein}} - b^*_{\text{demin. water}}, \text{ measured at room temperature.}$$

For calculation of Delta a* the following formula is used:

$$\text{delta } a^* = a^*_{\text{sample standardized to 6.0 w/w \% protein}} - a^*_{\text{demin. water}}, \text{ measured at room temperature.}$$

|  | BLG |
|---|---|
| w/w % BLG of protein | 92 |
| w/w % ALA of protein | 0.42 |
| pH of powder | 3.9 |

The prepared BLG beverages comprised 6% protein and had a pH of 3.7.

8 w/w % sucrose was used as the carbohydrate sucrose. Tests were also performed with the high-intensity sweetener sucralose. The samples were subjected to a heat-treatment of 93° C. for 4 min in a water bath, then cooled in an ice bath.

The visual appearance (example 1.12), colour (example 1.9), turbidity (example 1.7) and viscosity (example 1.8) of the different samples were analyzed.

The results are presented in table 7 below.

TABLE 7

Addition of sucrose to 6 w/w % protein BLG samples.

| pH 3.7 | Turbidity (NTU) | Viscosity (cP)* | Colour |
|---|---|---|---|
| 0% sucrose | 6.71 | 0.939 | L* 39.89 ± 0.02 |
| | | | a* −0.07 ± 0.01 |
| | | | b* 0.01 ± 0.00 |
| 8 w/w % sucrose | 5.91 | 1.52 | L* 39.90 ± 0.08 |
| | | | a* −0.07 ± 0.03 |
| | | | b* 0.05 ± 0.04 |

*Viscoman was used.

Results:

It was found that sweetened BLG beverages can be produced using 8 w/w % sucrose as sweetener and subjecting them to a heat-treatment of 93° C. for 4 min. The addition of 8 w/w % sucrose only had a weak impact on the viscosity, turbidity and clarity, (see table 5) also the colour was not affected by the addition of sucrose.

A BLG beverage with additives typically present in commercial beverages for e.g. sports nutrition was prepared, It comprises a 6% w/w protein BLG beverage at pH 3.7° C., heat-treated for 75° C., 5 min. See the composition in table 8 below.

TABLE 8

Example of a commercial product.

| Ingredients | Amount | Unit |
|---|---|---|
| BLG | 660 | g |
| Trisodium-citrate | 1.0 | g |
| Sucralose 100% | 1.17 | g |
| 10% phosphoric acid | 47 | g |
| Add Water to 10 kg | 9.3 | kg |

TABLE 9

Results of the two recipes.

| | BLG without additives | BLG with additives |
|---|---|---|
| NTU | 1.74 | 1.63 |
| cP | 1.28 | 1.27 |
| b* | −0.07 ± 0.06 | −0.11 ± 0.01 |
| L* | 38.73 ± 0.24 | 39.78 ± 0.13 |
| a* | 0.01 ± 0.04 | 0.01 ± 0.03 |

Results:

It can be seen in table 9 that both the BLG beverages with additives and the BLG beverages without additives remain at low viscosity, transparent and essentially colourless.

Example 9b: Sweetened Low Colour Clear BLG Beverages

In the present example, BLG beverages comprising 2 w/w %, 6 w/w % and 10 wt % proteins, having a pH of 3.7 were prepared as described in Example 3. The BLG powder used for the preparation of the beverages comprised 98.2 w/w % of the protein as BLG, see table 3 (Example 6b). The BLG beverages were furthermore sweetened using sucrose as the carbohydrate source at final concentrations of 5 or 18 w/w % sucrose. The beverages were subjected to heat-treatment at 75° C. or 95° C. for 5 minutes in a water bath and subsequently cooled on ice.

Furthermore, beverages comprising 10 w/w % proteins, 17 w/w % carbohydrate and having a pH of 3.7, using BLG powder from table 3 were prepared. These samples were subjected to heat-treatment at 120° C. for 20 seconds using a plate heat exchanger according to example 4.

The viscosity (example 1.8), turbidity (example 1.7), colour (example 1.9), the nativeness of the proteins determined as intrinsic tryptophan fluorescence emission ratio R=I330/I350 (example 1.1) and insoluble protein matter (example 1.10) of the different samples were analyzed.

The results are presented in table 10 below.

TABLE 10

Clear and sweetened heat-treated protein beverages comprising BLG at pH 3.7.

| Protein % w/w (Energy %) | Carbohydrate % w/w (Energy %) | Temp | Viscosity, cP | Turbidity, NTU | L* | a | b | Δb* | Trp flu ratio I330/I350 | Insoluble portein matter |
|---|---|---|---|---|---|---|---|---|---|---|
| 2 (10) | 18 (90) | 75 | 1.3 | 3 | 39.8 | 0.02 | 0.07 | 0.29 | 1.19 | 0 |
| | | 95 | 2.9 | 5 | 40 | 0.04 | 0.09 | 0.31 | 1.13 | 2 |
| 6 (25) | 18 (75) | 75 | 3.3 | 3 | 39.99 | 0 | 0.16 | 0.38 | 1.18 | 0.2 |
| | | 95 | 3.6 | 5 | 39.95 | −0.02 | 0.2 | 0.42 | 1.07 | 2.1 |
| 6 (55) | 5 (45) | 75 | 2.4 | 2.1 | 39.9 | 0 | 0.1 | 0.32 | 1.17 | 0.2 |
| | | 95 | 2.8 | 6 | 39.8 | 0 | 0.1 | 0.35 | 1.09 | 0.5 |
| 10 (37) | 17 (73) | 120 | 11.9 | 6.11 | 39.95 | −0.06 | 0.25 | 0.47 | n.d. | n.d. |
| 10 (67) | 5 (33) | 75 | 3.1 | 2.8 | 39.9 | 0 | 0.2 | 0.41 | — | 0.4 |
| | | 95 | 6.2 | 7.3 | 40 | 0 | 0.2 | 0.42 | 1.04 | 0.1 |

Results:

The results demonstrate that stable (<15% insoluble protein matter) 2 w/w % beverages containing 18 w/w % carbohydrate in the form of sucrose could be prepared at pH 3.7 by heat-treatment at both 75° C. and 95° C. for 5 minutes.

The viscosity and turbidity of the 2 w/w % BLG beverages were surprisingly low and the beverages were colourless showing delta b* values of 0.29 and 0.31, after heating at 75 and 95° C., respectively. The heating at 75° C. produced beverages consisting of predominantly native whey protein, as demonstrated by the I330/350 ratio of 1.19. It was furthermore surprisingly found that heating at 95° C. for 5 minutes also resulted in predominantly native protein as indicated by a Trp flu ratio of 1.13.

Table 10 further demonstrates that stable colourless BLG beverages with low viscosity and turbidity can be prepared with 6 w/w % protein (comprising 5 or 18 w/w % sucrose) and even with 10 w/w % protein (comprising 5 w/w % sucrose).

It is furthermore demonstrated that BLG of these beverages remains native when heat-treated at 75° C. for 5 minutes as demonstrated by Trp flu ratios above 1.11 and that the beverages are at least partially unfolded/aggregated when heated at 95° C. for 5 minutes as demonstrated by Trp flu ratios below 1.11.

Regarding the 6 w/w % BLG beverage comprising 17% sucrose, which was heat-treated by sterilization at 120° C. for 20 seconds, it had both a low viscosity and turbidity and was colorless showing a delta b* value of 0.47.

All beverages remained remarkably clear and with minimal yellowness even when concentrations of both the protein and carbohydrate sources were increased, see Table 10. This clearly demonstrates that manufacture of BLG beverages in which the energy contribution from carbohydrates from at most 33 E % to at least 90 E % are feasible.

Example 10a: Exemplary Process for Clear BLG Beverage Preparations Comprising Added Minerals The BLG powder used in this example had a pH of 5.5, comprising about 96% w/w of the protein as BLG (and 0.4% w/w of the protein as ALA).

The acidic BLG isolate powder was prepared according to example 2, and the beverage preparations were prepared according to example 5.

High Temperature Heat-Treatment of Beverage Preparations:

6% BLG beverage preparations having a pH of 3.7 were prepared. KCl and CaCl$_2$ were added in liquid form from 1M stock solutions. They were heat-treated at 95° C. for 5 min.
Results:

The results are summarized in table 11 below and in FIG. 19.

Figure 19:
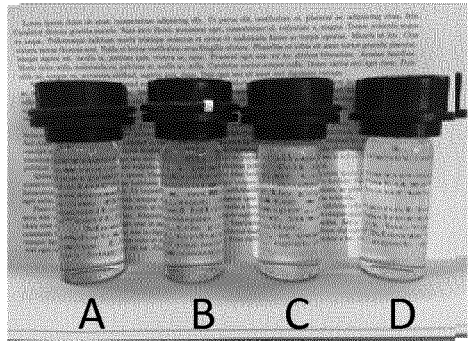
FIG. 19 shows images of 6% BLG beverages enriched with minerals, having a pH of 3.7 and heat-treated at 95° C. for 5 min.

FIG. 19 shows images of 6% BLG beverages heat-treated at 95° C. for 5 min, pH 3.7 and minerals added.
A: 0 mM added mineral
B: 15 mM added CaCl2)
C: 20 mM added KCl
D: 10 mM added KCl and 15 mM CaCl2.

Turbidity of BLG beverage preparations with added minerals (0-20 mM KCl, 0-15 mM CaCl$_2$ or 10 mM CaCl$_2$ and 10 mM) remained below 30 NTU when heated at 95° C. for 5 min at pH 3.7.

Gelation was observed at 30 mM added KCl (turbid gel).
Gelation was observed at 20 mM added CaCl$_2$ (clear gel).

The results clearly suggest that protein composition matters more than mineral difference to WPI, because the amount of added minerals in table 10 greatly exceed the difference between BLG and WPI product(s).

Samples remain clear (see FIG. 19) and had a low viscosity within limits in table 11 below:

TABLE 11

Viscosity and Turbidity of BLG beverages after addition of minerals (CaCl$_2$ and KCl), heated at 95° C. for 5 min, pH 3.7.

| Added CaCl$_2$, mM | Added KCl, mM | Turbidity NTU | Viscosity, cP |
|---|---|---|---|
| 0 | 0 | 13.8 | 0.77 ± 0.1 |
| 15 | 0 | 25.7 | 1.37 ± 0.2 |
| 0 | 20 | 19.6 | 1.08 ± 0.1 |
| 10 | 20 | 23.9 | 1.44 ± 0.3 |

*Viscoman was used.

Low Temperature Heat-Treatment of Beverage Preparations

6% BLG beverage preparations having a pH of 3.7 were prepared. KCl and CaCl$_2$ was added in liquid form from 1M stock solutions. They were heat-treated at pasteurization temperatures of 75° C. for 5 min.
Results.

The inventors surprisingly found that exceptionally high mineral concentrations are allowed when using pasteurization temperatures (75° C., 5 min). See table 12 below.

Figure 20:
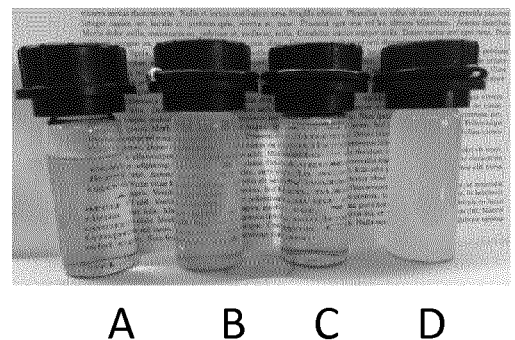
FIG. 20 shows images of 6% BLG beverages having a pH of 3.7, enriched with minerals and heat-treated at 75° C. for 5 min.

FIG. 20 shows images of 6% BLG beverages pH 3.7, heat-treated at 75° C. for 5 min. and minerals added.
A: 0 mM added mineral,
B: 100 mM added KCl,
C: 100 mM added CaCl2,
D: 100 mM added KCl and 100 mM added CaCl2

The beverage preparations remained clear even when 100 mM KCl or 100 mM CaCl$_2$ were added to the beverage composition prior to heating, see FIG. 20. Further, the viscosity was surprisingly low even when both 100 mM KCl and 100 mM CaCl$_2$ were added.

TABLE 12

Viscosity and Turbidity of BLG beverages after addition of minerals (CaCl$_2$ and KCl), heated at 75° C. for 5 min, pH 3.7.

| Added minerals | pH | Protein | Heating | Turbidity NTU | *Viscosity cP avg ± std dev |
|---|---|---|---|---|---|
| 0 | 3.7 | 6% | 75° C., 5 min | 5.4 | 0.8 ± 0.1 |
| 30 mM KCl | 3.7 | 6% | 75° C., 5 min | 6.9 | 0.7 ± 0.1 |
| 40 mM CaCl$_2$ | 3.7 | 6% | 75° C., 5 min | 6.6 | 0.9 ± 0.1 |
| 100 mM KCl | 3.7 | 6% | 75° C., 5 min | 15 | 0.9 ± 0.2 |
| 100 mM CaCl2 | 3.7 | 6% | 75° C., 5 min | 68 | 0.9 ± 0.1 |
| 100 mM KCl + 100 mM CaCl$_2$ | 3.7 | 6% | 75° C., 5 min | 325 | 0.9 ± 0.1 |

*Viscoman was used.

Example 10b: BLG Beverages with Added Minerals

The BLG powder used in this example had a pH of 3.79 comprising about 98.2% w/w of the protein as BLG (see table 3 in Example 6b). The content of the minerals sodium, potassium, calcium and magnesium and phosphor in the powder are all below the detection limit.

High Temperature Heat-Treatment of Beverage Preparations:

BLG beverages comprising 6 wt % protein having a pH of 2.7, 3.0, 3.3 and 3.7 were prepared as described in Example 3. The BLG beverages comprised the minerals NaCl, KCl, $CaCl_2$ and $MgCl_2$ added from stock solutions dissolved to 5, 3 and 1M in demineralized water, respectively. The mineral concentration is described in table 13 below.

TABLE 13

Mineral addition to BLG beverages.

| Sample | Protein w/w % | pH | Energy | Sodium, mM | Potassium, mM | Calcium, mM | Magnesium, mM | Σ(Na,K,Ca,Mg) mM |
|---|---|---|---|---|---|---|---|---|
| A | 6% | 2.7 | 24 | 9.5 | 10.8 | 6.1 | 1.5 | 27.9 |
| B | | 3.0 | kcal/ | 9.6 | 10.9 | 6.2 | 1.5 | 28.2 |
| C | | 3.3 | 100 | 9.6 | 10.9 | 6.2 | 1.5 | 28.2 |
| D | | 3.7 | mL* | 9.5 | 10.8 | 6.1 | 1.5 | 27.9 |

*24 kcal/100 ml: calculation is based on the assumption that: 4 kcal/g protein 9 kcal/g fat, 4 kcal/g carbohydrates The beverages were heat-treated to 95° C. for 5 min using a water bath as outlined in example 4.

The turbidity (example 1.7), the nativeness of the proteins determined as intrinsic tryptophan fluorescence emission ratio R=I330/I350 (example 1.1) and insoluble protein matter (example 1.10) of the different samples were analyzed.

The results are presented in table 14 below.

TABLE 14

Turbidity, nativeness and insoluble particles of BLG beverages after addition of minerals (NaCl, KCl, $CaCl_2$ and $MgCl_2$), heated at 95° C. for 5 min at pH 2.7 to 3.7.

| Sample no | Protein w/w% | pH | Temperature ° C. (5 min.) | Turbidity NTU | Fluorescence Trp ratio I330/350 | Insoluble protein matter % |
|---|---|---|---|---|---|---|
| A | 6% | 2.7 | 95 | 1.5 | 1.15 | 0% |
| B | | 3.0 | | 2.2 | 1.14 | 0% |
| C | | 3.3 | | 3.8 | 1.13 | 1% |
| D | | 3.7 | | 12.3 | 1.10 | 2% |

Results:

The results show that it is possible to produce acidic heat-treated beverages that are both stable and clear after a heat treatment of 95° C. for 5 minutes. The heat-treated BLG beverages comprised both 6 w/w % protein and minerals (Na, K, Ca and Mg) and all had turbidity below 13 NTU and an amount of insoluble particles below 3% at pH 2.7 to 3.7. This is possible even with Na, K, Ca and Mg in the final product summarizing to 27.9-28.2 mM (see the mineral concentration in table 13).

Low Temperature Heat-Treatment of Beverage Preparations with Added Minerals

BLG beverages comprising 6 wt % and 12 wt % protein and having a pH of 2.7, 3.0, 3.3 and 3.7 were prepared as described in Example 3.

The BLG beverages comprised the minerals NaCl, KCl, $CaCl_2$ and $MgCl_2$ added from stock solutions of salts at 5, 3 and 1M in demineralized water, respectively. The mineral addition is shown in table 15 below

TABLE 15

Mineral addition to BLG beverages.

| | Protein weight-% | pH | Energy | Sodium, mM | Potassium, mM | Calcium, mM | Magnesium, mM | Σ(Na,K,Ca,Mg) mM |
|---|---|---|---|---|---|---|---|---|
| E | 6% | 2.7 | 24 kcal/100 mL | 9.5 | 11.0 | 6.0 | 1.5 | 28.0 |
| F | | 3.0 | | 9.6 | 10.8 | 6.0 | 1.5 | 27.9 |
| G | | 3.3 | | 9.9 | 11.2 | 6.3 | 1.5 | 28.9 |
| H | | 3.7 | | 9.6 | 11.1 | 6.0 | 1.5 | 28.2 |
| I | 12% | 2.7 | 48 kcal/100 mL | 18.1 | 20.5 | 11.2 | 2.8 | 52.6 |

TABLE 15-continued

Mineral addition to BLG beverages.

| Protein weight-% | pH | Energy | Sodium, mM | Potassium, mM | Calcium, mM | Magnesium, mM | Σ(Na,K,Ca,Mg) mM |
|---|---|---|---|---|---|---|---|
| J | 3.0 | | 17.4 | 19.5 | 10.8 | 2.8 | 50.6 |
| K | 3.3 | | 17.3 | 19.3 | 10.7 | 2.7 | 50.0 |
| L | 3.7 | | 17.5 | 19.3 | 10.7 | 2.6 | 50.1 |

*24 kcal/100 ml and 48 kcal/100 ml: calculation is based on the assumption that: 4 kcal/g protein, 9 kcal/g fat, 4 kcal/g carbohydrates The beverages were heat treated to 75° C. for 5 min using a water bath as outlined in example 4.

The turbidity (example 1.7) and the nativeness of the proteins determined as intrinsic tryptophan fluorescence emission ratio R=I330/I350 (example 1.1) of the different samples were analyzed.

The results are presented in table 16 below.

TABLE 16

Turbidity and nativeness of 6 w/w % and 12 w/w % BLG beverages after addition of minerals (NaCl, KCl, CaCl₂ and MgCl₂ see table 14), heated at 75° C. for 5 min at pH 2.7 to 3.7.

| Sample | Protein w/w % | pH | Temperature °C. (5 min.) | Turbidity NTU | Fluorescence Trp ratio I330/I350 |
|---|---|---|---|---|---|
| E | 6% | 2.7 | 75 | 1.5 | 1.17 |
| F | | 3.0 | | 1.4 | 1.18 |
| G | | 3.3 | | 1.8 | 1.17 |
| H | | 3.7 | | 3.1 | 1.18 |
| I | 12% | 2.7 | | 2.5 | 1.17 |
| J | | 3.0 | | 2.8 | 1.20 |
| K | | 3.3 | | 3.4 | 1.17 |
| L | | 3.7 | | 10.0 | 1.18 |

Results

The results show that it is possible to produce acidic heat-treated beverages that are clear after a heat treatment of 75° C. for 5 minutes. The beverages showed no aggregation or sedimentation by visual inspection. The heat-treated BLG beverages comprised both 6 w/w % protein and minerals (Na, K, Ca and Mg) and all had turbidity at or below 10 NTU at pH 2.7 to 3.7. This is possible even with Na, K, Ca and Mg in the final product summarizing to 27.9-28.9 mM (see the mineral concentrations in table 15).

It was surprisingly found that native (Trp flu ratio 1.17-1.20) and clear (below 10 NTU) BLG beverages could be produced even with Na, K, Ca and Mg summarizing to 27.9-28.9 mM at 6 w/w % protein and 50-52.6 mM at 12 w/w % protein by heat-treatment at 75° C. for 5 min, see table 16.

It was also surprisingly found that that the 12 w/w % protein BLG beverage at pH 3.0, despite a higher mineral concentration of Na, K, Ca and Mg summarizing to 50.6 mM (sample J) had a turbidity of 2.8 NTU, which is lower than the turbidity of 8.63 NTU measured in a 6% WPI beverage at pH 3.0 comprising a lower concentration of minerals (Na, K, Ca and Mg) in quantities at or below the detection levels, see table 6 of example 8. Detection levels of the different minerals are Na: 0.005 g/100 g=2.2 mM, K: 0.005 g/100 g=1.3 mM, Ca: 0.005/100 g=1.2 mM and Mg: 0.0005/100 g=0.2 mM, which summaries to 4.9 mM.

The surprising results give a lot of new possibilities in production of clear beverages containing additives, which have an effect on protein stability, like minerals. By using a low heat treatment temperature of 75° C., the protein structure remain native and whereby an increased mineral tolerance are achieved, because minerals only increase/induce protein aggregation when the proteins are unfolded.

Example 11a: Milky Whey Protein Beverages, High Temperature Heat-Treatment

An exemplary process for producing an opaque and milky beverage comprising BLG and optionally a source of carbohydrate. BLG powder is dissolved in tap water and adjusted to pH according to Example 3 and thermally treated at 93° C. for 4 minutes. The BLG beverages comprised about 92% w/w of the protein as BLG and about 0.42% w/w of the protein as ALA, the beverages are produced based on an acidic BLG isolate powder having a pH of 3.9 (example 2).

6% BLG beverages were prepared having a pH of 4.3. 8% sucrose was added as carbohydrate source. Turbidity, viscosity, colour and transparency were measured according to the procedures described in examples 1.7, 1.8, 1.9 as well as the beverage stability as in example 1.10.

The results are presented in tables 17 and 18 below and in FIG. 21.

TABLE 17

Stability of milky beverages comprising BLG, heat-treatment of 93° C./4 min. 6% protein and pH 4.3

| 0% sucrose | Brix % | Turbidity (NTU) | *Viscosity (cP) | Colour |
|---|---|---|---|---|
| Before centrifugation | 7.2 | >10000 | 1.15 | L* 85.15 ± 0.05<br>a* −1.24 ± 0.01<br>b* −1.95 ± 0.00 |
| After 3000 g 5 min. | 6.6 | <10000 | 0.87 | L* 79.21 ± 0.20<br>a* −1.72 ± 0.01<br>b* −4.12 ± 0.01 |

*Viscoman was used.

TABLE 18

Stability of a milky BLG beverage also comprising sucrose, heat-treatment of 93° C./4 min. 6% protein and pH 4.3

| 8% sucrose | Brix % | Turbidity (NTU) | Viscosity (cP) | Colour |
|---|---|---|---|---|
| Before centrifugation | 14.2 | >10000 | 1.4 | L* 81.68 ± 0.19<br>a* 4.51 ± 0.03<br>b* −3.01 ± 0.01 |
| After 3000 g 5 min. | 14.4 | >10000 | 1.33 | L* 76.55 ± 0.20<br>a* −1.88 ± 0.02<br>b* −4.87 ± 0.01 |

WPI samples were prepared comprising 6% protein and having a pH of 4.3 The WPI samples were thermally treated at 94° C. for 5 minutes. 0% sucrose or 8% sucrose was added to the WPI-A sample, while 0% sucrose or 6% sucrose was added to the WPI-B sample.

|  | BLG | WPI-A | WPI-B |
|---|---|---|---|
| w/w % BLG of protein | 92 | 60 | 8 |
| w/w % ALA of protein | 0.42 | 57 | 10 |
| pH of powder | 3.9 | 3.0 | 6.8 |

Figure 21:
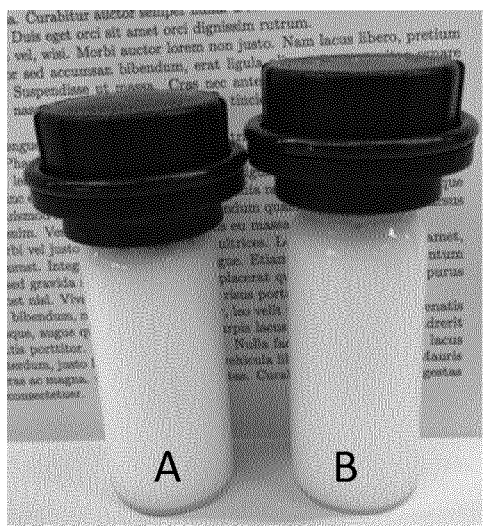
FIG. 21 illustrates the stability of milky BLG beverages at pH 4.3, with and without added sucrose when heat-treated at 93° C. for 4 minutes.
Figure 21:
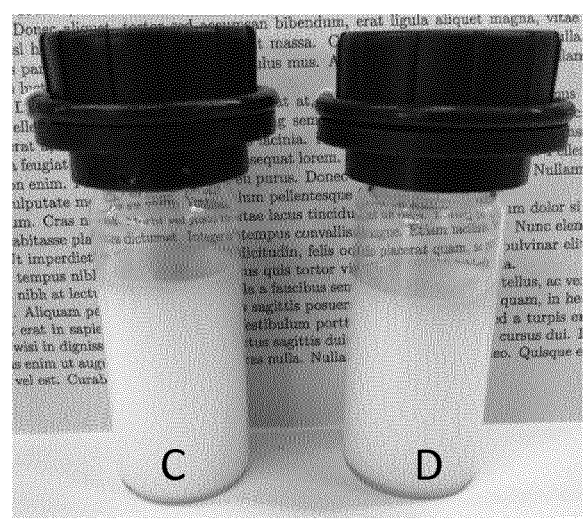

Results:

FIG. 21 illustrates stability of milky BLG beverages, pH 4.3, with and without sucrose, heat-treated at 93° C. for 4 minutes. A: 0% sucrose (before centrifugation), B:8% sucrose (before centrifugation), C: 0% sucrose (after centrifugation), D: 8% sucrose (after centrifugation)

The results presented in tables 17 and 18 and FIG. 21 demonstrate that high end pH such as pH 4.3 enable manufacture of milky beverages, which is preferred in some embodiments of the invention, for instance when the consumer prefers a whey protein beverage with a milky appearance. It was also found that even at a pH of 4.3 the viscosity was low, both for preparations with and without sucrose.

The colour also remained neutral. This is in particular preferred by the consumers, who prefer that a milky beverage does not have a yellowish colour. A yellowish colour is seen when the b*value is high and positive.

It was also found that the beverages were stable as evidenced by <15% decrease in protein and high turbidity also after centrifugation at 3000×g for 5 minutes.

It was not possible to produce milky 6 w/w % protein WPI beverages based on WPI-A or WPI-B having a pH of 4.3 as they gelled and thus had a high viscosity, this applied for both WPI samples both with and without added sucrose.

Example 11b: Milky Whey Protein Beverages, High Temperature Heat-Treatment

Milky High Temperature Treated Beverages without Carbohydrate:

The BLG powder used in this example had a pH of 3.79, comprising about 98.2% w/w of the protein as BLG (see table 3 in example 6b).

BLG beverages comprising 6 wt % protein having a pH of 4.2 and 4.4 were prepared as described in Example 3 using 0.75M NaOH.

The beverages were heat treated to 95° C. for 5 min using a water bath as outlined in example 4.

The turbidity (example 1.7), the viscosity (example 1.8), the nativeness of the proteins determined as intrinsic tryptophan fluorescence emission ratio R=I330/I350 (example 1.1), the colour (example 1.9) and insoluble protein matter (example 1.10) of the different samples were analyzed.

The results are presented in table 19 below.

TABLE 19

Milky 6 wt % BLG beverages, heat-treated at 95° C. for 5 min at pH 4.2 and 4.4.

| 6% protein-95° C. for 5 min. | pH 4.2 | pH 4.4 |
|---|---|---|
| Turbidity NTU | 3269 | >11000 |
| Viscosity cP | 2.8 | 2.0 |
| Fluorescence Trp ratio I330/I350 | 0.99 | 1.01 |

TABLE 19-continued

Milky 6 wt % BLG beverages, heat-treated at 95° C. for 5 min at pH 4.2 and 4.4.

| 6% protein-95° C. for 5 min. | pH 4.2 | pH 4.4 |
|---|---|---|
| b | −8.87 | −1.22 |
| a | −1.83 | −0.82 |
| L* | 50.88 | 86.26 |
| Δb* | −8.65 | −1.00 |
| Δa* | −1.83 | −0.82 |
| ΔL* | 10.91 | 46.29 |
| Insoluble particles | 1% | 5% |

For calculation of Delta b* the following formula is used:

$$\text{delta } b^* = b^*_{\text{sample standardized to 6.0 w/w \% protein}} - b^*_{\text{demin. water}}\text{, measured at room temperature.}$$

For calculation of Delta a* the following formula is used:

$$\text{delta } a^* = a^*_{\text{sample standardized to 6.0 w/w \% protein}} - a^*_{\text{demin. water}}\text{, measured at room temperature.}$$

For calculation of Delta L* the following formula is used:

$$\text{delta } L^* = L^*_{\text{sample standardized to 6.0 w/w \% protein}} - L^*_{\text{demin. water}}\text{, measured at room temperature.}$$

The colour values for demineralized water are: $L^*=39.97$, $a^*=0$ and $b^*=-0.22$.

Results:

The results presented in table 19 demonstrate that high end pH, such as even at pH 4.4, enable the manufacture of milky beverages, which is preferred in some embodiments of the invention, for instance when the consumer prefers a whey protein beverage with a milky appearance.

It was surprisingly found that stable (insoluble protein matter below 5%) milky BLG beverages (turbidity of at least 11000 NTU) with low viscosity (below 2 cP) successfully could be prepared even at a pH value of 4.4, when the beverages were heat treated at 95° C. for 5 min.

As evidenced by the intrinsic tryptophan emission ratio (I330/I350) of 0.99 at pH 4.2 and 1.01 at pH 4.4, at least partial denaturation/aggregation occurs at both pH 4.2 and 4.4 when the beverages were heat treated at 95° C. for 5 min.

Compared to this, it is described in Example 11a that it was not possible to produce milky 6 w/w % protein WPI beverages based on WPI-A or WPI-B having a pH of 4.3 as they gelled and thus had a high viscosity.

Milky High Temperature Treated Beverages with a Source of Carbohydrate:

The BLG powder used in this example had a pH of 3.79, comprising about 98.2% w/w of the protein as BLG (see table 3 in example 6b).

BLG beverages comprising 2 wt % and 6 wt % protein were sweetened using sucrose as the carbohydrate source to final sucrose concentrations of 5 or 18 w/w % sucrose and pH was adjusted to 4.2 they were prepared as described in Example 3.

The BLG beverages were subjected to a heat-treatment of 95° C. for 5 minutes using a plate heat exchanger as outlined in example 4.

The turbidity (example 1.7), the viscosity (example 1.8), the nativeness of the proteins determined as intrinsic tryptophan fluorescence emission ratio R=I330/I350 (example 1.1), the colour (example 1.9) and insoluble protein matter (example 1.10) of the different samples were analyzed.

The results are presented in table 20 below. The Energy percentage (% E) of protein and carbohydrate is calculated.

TABLE 20

Milky 2 wt % and 6 wt % BLG beverages, heat-treated at 95° C. for 5 min at pH 4.2 comprising carbohydrates.

| Beverage | M | N | O |
|---|---|---|---|
| pH 4.2 95° C. for 5 min. | % of total energy: Protein 10% E Carbo. 90% E Protein (2 w/w %) Sucrose (18 w/w %) | % of total energy: Protein 25% E Carbo. 75% E Protein (6 w/w %) Sucrose (18 w/w %) | % of total energy: Protein 54.5% E Carbo. 45.5% E Protein (6 w/w %) Sucrose (5 w/w %) |
| Turbidity NTU | 1276 | 1754 | 1435 |
| Viscosity cP | 2.7 | 10.3 | 3.9 |
| Fluorescence Trp ratio I330/350 | 1.03 | 0.99 | 0.99 |
| Insoluble protein matter % | 0 | 0.8 | 1.6 |
| b* | −9.46 | −7.64 | −5.5 |
| a* | −0.99 | −0.83 | −0.2 |
| L* | 44.93 | 42.55 | 37.4 |
| Δb* | −9.24 | −7.42 | −5.28 |
| Δa* | −0.99 | −0.83 | −0.22 |
| ΔL* | 4.96 | 2.58 | −2.58 |

Results:

The results presented in table 20 demonstrate that high end pH, such as pH 4.2, and a heat treatment of 95° C. for 5 minutes enable the manufacture of milky beverages comprising both proteins and carbohydrates, wherein the carbohydrates comprises 45.5%, 75% and 90% of the total beverage energy content. All three beverages had a high turbidity above 1276 NTU and a low viscosity at or below 10.3 cP. The beverages were all stable with less than 1.6% insoluble protein matter. At least partial unfolding/aggregation occurred in all three beverages comprising both proteins and carbohydrates. This is evidenced by the intrinsic tryptophan emission ratio (I330/I350) at or below 1.03.

All beverages had a milky and opaque appearance.

Example 12a: Milky Whey Protein Beverages, Low Temperature Heat-Treatment for Prolonged Time An exemplary process for producing a milky beverage comprising BLG at different pH. BLG powder is dissolved in tap water and adjusted to pH 4.2-4.5 using 10% phosphoric acid according to Example 3. The preparations were thermally treated at 75° C. for 5 minutes and had a protein content of 6% w/w. The BLG beverages comprised about 92% w/w of the protein as BLG and 0.42% w/w of the protein as ALA and are produced based on a BLG powder having a pH of 3.9.

Turbidity, viscosity, colour and visual transparency were measured according to the procedures described in examples 1.7, 1.8, 1.9 and 1.12.

The results are presented in table 21 below and in FIG. 22.

Figure 22:
FIG. 22 shows images of opaque 6% protein BLG beverages having a pH of 4.2 or 4-5 and prepared by heating at 75° C. for 5 min.

FIG. 22 shows images of opaque 6% protein BLG beverages prepared by heating at 75° C. for 5 min at pH 4.2-4.5.

TABLE 21

Properties of opaque BLG beverages at pH 4.2-4.5 after heating at 75° C. for 5 minutes.

|  | pH 4.2 | pH 4.5 |
|---|---|---|
| Turbidity (NTU) | 2489.6 | 4282.9 |
| Viscosity (cP) | 0.954 | 0.943 |
| L* | 32.33 ± 0.02 | 40.14 ± 0.06 |

TABLE 21-continued

Properties of opaque BLG beverages at pH 4.2-4.5 after heating at 75° C. for 5 minutes.

|  | pH 4.2 | pH 4.5 |
|---|---|---|
| a* | −0.23 ± 0.05 | −0.67 ± 0.02 |
| b* | −1.34 ± 0.01 | −3.42 ± 0.01 |

Results:

It was found that the beverages at pH 4.2 to 4.5 had a milky and opaque appearance and a high turbidity, while still having a low viscosity.

Example 12b: Milky Whey Protein Beverages, Low Temperature Heat-Treatment for Prolonged Time In the present example, BLG beverages comprising 6 wt % proteins and having a pH of 4.2, 4.4 and 4.6 were prepared as described in Example 3. The BLG powder used for the preparation of the beverages comprised 98.2 w/w % of the protein as BLG, see table 3 in example 6b.

The final pH was adjusted to 4.2, 4.4 and 4.6 using 0.75 M NaOH. The beverages were heat treated at 75° C. for 5 min using a water bath as outlined in example 4.

The turbidity (example 1.7), the viscosity (example 1.8), the amount of insoluble particles (example 1.10) and the colour (example 1.9) of the different samples were analyzed.

The results are presented in table 21.

TABLE 21

Properties of opaque BLG beverages at pH 4.2-4.6 after heating at 75° C. for 5 minutes.

| 6% protein 75° C. for 5 min. | pH 4.2 | pH 4.4 | pH 4.6 |
|---|---|---|---|
| Turbidity NTU | 1963.6 | 4503.4 | 6257.4 |
| Viscosity cP | 1.1 | 1.5 | 1.1 |
| Insoluble particles % | 1% | 7% | 4% |
| b* | −3.09 | −4.9 | −4.23 |
| a* | −0.22 | −0.95 | −1.01 |
| L* | 34.92 | 46.93 | 53.67 |
| Δb* | −2.87 | −4.68 | −4.01 |
| Δa* | −0.22 | −0.95 | −1.01 |
| ΔL* | −5.05 | 6.96 | 13.7 |

Results:

It was surprisingly found that stable (<7% insoluble particles) milky beverages with low viscosity could be produced by thermal treatment at 75° C. for up to at least 5 min even at pH 4.2, pH 4.4 and pH 4.6 and display even lower viscosity than WPI-A and WPI-B beverages at pH 3.7 in example 6a.

Example 12c: Milky Whey Protein Beverages, Low Temperature Heat-Treatment for Prolonged Time with Carbohydrates The BLG powder used in this example had a pH of 3.79, comprising about 98.2% w/w of the protein as BLG (see table 3 in example 6b).

BLG beverages comprising 6 wt % and 10 wt % protein were sweetened using sucrose as the carbohydrate source at final concentrations of 5 or 18 w/w % of sucrose. pH was adjusted to 4.2 using 0.75 M NaOH and the beverages were prepared as described in Example 3.

The BLG beverages were subjected to a heat-treatment of 75° C. for 5 minutes using a water bath as outlined in example 4.

The turbidity (example 1.7), the viscosity (example 1.8) and insoluble protein matter (example 1.10) of the different samples were analyzed.

The results are presented in table 22 below. The Energy percentage (% E) of protein and carbohydrate is calculated.

TABLE 22

Milky 6 wt % and 10 wt % BLG beverages, heat-treated at 75° C. for 5 min at pH 4.2 comprising carbohydrates.

| pH 4.2<br>75° C. for<br>5 min. | % of total energy:<br>Protein 25% E<br>Carbo. 75% E<br>Protein<br>(6 w/w %)<br>Sucrose<br>(18 w/w %) | % of total energy:<br>Protein 54.5% E<br>Carbo. 45.5% E<br>Protein<br>(6 w/w %)<br>Sucrose<br>(5 w/w %) | % of total energy:<br>Protein 66.7% E<br>Carbo. 33.3% E<br>Protein<br>(10 w/w %)<br>Sucrose<br>(5 w/w %) |
|---|---|---|---|
| Turbidity NTU | 407 | 879.7 | 1717.3 |
| Viscosity cP | 3.2 | 2.8 | 4.5 |
| Insoluble protein matter % | 0.2 | 0.7 | 0.7 |

Results:

The results presented in table 22 demonstrate that high end pH, such as pH 4.2, enable manufacture of milky beverages comprising both proteins and carbohydrates heat-treated at 75° C. for 5 min.

It was surprisingly found that the milky beverages were stable with less than 0.7% insoluble particles. The milky beverages had a low viscosity at pH 4.2 and the carbohydrate comprised 33.3%, 45.5% and 75% of the total energy content.

Example 13: Colourless Whey Protein Beverage Containing>85% bLG

Beverage preparations were prepared wherein about 92% w/w of the protein is BLG and about 0.42% w/w of the protein is ALA (pH of the BLG-isolate powder was 3.9), see example 3.

For comparison whey protein samples comprising SPI (serum protein isolate) comprising about 80% w/w BLG and about 4% w/w ALA were prepared (pH of the SPI-powder was 6.7).

The samples had a protein content of 6% w/w. pH of the beverages were adjusted to pH 3.7. Turbidity, viscosity, colour and transparency of the preparations were measured according to the procedures described in examples 1.7, 1.8, 1.9 as well as beverage stability as in example 1.10.

Figure 23:
FIG. 23 shows images of BLG and SPI beverages having a pH of 3.7 and heat-treated at 75° C. for 5 min.
Figure 24:
FIG. 24 shows images of BLG and SPI beverages having a pH of 3.7.

The results are presented in table 23 below and in FIGS. 23 and 24.

TABLE 23

Properties of BLG and SPI beverages subjected to different heat-treatments.

| pH 3.7 | BLG, without heat treament | SPI, without heat-treatment | SPI 75° C. 5 min. | SPI 95° C. 5 min. |
|---|---|---|---|---|
| Turbidity NTU | 1.47 | 21.82 | 52.64 | 74.21 |
| Viscosity (cP) | 1.31 | 0.764 | 1.07 | 1.44 |
| L* | 39.86 ± 0.03 | 39.41 ± 0.05 | 39.36 ± 0.07 | 39.36 ± 0.08 |
| a* | −0.03 ± 0.03 | −0.30 ± 0.01 | −0.29 ± 0.02 | −0.28 ± 0.02 |
| b* | −0.08 ± 0.04 | 1.53 ± 0.01 | 1.43 ± 0.02 | 1.52 ± 0.01 |

The viscosity was measured on Viscomann (example 1.8).

Results:

It was found that the viscosity of SPI (about 80% BLG, about 4% ALA) increased more due to heat-treatment compared to the BLG preparations at pH 3.7.

Further the SPI beverages had higher b*values and therefore a more yellowish colour than the BLG samples.

Example 14a: Nutritional Whey Protein Beverage Comprising 285% BLG, a Source of Carbohydrate and a Source of Fat Example 14a describes an exemplary process for preparing a heat sterilized beverage preparation wherein at least 85% w/w of the protein is BLG.

The inventors have surprisingly found that the BLG beverages (≥85%) accept surprisingly large mineral concentrations to be present during a heat-treatment by pasteurization at 75° C. with holding times for up to at least 5 minutes (Example 10a) since a 6% nutritional composition with 100 mM added KCl and 100 mM added $CaCl_2$ remained liquid (viscosity at about 1 cP) even after heating at 75° C. for 5 minutes.

Since heat stability of whey proteins often suffer at high mineral dosages, we therefore investigated further the opportunity to produce nutritionally complete acid BLG beverages to produce sterilized nutritional beverages comprising ≥85% BLG, a source of carbohydrate, a source of fat and minerals in a combination that meet current FSMP (Foods for Special Medical Purposes) requirements.

Dissolving protein and mixing with lipids and carbohydrates in example ratios based on the energy distribution as described in Table 24.

Food grade acid and minerals were selected to accommodate requirements set for food for special medical purposes (FSMP).

Vitamins may further be supplied in the beverage to meet FSMP requirements and produce nutritionally complete nutritional supplements.

TABLE 24

Composition of exemplary nutritional composition containing sources of protein, carbohydrate and fat.

| Component | Source | Concentration, % | Energy, kJ/100 mL | Energy distribution E % |
|---|---|---|---|---|
| Protein | BLG | 6 | 100.8 | 20% |
| Carbohydrate | Sucrose | 13.5 | 226.8 | 45% |
| Fat | Rapeseed oil | 4.7 | 176.4 | 35% |
| Sum | | 24.2 | 504 | |

A 6 w/w % BLG nutritional beverage also comprising 13.5 w/w % sucrose and 4.7 w/w % rapeseed oil was mixed at 70° C. Composition of protein, fat and carbohydrate selected to accommodate recommendations for medical nutrition.

In certain aspects, (1) 40 mM KCl and 14 mM CaCl2 or (2) 80 mM KCl and 28 mM CaCl2 was added together with additional components or (3) without further mineral additions as indicated in table 24.

The solutions were homogenized at 200 bar.

The solution was thermally treated by immersion in water bath at 75° C. or 95° C. for 5 minutes and cooled on ice.

TABLE 25

Nutritional compositions containing BLG, a source of carbohydrate, fats and added minerals.

| Treatment | Minerals | Turbidity NTU | Trp ratio | Viscosity (cP or mPas) |
|---|---|---|---|---|
| None | As is | 3607 | 1.18 | 2.93 |
| 75C/5 min | As is | 3349 | 1.18 | 3.20 |
| 75C/5 min (1) | 40 mM KCl 14 mM CaCl2 | 3373 | 1.18 | 3.25 |
| 75C/5 min (2) | 80 mM KCl 24 mM CaCl2 | 3274 | 1.17 | 2.96 |

Results:

It was found that opaque beverages can be produced using BLG in combination with sources of fat and carbohydrates by heating at 75° C. and 95° C.

At 75° C. it remains in native state (it had a Trp flu ratio of 1.18 despite that it comprised fat), while it causes denaturation (Trp flu) at 95 degrees C. The viscosity remains low. As it was possibly to maintain the native conformation it enables administration of minerals which are critical for medical nutrition (FSMP requirements). Further the ability of the nutritional compositions to remain liquid in the presence of selected minerals clearly suggests the feasibility for use within medical nutrition.

Example 14b: Nutritional Whey Protein Beverages Containing a Source of Carbohydrate and Fat and Added Minerals Example 14b describes a process for producing milky beverages comprising BLG, a source of carbohydrate, a source of fat and added minerals that comply with FSMP requirements.

Since heat stability of whey proteins often suffer at high mineral dosages, this example investigated the opportunity to prepare nutritionally complete acid BLG beverages that meet current FSMP (Food for special medical purposes) requirements by sterilizing nutritional beverages comprising a source of BLG (98,2% purity) at 6-16.7% w/w and further containing a source of fat (rapeseed oil) at 2.7-7.3% w/w and sucrose at 7.5-18% w/w (as described in table 26 below).

The pH and mineral composition using food grade acids and salts to reach pH 3.5 and levels of Na, K, Ca and Mg in the final beverage is also shown in table 26. Vitamins may further be supplied to secure that BLG beverages meet FSMP requirements and produce nutritionally complete nutritional supplements.

The BLG powder used in this example had a pH of 3.79, comprising about 98.2% w/w of the protein as BLG (see table 3 in example 6b). The content of the minerals sodium, potassium, calcium and magnesium and phosphor in the BLG powder are all below the detection limit.

TABLE 26

Mineral addition to BLG beverages

| pH | bLG w/w% (E %) | Rapeseed oil in w/w % (E %) | Sucrose w/w % (E %) | Energy kcal/100 mL | Sodium, mM | Potassium, mM | Calcium, mM | Magnesium, mM | Σ(Na,K,Ca,Mg) |
|---|---|---|---|---|---|---|---|---|---|
| 3.5 | 6 (20) | 4.7 (35) | 13.5 (45) | 120 | 46.8 | 52.1 | 30.2 | 4.4 | 133.4 |
| 3.5 | 6 (20) | 2.7 (20) | 18 (60) | 120 | 46.1 | 51.7 | 30.4 | 4.4 | 132.6 |
| 3.5 | 6 (20) | 7.3 (55) | 7.5 (25) | 120 | 45.2 | 51.2 | 29.9 | 4.5 | 130.8 |
| 3.5 | 16.7 (49) | 3.3 (22) | 10 (29) | 164 | 57.4 | 65.1 | 39.1 | 5.6 | 167.1 |

The measured content of Na, K, Mg and Ca (ICP-MS example 1.19) in the final heat sterilized nutritional compositions shown in Table 26 complies with FSMP requirements and summarize to 131-167 mM. These results clearly suggest the feasibility for use of bLG within medical nutrition The nutritional beverage compositions were prepared as described in Example 3 and heat-treated by heating at 75° C. for 5 minutes in vials immersed in water baths according to Example 4.

The viscosity (example 1.8), turbidity (example 1.7), colour (example 1.9), the nativeness of the proteins determined as intrinsic tryptophan fluorescence emission ratio R=I330/I350 (example 1.1) and insoluble protein matter (example 1.10) of the different samples were analyzed.

The results are presented in table 27 below.

TABLE 27

Viscosity, turbidity, colour, nativeness and insoluble protein matter of BLG beverages after addition of minerals (NaC, KCl, CaCl$_2$ and MgCl$_2$) heated at 75° C. for 5 min at pH 3.5.

| bLG w/w % | Rape seed oil w/w % | Sucrose w/w % | Viscosity cP | Turbidity NTU | L* | a | b | Δb* | Trp I330/350 | Insoluble matter protein |
|---|---|---|---|---|---|---|---|---|---|---|
| 6 | 4.7 | 13.5 | 3.0 | 7070 | 50.29 | −0.85 | −2.53 | −2.31 | 1.18 | 0% |
| 6 | 2.7 | 18 | 3.6 | 5250 | 41.53 | −0.63 | −2.58 | −2.36 | 1.18 | 0% |

TABLE 27-continued

Viscosity, turbidity, colour, nativeness and insoluble protein matter of BLG beverages
after addition of minerals (NaC , KCl, CaCl$_2$ and MgCl$_2$) heated at 75° C. for 5 min at pH 3.5.

| bLG w/w % | Rape seed oil w/w % | Sucrose w/w % | Viscosity cP | Turbidity NTU | L* | a | b | Δb* | Trp I330/ 350 | Insoluble matter protein |
|---|---|---|---|---|---|---|---|---|---|---|
| 6 | 7.3 | 7.5 | 2.8 | 8357 | n.d | n.d | n.d | n.d | 1.17 | 0% |
| 16.7 | 3.3 | 10 | 14.2 | >11000 | 64.64 | −1.21 | −2.45 | −2.23 | 1.18 | 0% |

Results:

It was surprisingly found that milky beverages can be produced using a source of BLG comprising more than 98.2% of the protein as BLG, in combination with sources of both fat and carbohydrates by heating at 75° C. for 5 minutes. This is possible even in the presence of a high amount of added Na, K, Ca and Mg having summarized concentrations of these minerals of 130-167 mM.

At 75° C. BLG remains native (Trp flu ratio≥1.17) and stable milky (Turbidity>5000 NTU) beverages with remarkably low level of insoluble protein matter (<1% insoluble protein matter after 3000×g centrifugation) and low viscosities were prepared despite the presence of a high amount of added minerals. The viscosity increases slightly to 14.2 cP when total dry matter content is increased (16.7% bLG, 3.34% fat, 10% sucrose). The beverages were essentially colorless.

Example 15: Low Phosphorus Protein Beverage

Four low phosphorus beverage samples are prepared using the purified BLG product from Example 3 (the crystal preparation obtained from feed 3 PCTEP2017/084553). All the dry ingredients are mixed with demineralised water to obtain 10 kg of each sample and allowed to hydrate for 1 hour at 10 degrees C.

| Ingredient (% w/w) | Beverage sample | | | |
|---|---|---|---|---|
| | A | B | C | D |
| Dried, purified BLG from Ex. 3, feed 3 of PCT/EP2017/084553 | 5.0 | 10.0 | 5.0 | 10.0 |

-continued

| Ingredient (% w/w) | Beverage sample | | | |
|---|---|---|---|---|
| | A | B | C | D |
| Citric acid | To pH 3.5 | To pH 3.5 | To pH 3.0 | To pH 3.0 |
| Sucrose | 10 | 10 | 10 | 10 |
| Demineralised water | To 100% | To 100% | To 100% | To 100% |

The samples are subjected to 90 degrees C. for 180 seconds and filled aseptically in sterile containers.

The packaged beverages have a shelf-life of at least 1 year at ambient temperature.

All ingredients used for preparing the 5 beverages are low in phosphorus and the obtained beverages therefore have a phosphorus content much lower than 80 mg/100 g protein. The four beverages are therefore suitable for use as protein beverages for kidney disease patients.

Low Phosphorous BIG Beverages Comprising Carbohydrates and Fat:

We also demonstrated that beverages with remarkably low phosphorous contents of less than 1 mg phosphorous per gram of protein in in the final beverage can be produced when using the BLG protein powder, comprising at least 85% w/w of BLG (which is particularly low in phosphorous, table 3) in combination with sucrose and fat sources that also contain low levels of phosphor as shown in Table 28. This is demonstrated across a large protein concentration range from 6% w/w to 20% w/w of bLG.

TABLE 28

Energy and phosphorous content in exemplary bLG beverages especially suited for kidney disease patients. A star (*) indicates the calculated phosphorus content of exemplary bLG beverages based on the maximum possible phosphorus content of the used bLG powders.

| pH | Temp ° C./min/sec | bLG w/w % (E %) | Rapeseed oil in w/w % (E %) | Sucrose w/w % (E %) | Energy k cal/100 mL | Phosphorous mg/100 g protein |
|---|---|---|---|---|---|---|
| 3.5 | 75° C./5 min | 6.0 (20) | 4.7 (35) | 13.5 (45) | 120 | 20* |
| 3.5 | 75° C./5 min | 6.0 (20) | 2.7 (20) | 18.0 (60) | 120 | 20* |
| 3.5 | 75° C./5 min | 6.0 (20) | 7.3 (55) | 7.5 (25) | 120 | 21* |
| 3.5 | 120° C./20 sec | 7 (14) | 10 (46) | 20 (40) | 120 | not measured |
| 3.5 | 75° C./5 min | 20 (49) | 4 (22) | 12 (29) | 164 | 20* |

TABLE 28-continued

Energy and phosphorous content in exemplary bLG beverages especially suited for kidney disease patients. A star (*) indicates the calculated phosphorus content of exemplary bLG beverages based on the maximum possible phosphorus content of the used bLG powders.

| pH | Temp °C./min/sec | bLG w/w % (E %) | Rapeseed oil in w/w % (E %) | Sucrose w/w % (E %) | Energy k cal/100 mL | Phosphorous mg/100 g protein |
|---|---|---|---|---|---|---|
| 3.5 | 95° C./5 min | 6.0 (20) | 4.7 (35) | 13.5 (45) | 120 | 20* |
| 3.5 | 95° C./5 min | 6.0 (20) | 2.7 (20) | 18.0 (60) | 120 | 20* |
| 3.5 | 95° C./5 min | 6.0 (20) | 7.3 (55) | 7.5 (25) | 120 | 20* |

Because the phosphorous content in all of the raw materials used is low, the final beverages comprising considerably lower than 80 mg/100 g protein (see table 28) makes these bLG beverages especially suited for delivery of protein, fat and carbohydrate nutrients to kidney disease patients.

Example 16a: Milky Whey Protein Beverages, with Added Minerals and Low Temperature Heat-Treatment The BLG powder used in this example had a pH of 3.79, comprising about 98.2% w/w of the protein as BLG (see table 3 in Example 6b). The content of the minerals sodium, potassium, calcium and magnesium and phosphor in the powder used are all below the detection limit.

BLG beverages comprising 6 wt % protein having a pH of 4.2, 4.4 and 4.6 were prepared as described in Example 3. The BLG beverages comprised the minerals Na, K, Ca and Mg, the mineral concentration is described in table 298 below.

TABLE 29

| Mineral concentration of BLG beverages | | | |
|---|---|---|---|
| 6% protein 75° C. for 5 min. | pH 4.2 | pH 4.4 | pH 4.6 |
| Sodium, mM | 10.4 | 13.7 | 16.9 |
| Potassium, mM | 11.3 | 11.0 | 11.0 |
| Calcium, mM | 5.9 | 5.8 | 5.9 |
| Magnesium, mM | 1.5 | 1.5 | 1.5 |
| Σ(Na, K, Ca, Mg) mM | 29.1 | 32.1 | 35.3 |

The beverages were heat-treated to 75° C. for 5 min using a water bath as outlined in example 4.

The turbidity (example 1.7), the viscosity (example 1.8), insoluble protein matter (example 1.10) and the colour (example 1.9) of the different samples were analyzed.

The results are presented in table 30 below.

TABLE 30

Turbidity, viscosity, insoluble protein matter and colour of BLG beverages after addition of minerals (Na, K, Ca, and Mg) heated at 75° C. for 5 min at pH 4.2, 4.4 and 4.6.

| 6% protein 75° C. for 5 min. | pH 4.2 | pH 4.4 | pH 4.6 |
|---|---|---|---|
| Turbidity NTU | 1868 | 3511 | 4883 |
| Viscosity cP | 0.7 | 1.5 | 1.5 |

TABLE 30-continued

Turbidity, viscosity, insoluble protein matter and colour of BLG beverages after addition of minerals (Na, K, Ca, and Mg) heated at 75° C. for 5 min at pH 4.2, 4.4 and 4.6.

| 6% protein 75° C. for 5 min. | pH 4.2 | pH 4.4 | pH 4.6 |
|---|---|---|---|
| Insoluble protein matter % | 2% | 4% | 0% |
| b* | −2.39 | −4.8 | −4.3 |
| a* | −0.11 | −0.9 | −0.88 |
| L* | 33.98 | 43.91 | 45.63 |
| Δb* | −2.17 | −4.58 | −4.08 |
| Δa* | −0.11 | −0.9 | −0.88 |
| ΔL* | −5.99 | 3.94 | 5.66 |

Results:

It was found that stable (0-4% insoluble protein matter) and native (Trp flu ratios from 1.16 to 1.17) BLG beverages, with a low viscosity (0.7-1.5 cP) and low yellowness negative (b*) could be produced by thermal treatment at 75° C. for 5 min at pH values from pH 4.2 to 4.6 even at elevated mineral contents with Na, K, Ca and Mg summarizing to 29.1-35.3 mM (table 29).

Example 16b: Milky Whey Protein Beverages, with Added Minerals and Carbohydrates at Low Temperature Heat-Treatment The BLG powder used in this example had a pH of 3.79 comprising about 98.2% w/w of the protein as BLG (see table 3 in Example 6b). The content of the minerals sodium, potassium, calcium and magnesium and phosphor in the powder are all below the detection limit.

BLG beverages comprising 6 wt % and 10 wt % protein having a pH of 4.2 were prepared as described in Example 3. The BLG beverages comprised the minerals Na, K, Ca and Mg, the mineral concentration is described in table 31 below. The beverages also comprised 5 wt % or 18 wt % sucrose.

TABLE 31

| Mineral concentration of BLG beverages | | | |
|---|---|---|---|
| pH 4.2 75° C. for 5 min. | % of total energy: Protein 25% E Carbo. 75% E Protein (6 w/w %) Sucrose (18 w/w %) | % of total energy: Protein 54.5% E Carbo. 45.5% E Protein (6 w/w %) Sucrose (5 w/w %) | % of total energy: Protein 66.7% E Carbo. 33.3% E Protein (10 w/w %) Sucrose (5 w/w %) |

TABLE 31-continued

Mineral concentration of BLG beverages

| | | | |
|---|---|---|---|
| Sodium, mM | 10.4 | 13.7 | 16.9 |
| Potassium, mM | 11.3 | 11.0 | 11.0 |
| Calcium, mM | 5.9 | 5.8 | 5.9 |
| Magnesium, mM | 1.5 | 1.5 | 1.5 |
| Σ(Na, K, Ca, Mg) | 29.1 | 32.1 | 35.3 |

The beverages were heat-treated to 75° C. for 5 min using a water bath as outlined in example 4.

The turbidity (example 1.7), the viscosity (example 1.8), and insoluble protein matter (example 1.10) of the different samples were analyzed.

The results are presented in table 32 below.

TABLE 32

Turbidity, viscosity and insoluble particles of BLG beverages after addition of minerals (Na, K, Ca, and Mg) and carbohydrates and heated at 75° C. for 5 min at pH 4.2.

| pH 4.2<br>75° C. for<br>5 min. | % of total<br>energy:<br>Protein 25% E<br>Carbo. 75% E<br>Protein<br>(6 w/w %)<br>Sucrose<br>(18 w/w %) | % of total<br>energy:<br>Protein 54.5% E<br>Carbo. 45.5% E<br>Protein<br>(6 w/w %)<br>Sucrose<br>(5 w/w %) | % of total<br>energy:<br>Protein 66.7% E<br>Carbo. 33.3% E<br>Protein<br>(10 w/w %)<br>Sucrose<br>(5 w/w %) |
|---|---|---|---|
| Turbidity NTU | 502 | 901.9 | 1907.5 |
| Viscosity cP | 3.6 | 2.6 | 3.4 |
| Insoluble protein matter % | 0.7% | 1.4% | 1.0% |

Results:

It was surprisingly found that milky beverages that comprise both sucrose and minerals (Na, K, Ca and Mg components summarizing to 29.1-35.3 mM) were produced. These beverages have a low viscosity (below 3.6 cP) and a high stability (<1.4% insoluble particles).

The invention claimed is:

1. A packaged, heat-treated beverage preparation having a pH in the range of 2-4.7, the beverage preparation comprising:
    a total amount of protein of 5 to 45% w/w relative to the weight of the beverage preparation, wherein at least 85% w/w of the total amount of protein is beta-lactoglobulin (BLG),
    wherein the beverage preparation optionally further comprises a sweetener, sugar polymers and/or flavour,
    wherein the beverage preparation has a degree of protein denaturation of at most 10%, and
    wherein the beverage preparation is at least pasteurized.

2. The packaged, heat-treated beverage preparation according to claim 1, wherein the preparation is sterile.

3. The packaged, heat-treated beverage preparation according to claim 1, wherein the protein fraction of the beverage preparation has an intrinsic tryptophan fluorescence emission ratio (1330 nm/1350 nm) of at least 1.11.

4. The packaged, heat-treated beverage preparation according to claim 1, having a pH in the range of 3.0-4.3.

5. The packaged, heat-treated beverage preparation according to claim 1, wherein the protein fraction of the beverage preparation has a colour value delta b* in the range of −0.10 to +0.51 at the CIELAB colour scale, wherein delta b*=b.sub.sample standardized to 6.0 w/w % protein*−b.sub.demin. water*, measured at room temperature.

6. The packaged, heat-treated beverage preparation according to claim 1, wherein the beverage preparation has a colour value delta b* in the range of −0.10 to +0.51 at the CIELAB colour scale, wherein delta b*−b.sub.sample standardized to 6.0 w/w % protein*−b.sub.demin. water*, measured at room temperature.

7. The packaged, heat-treated beverage preparation according to claim 1, wherein the sum of the amounts of Na, K, Mg and Ca is at most 750 mM.

8. The packaged, heat-treated beverage preparation according to claim 1, having a turbidity of at most 200 NTU.

9. The packaged, heat-treated beverage preparation according to claim 1, having a turbidity of more than 200 NTU.

10. The packaged, heat-treated beverage preparation according to claim 1, having a viscosity of at most 200 cP centipoise, measured at 22 degrees Celsius at a shear rate of 100/s.

11. The packaged, heat-treated beverage preparation according to claim 1, comprising a total amount of protein of 10 to 45% w/w relative to the weight of the beverage.

12. The packaged, heat-treated beverage preparation according to claim 1, wherein each main non-BLG whey protein is present in a weight percentage relative to total protein which is at most 15% of its weight percentage relative to total protein in a standard whey protein concentrate from sweet whey.

13. The packaged, heat-treated beverage preparation according to claim 1, comprising a BLG isolate.

14. The packaged, heat-treated beverage preparation according to claim 1, wherein at least 90% w/w of the protein is beta-lactoglobulin (BLG).

15. The packaged, heat-treated beverage preparation according to claim 1, comprising a total amount of protein of 10 to 30% w/w relative to the weight of the beverage.

16. The packaged, heat-treated beverage preparation according to claim 1, wherein each main non-BLG whey protein is present in a weight percentage relative to total protein which is at most 10% of its weight percentage relative to total protein in a standard whey protein concentrate from sweet whey.

17. The packaged, heat-treated beverage preparation according to claim 1, wherein each main non-BLG whey protein is present in a weight percentage relative to total protein which is at most 6% of its weight percentage relative to total protein in a standard whey protein concentrate from sweet whey.

18. The packaged, heat-treated beverage preparation according to claim 1, wherein each main non-BLG whey protein is present in a weight percentage relative to total protein which is at most 4% of its weight percentage relative to total protein in a standard whey protein concentrate from sweet whey.

19. The packaged, heat-treated beverage preparation according to claim 1, wherein at least 92% w/w of the protein is beta-lactoglobulin (BLG).

20. A method of producing a packaged, heat-treated beverage preparation having a pH in the range of 2-4.7, comprising the following steps:
    a) providing a liquid solution comprising a total amount of protein of 5 to 45% w/w relative to the weight of the liquid solution, wherein at least 85% of the total amount of protein is BLG, having a pH in the range of 2-4.7,
        wherein the liquid solution optionally further comprises a sweetener, sugar polymers and/or flavour,
        wherein the liquid solution has a degree of protein denaturation of at most 10%, b) packaging the liquid solution, wherein the liquid solution of step a) and/or the packaged liquid solution of step b) is subjected to a heat-treatment comprising at least pasteurization.

21. The method according to claim 20, wherein the heat-treatment involves heating at a temperature in the range of 70-82 degrees C.

22. A method of treating a subject who suffers from diseases associated with protein malabsorption, the method comprising providing to the subject the packaged, heat-treated beverage preparation of claim 1.

23. A method of treating a subject who is in need of a dietary supplement, the method comprising providing to the subject the packaged, heat-treated beverage preparation of claim 1.

24. The method of claim 23, wherein said beverage preparation is ingested before, during or after exercise.

\* \* \* \* \*